(12) United States Patent
Janna et al.

(10) Patent No.: US 9,445,720 B2
(45) Date of Patent: Sep. 20, 2016

(54) PROCESSING SENSED ACCELEROMETER DATA FOR DETERMINATION OF BONE HEALING

(75) Inventors: Sied W. Janna, Memphis, TN (US); Darren James Wilson, York (GB); Peter A. Brady, Ely (GB)

(73) Assignee: Smith & Nephew, Inc., Memphis, TN (US)

( * ) Notice: Subject to any disclaimer, the term of this patent is extended or adjusted under 35 U.S.C. 154(b) by 1529 days.

(21) Appl. No.: 12/528,243

(22) PCT Filed: Feb. 23, 2007

(86) PCT No.: PCT/US2007/062757
§ 371 (c)(1),
(2), (4) Date: Feb. 26, 2010

(87) PCT Pub. No.: WO2008/103181
PCT Pub. Date: Aug. 28, 2008

(65) Prior Publication Data
US 2010/0152621 A1    Jun. 17, 2010

(51) Int. Cl.
*A61B 5/03* (2006.01)
*A61B 5/00* (2006.01)
(Continued)

(52) U.S. Cl.
CPC ........... *A61B 5/0031* (2013.01); *A61B 5/1038* (2013.01); *A61B 5/412* (2013.01);
(Continued)

(58) Field of Classification Search
CPC   A61B 5/4504; A61B 5/4509; A61B 5/7253; A61B 5/7257; A61B 2562/0219
USPC ............... 600/552, 553, 587, 592, 594, 595; 340/669
See application file for complete search history.

(56) References Cited

U.S. PATENT DOCUMENTS

| | | |
|---|---|---|
| 3,713,148 A | 1/1973 | Cardullo et al. |
| 3,727,209 A | 4/1973 | White et al. |

(Continued)

FOREIGN PATENT DOCUMENTS

| | | |
|---|---|---|
| DE | 19855254 | 6/2000 |
| EP | 0062459 | 12/1986 |

(Continued)

OTHER PUBLICATIONS

Fruin, et al, "Validity of a Multi-Sensor Armband in Estimating Rest and Exercise Energy Expenditure", Am Coll Sports Med, vol. 36, 6, pp. 1063-1069, 2004.

(Continued)

*Primary Examiner* — Adam J Eiseman
(74) *Attorney, Agent, or Firm* — Fish & Richardson P.C.

(57) ABSTRACT

A system (800) for processing accelerometer data is disclosed. The system (800) includes an accelerometer (806), a first processor (810), a power supply (816), and a second processor (804). The accelerometer (806) measures a physiological acceleration parameter. The first processor (810) is operatively connected to the accelerometer (806). The first processor (810) is configured to receive the acceleration parameter from the accelerometer (806) and configured to output machine readable acceleration data. The machine readable acceleration data includes time domain accelerometer data. The power supply (816) is electrically connected to the first processor (810). The second processor (804) is configured to receive the machine readable acceleration data and transform the time domain accelerometer data into frequency domain accelerometer data. The frequency domain accelerometer data may be used to estimate patient healing status.

27 Claims, 26 Drawing Sheets

(51) Int. Cl.
*A61B 5/103* (2006.01)
*A61B 5/11* (2006.01)

(52) U.S. Cl.
CPC .......... *A61B 5/4504* (2013.01); *A61B 5/6807* (2013.01); *A61B 5/11* (2013.01); *A61B 5/7257* (2013.01); *A61B 2562/0219* (2013.01)

(56) References Cited

U.S. PATENT DOCUMENTS

| | | | |
|---|---|---|---|
| 3,976,060 A | | 8/1976 | Hildebrandt et al. |
| 4,096,477 A | | 6/1978 | Epstein et al. |
| 4,242,663 A | | 12/1980 | Slobodin |
| 4,281,664 A | | 8/1981 | Duggan |
| 4,361,153 A | | 11/1982 | Slocum et al. |
| 4,441,498 A | | 4/1984 | Nordling |
| 4,473,825 A | | 9/1984 | Walton |
| 4,481,428 A | | 11/1984 | Charlot |
| 4,494,545 A | | 1/1985 | Slocum et al. |
| 4,510,495 A | | 4/1985 | Sigrimis et al. |
| 4,513,743 A | | 4/1985 | van Arragon et al. |
| 4,525,713 A | | 6/1985 | Barletta et al. |
| 4,546,241 A | | 10/1985 | Walton |
| 4,571,589 A | | 2/1986 | Slocum et al. |
| 4,576,158 A | | 3/1986 | Boland |
| 4,944,299 A | | 7/1990 | Silvian |
| 4,952,928 A | | 8/1990 | Carroll et al. |
| 4,991,682 A | | 2/1991 | Kuntz et al. |
| 5,024,239 A | | 6/1991 | Rosenstein |
| 5,030,236 A | | 7/1991 | Dean |
| 5,042,504 A | | 8/1991 | Huberti |
| 5,117,825 A | | 6/1992 | Grevious |
| 5,197,488 A | | 3/1993 | Kovacevic |
| 5,252,962 A | | 10/1993 | Urbas et al. |
| 5,309,919 A | | 5/1994 | Snell et al. |
| 5,326,363 A | | 7/1994 | Aikins |
| 5,330,477 A | | 7/1994 | Crook |
| 5,334,202 A | | 8/1994 | Carter |
| 5,337,747 A | | 8/1994 | Neftel |
| 5,360,016 A | | 11/1994 | Kovacevic |
| 5,383,935 A | | 1/1995 | Shirkhanzadeh |
| 5,416,695 A | | 5/1995 | Stutman et al. |
| 5,423,334 A | | 6/1995 | Jordan |
| 5,425,775 A | | 6/1995 | Kovacevic |
| 5,456,724 A | | 10/1995 | Yen et al. |
| 5,470,354 A | | 11/1995 | Hershberger et al. |
| 5,481,262 A | | 1/1996 | Urbas et al. |
| 5,518,008 A | * | 5/1996 | Cucchiaro et al. ............ 600/590 |
| 5,524,637 A | * | 6/1996 | Erickson ...................... 600/592 |
| 5,533,519 A | | 7/1996 | Radke et al. |
| 5,626,630 A | | 5/1997 | Markowitz et al. |
| 5,630,835 A | | 5/1997 | Brownlee |
| 5,681,313 A | | 10/1997 | Diez |
| 5,695,496 A | | 12/1997 | Orsak et al. |
| 5,733,292 A | | 3/1998 | Gustilo |
| 5,735,887 A | | 4/1998 | Barreras et al. |
| 5,741,315 A | | 4/1998 | Lee et al. |
| 5,792,076 A | | 8/1998 | Orsak et al. |
| 5,807,701 A | | 9/1998 | Payne et al. |
| 5,833,603 A | | 11/1998 | Kovacs et al. |
| 5,836,989 A | | 11/1998 | Shelton |
| 5,873,843 A | | 2/1999 | Draper |
| 5,904,708 A | | 5/1999 | Goedeke |
| 5,935,171 A | | 8/1999 | Schneider et al. |
| 5,944,745 A | | 8/1999 | Rueter |
| 6,009,878 A | | 1/2000 | Weijand et al. |
| 6,025,725 A | | 2/2000 | Gershenfeld et al. |
| 6,034,295 A | | 3/2000 | Rehberg et al. |
| 6,034,296 A | | 3/2000 | Elvin et al. |
| 6,059,576 A | | 5/2000 | Brann |
| 6,061,597 A | * | 5/2000 | Rieman et al. ................. 607/51 |
| 6,102,874 A | | 8/2000 | Stone et al. |
| 6,111,520 A | | 8/2000 | Allen et al. |
| 6,120,502 A | | 9/2000 | Michelson |
| 6,135,951 A | | 10/2000 | Richardson et al. |
| 6,143,035 A | | 11/2000 | McDowell |
| 6,168,569 B1 | | 1/2001 | McEwen et al. |
| 6,183,425 B1 | | 2/2001 | Whalen et al. |
| 6,200,265 B1 | | 3/2001 | Walsh et al. |
| 6,201,980 B1 | | 3/2001 | Darrow et al. |
| 6,210,301 B1 | | 4/2001 | Abraham-Fuchs et al. |
| 6,245,109 B1 | | 6/2001 | Mendes et al. |
| 6,312,612 B1 | | 11/2001 | Sherman et al. |
| 6,325,756 B1 | | 12/2001 | Webb et al. |
| 6,327,501 B1 | | 12/2001 | Levine et al. |
| 6,356,789 B1 | | 3/2002 | Hinssen et al. |
| 6,369,694 B1 | | 4/2002 | Mejia |
| 6,385,593 B2 | | 5/2002 | Linberg |
| 6,402,689 B1 | | 6/2002 | Scarantino et al. |
| 6,433,629 B2 | | 8/2002 | Hamel et al. |
| 6,434,429 B1 | | 8/2002 | Kraus et al. |
| 6,442,432 B2 | | 8/2002 | Lee |
| 6,447,448 B1 | | 9/2002 | Ishikawa et al. |
| 6,447,449 B1 | | 9/2002 | Fleischman et al. |
| 6,449,508 B1 | | 9/2002 | Sheldon et al. |
| 6,466,810 B1 | | 10/2002 | Ward et al. |
| 6,477,424 B1 | | 11/2002 | Thompson et al. |
| 6,482,154 B1 | | 11/2002 | Haubrich et al. |
| 6,497,655 B1 | | 12/2002 | Linberg et al. |
| 6,499,488 B1 | | 12/2002 | Hunter et al. |
| 6,527,711 B1 | | 3/2003 | Stivoric et al. |
| 6,529,127 B2 | | 3/2003 | Townsend et al. |
| 6,535,766 B1 | | 3/2003 | Thompson et al. |
| 6,539,253 B2 | | 3/2003 | Thompson et al. |
| 6,553,262 B1 | | 4/2003 | Lang et al. |
| 6,567,703 B1 | | 5/2003 | Thompson et al. |
| 6,573,706 B2 | | 6/2003 | Mendes et al. |
| 6,583,630 B2 | | 6/2003 | Mendes et al. |
| 6,602,191 B2 | | 8/2003 | Quy |
| 6,610,096 B2 | | 8/2003 | MacDonald |
| 6,636,769 B2 | | 10/2003 | Govari et al. |
| 6,638,231 B2 | | 10/2003 | Govari et al. |
| 6,641,540 B2 | | 11/2003 | Fleischman et al. |
| 6,652,464 B2 | | 11/2003 | Schwartz et al. |
| 6,658,300 B2 | | 12/2003 | Govari et al. |
| 6,667,725 B1 | | 12/2003 | Simons et al. |
| 6,675,044 B2 | | 1/2004 | Chen |
| 6,682,490 B2 | | 1/2004 | Roy et al. |
| 6,694,180 B1 | | 2/2004 | Boesen |
| 6,706,005 B2 | | 3/2004 | Roy et al. |
| 6,712,778 B1 | | 3/2004 | Jeffcoat et al. |
| 6,738,671 B2 | | 5/2004 | Christophersom et al. |
| 6,749,568 B2 | | 6/2004 | Fleischman et al. |
| 6,764,446 B2 | | 7/2004 | Wolinsky et al. |
| 6,766,200 B2 | | 7/2004 | Cox |
| 6,783,499 B2 | | 8/2004 | Schwartz |
| 6,790,372 B2 | | 9/2004 | Roy et al. |
| 6,793,659 B2 | | 9/2004 | Putnam |
| 6,804,552 B2 | | 10/2004 | Thompson et al. |
| 6,807,439 B2 | | 10/2004 | Edwards et al. |
| 6,810,753 B2 | | 11/2004 | Valdevit et al. |
| 6,819,247 B2 | | 11/2004 | Bimbach et al. |
| 6,821,299 B2 | | 11/2004 | Kirking et al. |
| 6,834,436 B2 | | 12/2004 | Townsend et al. |
| 6,855,115 B2 | | 2/2005 | Fonseca et al. |
| 6,864,802 B2 | | 3/2005 | Smith et al. |
| 6,895,280 B2 | | 5/2005 | Meadows |
| 6,895,281 B1 | | 5/2005 | Amundson et al. |
| 6,926,670 B2 | | 8/2005 | Rich et al. |
| 6,939,299 B1 | | 9/2005 | Petersen et al. |
| 6,968,743 B2 | | 11/2005 | Rich et al. |
| 6,994,672 B2 | | 2/2006 | Fleischman et al. |
| 7,001,346 B2 | | 2/2006 | White |
| 7,027,871 B2 | | 4/2006 | Burnes et al. |
| 7,034,694 B2 | | 4/2006 | Yamaguchi et al. |
| 7,097,662 B2 | | 8/2006 | Evans |
| 7,145,461 B2 | | 12/2006 | Lehrman et al. |
| 7,147,604 B1 | | 12/2006 | Allen et al. |
| 7,151,914 B2 | | 12/2006 | Brewer |
| 7,182,736 B2 | | 2/2007 | Roy |
| 7,190,273 B2 | | 3/2007 | Liao et al. |
| 7,195,645 B2 | | 3/2007 | DiSilvestro et al. |
| 7,209,790 B2 | | 4/2007 | Thompson et al. |
| 7,212,133 B2 | | 5/2007 | Goetz et al. |
| 7,218,232 B2 | | 5/2007 | DiSilvestro |

(56) References Cited

U.S. PATENT DOCUMENTS

| | | |
|---|---|---|
| 7,229,415 B2 | 6/2007 | Schwartz |
| 7,256,695 B2 | 8/2007 | Hamel |
| 7,333,013 B2 | 2/2008 | Berger |
| 7,357,037 B2 | 4/2008 | Hnat et al. |
| 7,474,223 B2 | 1/2009 | Nycz et al. |
| 7,559,951 B2 | 7/2009 | DiSilvestro et al. |
| 7,756,579 B2 | 7/2010 | Nitzan et al. |
| 8,007,450 B2 * | 8/2011 | Williams ............... 600/595 |
| 2001/0047125 A1 | 11/2001 | Quy |
| 2002/0099359 A1 | 7/2002 | Santini, Jr. et al. |
| 2002/0116080 A1 | 8/2002 | Birnbach |
| 2002/0138153 A1 | 9/2002 | Koniuk |
| 2002/0151978 A1 | 10/2002 | Zacouto et al. |
| 2002/0170193 A1 | 11/2002 | Townsend et al. |
| 2003/0040806 A1 | 2/2003 | MacDonald |
| 2003/0069644 A1 | 4/2003 | Kovacevic et al. |
| 2003/0105470 A1 | 6/2003 | White |
| 2003/0120150 A1 | 6/2003 | Govari |
| 2003/0136417 A1 | 7/2003 | Fonseca |
| 2003/0143775 A1 | 7/2003 | Brady |
| 2003/0178488 A1 | 9/2003 | Southard |
| 2003/0229381 A1 | 12/2003 | Hochmair et al. |
| 2004/0008123 A1 | 1/2004 | Carrender et al. |
| 2004/0011137 A1 | 1/2004 | Hnat et al. |
| 2004/0014456 A1 | 1/2004 | Vaananen |
| 2004/0019382 A1 | 1/2004 | Amirouche |
| 2004/0073137 A1 | 4/2004 | Lloyd et al. |
| 2004/0073221 A1 | 4/2004 | Biscup |
| 2004/0094613 A1 | 5/2004 | Shiratori et al. |
| 2004/0113790 A1 | 6/2004 | Hamel et al. |
| 2004/0116837 A1 | 6/2004 | Yamaguchi et al. |
| 2004/0152972 A1 | 8/2004 | Hunter |
| 2004/0176815 A1 | 9/2004 | Janzig et al. |
| 2004/0186396 A1 | 9/2004 | Roy et al. |
| 2004/0204647 A1 | 10/2004 | Grupp et al. |
| 2004/0231420 A1 | 11/2004 | Xie et al. |
| 2004/0243148 A1 | 12/2004 | Wasielewski |
| 2004/0249315 A1 | 12/2004 | Damen |
| 2005/0010139 A1 * | 1/2005 | Aminian et al. ............... 600/595 |
| 2005/0010299 A1 | 1/2005 | Disilvestro et al. |
| 2005/0010300 A1 | 1/2005 | Disilvestro et al. |
| 2005/0010301 A1 | 1/2005 | Disilvestro et al. |
| 2005/0010302 A1 | 1/2005 | Dietz et al. |
| 2005/0012610 A1 | 1/2005 | Liao et al. |
| 2005/0012617 A1 | 1/2005 | DiSilvestro et al. |
| 2005/0015014 A1 | 1/2005 | Fonseca et al. |
| 2005/0061079 A1 * | 3/2005 | Schulman ............... 73/715 |
| 2005/0099290 A1 | 5/2005 | Govari |
| 2005/0101833 A1 | 5/2005 | Hsu et al. |
| 2005/0113932 A1 | 5/2005 | Kovacevic |
| 2005/0131397 A1 | 6/2005 | Levin |
| 2005/0187482 A1 | 8/2005 | O'Brien et al. |
| 2005/0194174 A1 | 9/2005 | Hipwell, Jr. et al. |
| 2005/0234555 A1 | 10/2005 | Sutton et al. |
| 2005/0247319 A1 | 11/2005 | Berger |
| 2005/0273170 A1 | 12/2005 | Navarro et al. |
| 2005/0288727 A1 | 12/2005 | Penner |
| 2006/0009856 A1 | 1/2006 | Sherman et al. |
| 2006/0030771 A1 | 2/2006 | Levine |
| 2006/0032314 A1 | 2/2006 | Hnat et al. |
| 2006/0043178 A1 | 3/2006 | Tethrake et al. |
| 2006/0043179 A1 | 3/2006 | Nycz et al. |
| 2006/0047283 A1 | 3/2006 | Evans, III et al. |
| 2006/0052782 A1 | 3/2006 | Morgan et al. |
| 2006/0058627 A1 | 3/2006 | Flaherty |
| 2006/0065739 A1 | 3/2006 | Falls et al. |
| 2006/0069436 A1 | 3/2006 | Sutton et al. |
| 2006/0069447 A1 | 3/2006 | Disilvestro et al. |
| 2006/0109105 A1 | 5/2006 | Varner et al. |
| 2006/0111291 A1 | 5/2006 | DiMauro et al. |
| 2006/0119481 A1 | 6/2006 | Tethrake et al. |
| 2006/0142656 A1 | 6/2006 | Malackowski et al. |
| 2006/0145871 A1 | 7/2006 | Donati et al. |
| 2006/0174712 A1 | 8/2006 | O'Brien et al. |
| 2006/0177956 A1 | 8/2006 | O'Brien et al. |
| 2006/0190080 A1 | 8/2006 | Danoff et al. |
| 2006/0196277 A1 | 9/2006 | Allen et al. |
| 2006/0200030 A1 | 9/2006 | White et al. |
| 2006/0200031 A1 | 9/2006 | White et al. |
| 2006/0235310 A1 | 10/2006 | O'Brien et al. |
| 2006/0241354 A1 | 10/2006 | Allen |
| 2006/0244465 A1 | 11/2006 | Kroh et al. |
| 2006/0260401 A1 | 11/2006 | Xie et al. |
| 2006/0271199 A1 | 11/2006 | Johnson |
| 2006/0283007 A1 | 12/2006 | Cros et al. |
| 2006/0287602 A1 | 12/2006 | O'Brien et al. |
| 2006/0287700 A1 | 12/2006 | White et al. |
| 2007/0038051 A1 | 2/2007 | Talman et al. |
| 2007/0078497 A1 | 4/2007 | Vandanacker |
| 2007/0089518 A1 | 4/2007 | Ericson et al. |
| 2007/0090543 A1 | 4/2007 | Condie et al. |
| 2007/0100215 A1 | 5/2007 | Powers et al. |
| 2007/0129769 A1 | 6/2007 | Bourget et al. |
| 2007/0180922 A1 | 8/2007 | Crottet et al. |
| 2007/0208544 A1 * | 9/2007 | Kulach et al. ............... 702/189 |
| 2007/0219639 A1 | 9/2007 | Otto et al. |
| 2008/0086145 A1 | 4/2008 | Sherman et al. |
| 2008/0105874 A1 | 5/2008 | Wang et al. |
| 2008/0161729 A1 | 7/2008 | Bush |
| 2008/0208516 A1 * | 8/2008 | James ............... 702/141 |
| 2008/0300597 A1 | 12/2008 | Morgan et al. |
| 2009/0131838 A1 * | 5/2009 | Fotiadis et al. ............... 601/2 |
| 2009/0222050 A1 | 9/2009 | Wolter et al. |

FOREIGN PATENT DOCUMENTS

| | | |
|---|---|---|
| EP | 1023872 | 8/2000 |
| EP | 1099415 | 5/2001 |
| EP | 0959956 | 12/2001 |
| EP | 1256316 | 11/2002 |
| EP | 1309960 | 5/2003 |
| EP | 1331903 | 8/2003 |
| EP | 1366712 | 12/2003 |
| EP | 1466557 A2 | 10/2004 |
| EP | 1495456 | 1/2005 |
| EP | 1502540 | 2/2005 |
| EP | 0987047 | 4/2005 |
| EP | 1535039 | 6/2005 |
| EP | 1541095 | 6/2005 |
| EP | 1570781 | 9/2005 |
| EP | 1570782 | 9/2005 |
| EP | 1582183 | 10/2005 |
| EP | 1586287 | 10/2005 |
| EP | 1611835 | 1/2006 |
| EP | 1642550 | 4/2006 |
| EP | 1765204 | 3/2007 |
| EP | 1377340 | 5/2007 |
| EP | 1803394 | 7/2007 |
| EP | 1830303 | 9/2007 |
| JP | 2004261525 | 9/2004 |
| WF | 2006/113660 | 10/2006 |
| WF | 2007/002185 | 1/2007 |
| WF | 2007/002225 | 1/2007 |
| WO | 82/00378 | 2/1982 |
| WO | 90/06720 | 6/1990 |
| WO | WO9621397 A1 | 7/1996 |
| WO | 96/26678 | 9/1996 |
| WO | 96/29007 | 9/1996 |
| WO | 97/14367 | 4/1997 |
| WO | 97/20512 | 6/1997 |
| WO | WO9843701 A1 | 10/1998 |
| WO | 00/18317 | 4/2000 |
| WO | 00/19888 | 4/2000 |
| WO | 00/30534 | 6/2000 |
| WO | 00/32124 | 6/2000 |
| WO | 01/19248 | 3/2001 |
| WO | 01/37733 | 5/2001 |
| WO | 02/03347 | 1/2002 |
| WO | 02/38082 | 5/2002 |
| WO | 02/056763 | 7/2002 |
| WO | 02/058551 | 8/2002 |
| WO | 02/061705 | 8/2002 |
| WO | 03/003145 | 1/2003 |
| WO | 03/008570 | 1/2003 |

(56) References Cited

FOREIGN PATENT DOCUMENTS

| | | |
|---|---|---|
| WO | 03/044556 | 5/2003 |
| WO | 03/085617 | 10/2003 |
| WO | 2004/005872 | 1/2004 |
| WO | 2004/014456 | 2/2004 |
| WO | 2004/052453 | 6/2004 |
| WO | 2004/052456 | 6/2004 |
| WO | 2004/077073 | 9/2004 |
| WO | 2005/007025 | 1/2005 |
| WO | 2005/013851 | 2/2005 |
| WO | 2005/039440 | 5/2005 |
| WO | 2005/074821 | 8/2005 |
| WO | 2005/084544 | 9/2005 |
| WO | 2005/104997 | 11/2005 |
| WO | 2005/120203 | 12/2005 |
| WO | 2006/010037 | 1/2006 |
| WO | 2006/045080 | 4/2006 |
| WO | 2006/045607 | 5/2006 |
| WO | 2006/049796 | 5/2006 |
| WO | 2006/052765 | 5/2006 |
| WO | 2006/055547 | 5/2006 |
| WO | 2006/063156 | 6/2006 |
| WO | 2006/086113 | 8/2006 |
| WO | 2006/086114 | 8/2006 |
| WO | 2006/089069 | 8/2006 |
| WO | 2006/094273 | 9/2006 |
| WO | 2006/096582 | 9/2006 |
| WO | 2006/110798 | 10/2006 |
| WO | 2007/002224 | 1/2007 |
| WO | 2007/008493 | 1/2007 |
| WO | 2007/009088 | 1/2007 |
| WO | 2007/025191 | 3/2007 |
| WO | 2007/030489 | 3/2007 |
| WO | 2007/036318 | 4/2007 |
| WO | WO2007041124 A1 | 4/2007 |
| WO | 2007/061890 | 5/2007 |
| WO | 2007/090543 | 8/2007 |
| WO | 2008/105874 | 9/2008 |
| WO | 2009/098768 | 8/2009 |

OTHER PUBLICATIONS

Jakicic, et al, "Evaluation of the SenseWear Pro Armband™ to Assess Energy Expenditure during Exercise", Med. Sci. Sports Exerc.; vol. 36,5, pp. 897-904, 2004.
Nachemson et al., "Intravital wireless telemetry of axial forces in Harrington distraction rods in patients with idiopathic scoliosis", J.Bone Jt Surg. 53A, 445-464 (Apr. 1971).
Burny, et al., "Smart orthopedic implants", Orthopedics, Dec. 2005; 28 (12):1401.
Rydell, "Forces Acting on the Femoral Head Prosthesis", Acta Orthop Scand, Suppl. 88, 1966.
Lanyon, et al., "In Vivo Strain Measurements from Bone and Prosthesis following Total Hip Replacement", The Journal of Bone and Joint Surgery, vol. 63-A,No. 6,pp. 989-1000, 1981.
Carlson, et al., "A Radio Telemetry Device for Monitoring Cartilage Surface Pressures in the Human Hip", IEEE Trans. on Biomed. Engrg.,vol. BME-21,No. 4, pp. 257-264, Jul. 1974.
Carlson, et al, "A look at the prosthesis-cartilage interface: design of a hip prosthesis containing pressure transducers", J Biomed Mater Res. 1974; 8(4 pt 2): 261-269.
English, et al., "In vivo records of hip loads using a femoral implant with telemetric output (a preliminary report)," J Biomed Eng. 1979; 1(2):111-115.
Rushfeldt, et al., Improvd Techniques for Measuring In Vitro Geometry and Pressure Distribution in Human Acetabulum-II. Instrumented . . . J Biomechanics No. 14, pp. 315-323, 1981.
Hodge, et al., "Preliminary In Vivo Pressure Measurements in a Human Acetabulum", Proceedings of 31 st Annual Meeting, Orthopaedic Research Society, 1985.
Hodge, et al., "Contact Pressures in the Human Hip Joint Measured In Vivo", Proc. of National Academy of Science, U.S.A., No. 83, pp. 2879-2883, 1986.
Brown, et al., "In Vivo Load Measurements on a Total Hip Prosthesis", Proceedings of the 31 st Meeting, Orthopaedic Research Society, 1985.
Davy, et al., "Telemetric Force Measurements across the Hip after Total Arthroplasty", Journal of Bone and Joint Surgery, vol. 70-A, No. 1, Jan. 1988: 45-50.
Taylor, et al., "Telemetry of forces from proximal femoral replacements and relevance to fixation", J Biomech. 1997; 30:225-234.
Bergmann, et al., "Multichannel Strain Gauge Telemetry for Orthopaedic Implants", Technical Note, J. Biomechanics, vol. 21, No. 2, pp. 169-176, 1988.
Rohlmann, et al., "Telemeterized Load Measurement Using Instrumented Spinal Internal Fixators in a Patient with Degenerative Instability", Spine, vol. 20, No. 24, 1995.
Berkman, et al., "Biomedical Micropressor with Analog I/O", Inter. Solid-State Circuits Conf. Digest of Technical Papers, pp. 168-169, 1981.
Dorman, et al., "A Monolithic Signal Processor for a Neurophysiological Telemetry System", IEEE Journal of Solid-State Circuits, vol. 20, pp. 1185-1193, 1985.
Gschwend, et al., "A General Purpose Implantable Multichannel Telemetry System for Physiological Research", Biotelemetry Patient Monitoring, vol. 6, pp. 107-117, 1979.
Cook, et al., "A Custom Microprocessor for Implantable Telemetry Systems", Proc of the IEEE Symp. on Computer-Based Medical Systems, pp. 412-417, Jun. 1990.
Brown, et al., "Telemetering In Vivo Loads from Nail Plate Implants", J. Biomechanics, vol. 15, No. 11, pp. 815-823, 1982.
Fernald, et al., "A System Architecture for Intelligent Implantable Biotelemetry Instruments", Proc. IEEE Eng in Medicine and Biology Soc. Annual Conf., pp. 1411-1412, 1989.
Rohlmann, et al., "Influence of load carrying on loads in internal spinal fixators", J Biomech. 2000; 33:1099-1104.
Rohlmann, et al., "Loads on an internal spinal fixation device during walking", J Biomech, 1997; 30:41-47.
Schneider, et al, "Loads acting in an intramedullary nail during fracture healing in the human femur", Journal of Biomechanics 34, 2001, pp. 849-857.
Heinlein, et al., "An instrumented knee endoprosthesis for measuring loads in vivo", EORS 2004, 51st Annual Meeting of the Orthopaedic research Society, Aug. 2007, 1 page.
Townsend, et al., Multichannel, Programmable, Microprocessor Based Strain Gauge . . . , 18th Ann. Int Conf. IEEE Eng. in Med & Biology Soc. Oct. 31-Nov. 3, 1996, Amsterdam.
Mendes, et al., "IntelliJoint System for monitoring displacement in biologic system", Biomed Bytes 2002 (4), pp. 69-70.
Cristofolini, et al., "A novel transducer for the measurement of cement-prosthesis interface forces in cemented . . . ", Medicial Eng & Physics vol. 22, 7, Sep. 2000, pp. 493-501.
Müller, Otto, et al., "Three-dimensional measurements of the pressure distribution in artificial joints with a capacitive sensor array", J Biomech, vol. 37, Oct. 2004, pp. 1623-1625.
Bergmann, et al., "Frictional Heating of Total Hip Implants. Part 1: Measurements in Patients," Journal of Biomechanics, vol. 34, Issue 4, Apr. 2001, pp. 421-428.
Rohlmann, et al., "In vitro load measurement using an instrumented spinal fixation device", Medical Engineering & Physics, vol. 18, Issue 6, Sep. 1996, pp. 485-488.
Burny, et al., "Concept, design and fabrication of smart orthopaedic implants", Medical Engineering & Physics, 22 (2000), pp. 469-479.
Townsend, et al., "Remotely powered multichannel microprocessor based telemetry systems for smart implantable devices and smart structures," Proc. SPIE vol. 3673, pp. 150-156 (Mar. 1999).
D'Lima, et al., "An implantable telemetry device to measure intra-articular tibial forces", J Biomech. Feb. 2005; 38(2): pp. 299-304.
Bergmann, et al., "Hip Joint Contact Forces during Stumbling", Langenbecks Arch Surg. Feb. 2004; 389(1): 53-9. Epub Nov. 19, 2003.
Stansfield, et al., "Direct comparison of calculated hip joint contact forces with those measured using instrumented implants . . . " J Biomech. Jul. 2003;36(7):929-36.

(56) References Cited

OTHER PUBLICATIONS

Heller, et al., "Musculo-skeletalloading conditions at the hip during walking and stair climbing", J Biomech. Jul. 2001; 34(7):883-93.
Bergmann, et al., "Hip Contact Forces and Gait Patterns from Routing Activities", J. Biomech. Jul. 2001;34(7):859-71.
Bergmann, et al., "Frictional Heating of Total Hip Implants. Part 2: Finite Element Study," J Biomech. Apr. 2001;34(4):429-35.
Park, et al, "Hip muscle co-contraction: evidence from concurrent in vivo pressure measurement and force estimation", Gait Posture. Dec. 1999;10(3):211-22.
Graichen, et al., "Hip endoprosthesis for in vivo measurement of joint force and temperature", J. Biomech Oct. 1999; 32(10):1113-7.
Krebs, et al., "Hip Biomechanics during Gait", J Orthop & Sports Phys Ther. Jul. 1998; 28(1):51-9.
Tackson, et al., "Acetabular pressures during hip arthritis exercises", Arthritis Care & Res. Oct. 1997;10(5):308-19.
Kotzar, et al, "Torsional loads in the early postoperative period following total hip replacement", J Orthop Res. Nov. 1995;13(6):945-55.
Bergmann, et al, "Is staircase walking a risk for the fixation of hip implants?," J Biomech, May 1995; 28(5):535-53.
Brand, et al, "Comparison of hip force calculations and measurements in the same patient", J Arthroplasty, Feb. 1994; 9(1):45-51.
Bergmann, et al., "Hip joint loading during walking and running, measured in two patients", J Biomech, Aug. 1993;26(8):969-90.
Graichen, et al., "Four-channel telemetry system for in vivo measurement of hip joint forces", J Sioment Eng, Sep. 1991;13(5):370-4.
Kotzar, et al., "Telemeterized in vivo hip joint force data: a report on two patients after total hip surgery", J Orthop Res., Sep. 1991, 9(5):621-33.
Morrell, et al., "Corroboration of in vivo cartilage pressures with implacations for synovial joint tribology and . . . ", Proc Natl Acad Sci USA, Oct. 11, 2005; 102(41 ):14819-24.
McGibbon, et al., "Cartilage degeneration in relation to repetitive pressure: case study of a unilateral hip hemiarthroplasty patient". J Arthroplasty, Jan. 1999, 14(1):52-8.
Lu, et al., "Influence of muscle activity on the forces in the femur: An in vivo study", J Biomech, Nov.-Dec. 1997;30(11-12):1101-6.
Taylor, et al., "Telemetry of forces from proximal femoral replacements and relevance to fixation", J Biomech, Mar. 1997;30(3):225-34.
Puers, et al., "A telemetry system for the detection of hip prosthesis loosening by vibration analysis", Sensors and Actuators 85 (2000) 42-47.
Aminian K, et al., "Temporal Feature Estimation During Walking Using Miniature Accelerometers . . . " Med Biol Eng Comput, 1999, 37, 686-691.
Bussmann JBJ, et al., "Analysis and Decomposition of Signals Obtained by Thigh-Fixed Uni-Axial Accelerometry During Normal Walking," Med Biol Eng Comput, 2000, 38, 632-638.
Petrofsky JS, et al., "Joint Acceleration during Gait in Relation to Age," Eur J Appl Physiology. 2004, 92: 254-262.
U.S. Appl. No. 60/710,550, filed Aug. 23, 2005.
International Search Report for International Application PCT/US2005/040052 dated Jun. 22, 2006, 8 pages.
Written Opinion of the International Search Authority issued in PCT/US2005/040052 on May 20, 2006, 9 pages.
International Preliminary Report on Patentability issued in PCT/US2005/040052 on May 8, 2007, 10 pages.
International Search Report for International Application PCT/US2006/033326 dated Dec. 13, 2006, 5 pages.
International Search Report and Written Opinion for International Application PCT/US2007/062757 dated Nov. 19, 2007, 8 pages.
International Search Report for International Application PCT/US2008/075316 dated Dec. 3, 2008, 2 pages.
International Search Report for International Application PCT/US2008/032540 dated Apr. 29, 2009, 3 pages.
International Preliminary Report on Patentability for International Application No. PCT/US2007/062757, mailed Aug. 26, 2009, 6 pages.
International Preliminary Report on Patentability for International Application No. PCT/US2008/075316, mailed Mar. 9, 2010, 7 pages.
Bergmann, et al, "Design and Calibration of Load Sensing Orthopaedic Implants," Journal of Biomechanical Engineering, Apr. 2008, vol. 130, 9 pages.
Catrysse, M., et al., "An Inductive Powering System with Integrated Bidirectional Datatransmission," Sensors and Actuators A: Physical, vol. 115, Issues 2-3, Sep. 21, 2004, pp. 221-229, The 17th European Conference on Solid-State Transducers.
Claes, L.E., and Cunningham, J.L., "Monitoring the Mechanical Properties of Healing Bone," Clin Orthop Relat res (2009) 467:1964-1971.
Kao-Shang Shih, et al, "Influence of Muscular Contractions on the Stress Analysis of Distal Femoral Interlocking Nailing," Clinical Biomechanics, 23 (2008) 38-44.
Westerhoff, P., "An Instrumented Implant for in vivo Measurement of Contact Forcdes and Contact Moments in the Shoulder Joint," Medical Engineering & Physics, 31 (2009) 207-213.
Swedberg, Claire, "Surgeon Designs System to Monitor Orthopaedic Implants and Promote Healing," RFID Journal, reprinted from http://www.rfidjournal.com/article/articleprint/3978/-1/1 on Mar. 26, 2008, 2 pages.
Rapp, Susan M., "Smart Implants to Provide Feedback, Measure Joint Loads, Detect Infection," Orthopedics Today, 2008, reprinted from http://www.orthosupersite.com/view.asp?rID=28657 on Jun. 6, 2008, 3 pages.
Seide, K., et al., "An Intelligent Internal Fixator System for Long Bones," 52nd Annual Meeting of the Orthopaedic Research Society, Paper No. 1698.
Rorie, J.F., et al, "A Telemetric Instrumentation System for Orthopaedic Implants," Apr. 19, 1995, 15 pages.
Arms, S.W., et al., "Wireless Strain Measurement Systems—Applications and Solutions," presented at NSF-ESF Joint Conference on Structural Health Monitoring, Strasbourg, France, Oct. 3-5, 2003.
Yang, G.Y., et al, "Design of Microfabricated Strain Gauge Array to Monitor Bone Deformation In Vitro and In Vivo," Proceedings of the Fourth IEEE Symposium on Bioinformatics and Bioengineering, May 19-21, 2004, 8 pages.
Einhorn, T.A., "The Cell and Molecular Biology of Fracture Healing," Clin Orthop, 1998: Suppl: 355:7-21.
Elvin, N., et al., "A Self-Powered Mechanical Strain Energy Sensor," Smart Matter Struct 2001; 10:1-7.
Kummer, F. J., et al., "Development of a Telemeterized Should Prosthesis," Clin Orthop Relat Res., Sep. 1996 (330):31-4.
Morris BA, D'lima, D.D , J., Kovacevic, N., Arms, S.W., Townsend, C.P., and Colwell, C.W. Jr., "e-Knee: Evolution of the Electronic Knee Prosthesis," J Bone Joint Surg., 83:62-66, 2000.
Kaufman, K., Irby, S.E., and Colwell, C.W., "Instrumented Implant for Measuring Tibiofemoral Forces," J. Biomechanics, 29:667-671, 1996.
Taylor, S.J.G., Walker, P.S., Perry, J.S., Cannon, S.R., and Woledge, R., "The Forces in the Distal Femur and the Knee During Walking and Other Activities Measured by Telemetry," The Journal of Arthroplasty, 13:428-437, 1998.
SRI Consulting, "RFID Technologies", 2004; and Silicon Chip Online, "RFID Tags—How They Work." reprinted from http://www.siliconchip.com.au/cms/A30750/article.html.
Global market for RFID in healthcare 2006-2016 by value: Source: IDTechEx, RFID in Healthcare 2006-2016.
Healthcare RFID Medical Microchip, Yenra, Apr. 30, 2003, reprinted from http://www.yenra.com/healthcare-rfid-medical-microchip/.
Verichip System, Product of VeriChip Corp., reprinted from http://www.verichipcorp.com/content/solutions/verichip reprinted on Apr. 26, 2011.
Sub-dermal RFID, Yenra, Sep. 25, 2003, reprinted from http://www.yenra.com/subdermalrfid/.

(56) References Cited

OTHER PUBLICATIONS

Clyde Church, "Radio Frequency Identification (RFID) Tracking of Orthopaedic Inventories Fact or Fiction, Today and Tomorrow," BONE Zone, Spring 2004, pp. 35-40.

Luis Figarella, Kirk Kikirekov, Heinrich Oehlmann, Radio Frequency Identification (RFID) in Health Care, Benefits, Limitations, Recommendations, A Health Industry Business Communications Council HIBCC White Paper (2006).

Alex Macario; Dean Morris; Sharon Morris "Initial Clinical Evaluation of a Handheld Device for Detecting Retained Surgical Gauze Sponges Using Radiofrequency Identification Technology" Arch Surg., 2006; 141:659-662.

Patricia Kaeding "RFID medical devices—Opportunities and challenges," Published Oct. 19, 2005, Wisconsin Technology Network, http://wistechnology.com.

Communication pursuant to Article 94(3) EPC for EPO Application No. 07717657.6, mailed Jul. 12, 2011, 4 pages.

First Office Action for Chinese Application No. 200680038574.1, mailed Oct. 9, 2009, 16 pages.

Second Office Action for Chinese Application No. 200680038574.1, mailed Jul. 7, 2011, 8 pages.

Japanese Notice of Reasons for Rejection for Application No. 2008-528223 mailed Nov. 1, 2011 (English translation), 3 pages.

Chinese Decision on Rejection for Chinese Patent Application 200680038574.1 issued Oct. 26, 2011 (English translation), 12 pages.

International Preliminary Report on Patentable for International Application No. PCT/US2006/033326, dated Feb. 26, 2008, 9 pages.

Written Opinion of the International Search Authority for International Application PCT/US2006/033326, mailed Feb. 23, 2008, 8 pages.

International Preliminary Report on Patentability for International Application No. PCT/US2009/032540, dated Aug. 3, 2010, 5 pages.

Written Opinion of the International Search Authority for International Application PCT/US2009/032540, dated Aug. 1, 2010, 4 pages.

Written Opinion of the International Search Authority for International Application PCT/US2008/075316, dated Mar. 6, 2010, 6 pages.

Notice of Allowance for U.S. Appl. No. 12/064,546, mailed Dec. 27, 2011, 8 pages.

Office Action for U.S. Appl. No. 11/718,588, mailed Dec. 8, 2010, 9 pages.

Final Office Action for U.S. Appl. No. 11/718,588, mailed May 5, 2011, 16 pages.

Office Action for U.S. Appl. No. 11/718,588, mailed Dec. 15, 2011, 17 pages.

International Search Report for International Application PCT/US2009/032540 dated Apr. 29, 2009, 3 pages.

Global market for RFID in healthcare 2006-2016 by value: Source: IDTechEx, RFID in Healthcare 2006-2016, May 1, 2006.

Office Action for U.S. Appl. No. 11/718,588, mailed Jul. 16, 2012.

Communication Pursuant to Article 94(3) EPC for European Application No. 07717657.6 mailed Jun. 21, 2010.

Communication Pursuant to Article 94(3) EPC for European Application No. 07717657.6 mailed Jun. 20, 2012.

Takeda, R., et al., "Gait Analysis Using Gravitational Acceleration Measured by Wearable Sensors," Journal of Biomechanics 42 (2009) 223-233.

Kavanaugh, J.J., et al., "Coordination of Head and Trunk Accelerations During Walking," Eur J Appl Physiol (2005) 94:468-475.

\* cited by examiner

PROCESSING SENSED ACCELEROMETER DATA FOR DETERMINATION OF BONE HEALING

CROSS-REFERENCE TO RELATED APPLICATIONS

This application is a U.S. National Phase filing of International Application No. PCT/US2007/062757. This prior application is herein incorporated by reference.

STATEMENT REGARDING FEDERALLY SPONSORED RESEARCH OR DEVELOPMENT

Not Applicable.

APPENDIX

Not Applicable.

BACKGROUND OF THE INVENTION

1. Field of the Invention

This invention relates generally to orthopaedic implants and, more particularly, orthopaedic implants having data acquisition capabilities.

2. Related Art

The trauma fixation implants currently available on the market are passive devices because their primary function is to support the patient's weight with an appropriate amount of stability whilst the surrounding fractured bone heals. Current methods of assessing the healing process, e.g. radiography, patient testimonial, etc., do not provide physicians with sufficient information to adequately assess the progress of healing, particularly in the early stages of healing. X-ray images can only show callus geometry and cannot be used to assess the mechanical properties of the consolidating bone. Therefore, it is difficult to quantify the load sharing between implant and bone during fracture healing from standard radiographs, CT, or MRI scans. Unfortunately, there is no in vivo data available quantifying the skeletal loads encountered during fracture healing as well as during different patient and physiotherapy activities.

There remains a need in the art for a system and method of assessing the healing process. It would be of significant benefit if the system and/or method could quantify the load sharing between an implant and a bone during fracture healing. Furthermore, it would be of significant benefit if the system could provide in vivo data to quantify the skeletal loads encountered during fracture healing. A clinician could use the assessment information provided by the system to counsel the patient on life-style changes or to prescribe therapeutic treatments if available. Continuous and accurate information from the implant during rehabilitation would help to optimize postoperative protocols for proper fracture healing and implant protection and add significant value in trauma therapy and reconstructive orthopedics. Furthermore, improvements in security and geometry (and speed) of fracture healing leads to significant economic and social benefits. Therefore, an opportunity exists to augment the primary function of orthopedic trauma and reconstructive implants to enhance the information available to clinicians.

SUMMARY OF THE INVENTION

In one aspect of the invention, there is provided a system for processing accelerometer data. The system includes an accelerometer, a first processor, a power supply, and a second processor. The accelerometer measures a physiological acceleration parameter. The first processor is operatively connected to the accelerometer. The first processor is configured to receive the acceleration parameter from the accelerometer and configured to output machine readable acceleration data. The machine readable acceleration data includes time domain accelerometer data. The power supply is electrically connected to the first processor. The second processor is configured to receive the machine readable acceleration data and transform the time domain accelerometer data into frequency domain accelerometer data.

In one embodiment, the accelerometer and the first processor are located within a medical implant. In yet another embodiment, the accelerometer and the first processor are located within a wearable device.

In one embodiment, an antenna is operatively connected to the first processor and the antenna is configured to transmit the acceleration data.

In another embodiment, the first processor and the second processor comprise one unit.

In yet another embodiment, the accelerometer and the first processor comprise one unit.

In another embodiment, the antenna and the power supply comprise one unit.

In one embodiment, the system further includes a reader for retrieving accelerometer data.

In yet another embodiment, at least one of the first processor and the second processor is part of a computer assisted surgery system.

In another embodiment, the antenna used to transmit the accelerometer data is also the inductive coupling element used to power the first processor and the accelerometer.

In still another embodiment, the power supply includes at least one of a capacitor, an inductive coupling, a battery, a mechanically driven power generation unit, a piezoelectric device, and an energy scavenging device.

In another embodiment, the first processor and accelerometer are powered by at least one of a capacitor, an inductive coupling, a battery, a mechanically driven power generation unit, a piezoelectric device, and an energy scavenging device.

In yet another embodiment, at least one of the machine readable acceleration data, the time domain acceleration data, and the frequency domain acceleration data is communicated under power from at least one of a capacitor, an inductive coupling, a battery, a mechanically driven power generation unit, a piezoelectric device, and an energy scavenging device.

In one particular embodiment, the second processor is part of a remote processing system. In some embodiments, the remote processing system has a display or sound generating unit.

In yet another aspect of the invention, there is provided a method of determining the healing progression status of a subject. The method includes the steps of: (a) collecting accelerometer data through use of an accelerometer operatively connected to the subject; (b) retrieving the collected accelerometer data, the accelerometer data having a time domain component; (c) transforming the time domain accelerometer data into frequency domain accelerometer data; and (d) analyzing the frequency domain accelerometer data for healing progression of the subject.

In one embodiment, the method further comprises wirelessly conveying accelerometer data to a remote processing system.

In another embodiment, the method further comprises communicating the analysis of the data to a user.

In yet another embodiment, the accelerometer data is taken while the subject is undergoing a predefined task. In some embodiments, the predefined task is ambulation. In other embodiments, the predefined task is performed preoperatively, intraoperatively, or postoperatively.

In still another aspect of the invention, there is provided a method of determining the healing progression status of a subject. The method includes the steps of: (a) attaching an accelerometer to a subject; (b) collecting accelerometer data through use of the accelerometer; and (c) analyzing the accelerometer data to determine if the subject has progressed in healing status.

In one embodiment, the step of attaching an accelerometer to a subject comprises installing a smart implant in the subject. A "smart implant" is an implant that is able to sense its environment, apply intelligence to determine whether action is required, and act on the sensed information to change something in a controlled, beneficial manner. In some embodiments, the smart implant is embedded with the accelerometer. In other embodiments, the accelerometer is located on an implant surface of the smart implant. The smart implant may be any number of devices, including a bone plate, a bone screw, a bone peg, a bone staple, an intramedullary nail, an intramedullary nail cap, an intramedullary nail/plate, an interference screw, a hip replacement stem, a hip replacement femoral neck, a hip replacement femoral head, a hip replacement acetabular liner, a hip replacement acetabular shell, a knee replacement tibial tray, a knee replacement tibial tray liner, a knee replacement femoral component, a knee replacement tibial tray shaft extension, a knee replacement patellar implants, a knee replacement wedges, a trochlear groove implant, a femoral canal restrictor, a shoulder replacement humeral stems, a shoulder replacement glenoid component, a shoulder replacement humeral head, an elbow replacement humeral component, an elbow replacement radial component, an elbow replacement ulnar component, an ankle replacement tibial component, an ankle replacement talar component.

In one particular embodiment, the smart implant is an intramedullary nail. In some embodiments, the intramedullary nail has a first end portion and a second end portion, and the accelerometer is located on the first end portion, the second end portion, or therebetween.

In yet another embodiment, the step of attaching an accelerometer to a subject comprises attaching a wearable device to the subject. In some embodiments, the wearable device is worn on at least one of the following a thigh, a distal femur, a proximal tibia, a distal tibia, an arm, a waist, a head, a wrist, a chest, embedded within a shoe, on a shoe, on a cast, and on a brace.

The advantage of the invention over the prior art concerns the incorporation of the components within the smart implant in a manner that protects the components, provides an accurate and stable connection between the sensor and its environment, maintains the functionality of the implant itself, and is suitable for large scale manufacture. The device allows for information to be gathered and processed yielding useful clinical data with respect to a patient's bone healing cascade.

The instrumented device removes the estimation from the conventional diagnostic techniques such as x-ray, CT and MRI imaging by providing the patient objective quantitative data collected from them through the healing process. Currently, there is no device which utilizes accelerometer data to monitor fracture healing. The device described within addresses this by having on board sensors and a memory facility enabling patient data to be stored thus allowing for early transmission of data. This data includes patient history and patient activity. The device also enables early intervention by the surgeon, if required, such as administration of drugs, injection of orthobiologics, cements or demineralized bone matrix to help promote/accelerate bone healing or a revision surgery.

There a number of other potential clinical benefits including reduced number of clinic visits, reduced pain suffered by the patient, improved data on fracture healing, and early notification of delayed or non-union.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate embodiments of the present invention and together with the description, serve to explain the principles of the invention. In the drawings.

DETAILED DESCRIPTION OF THE EMBODIMENTS

Figure 1:
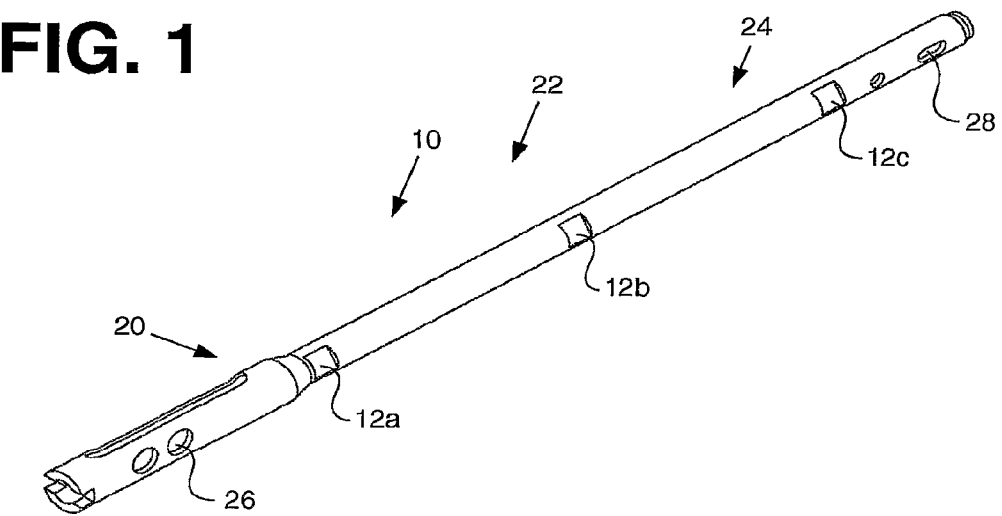
FIG. 1 is a perspective view of a telemetric orthopaedic implant in a first embodiment.
Figure 2:
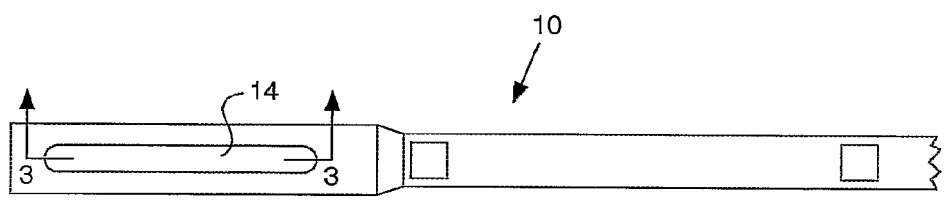
FIG. 2 is a top view of the implant shown in FIG. 1.
Figure 3:
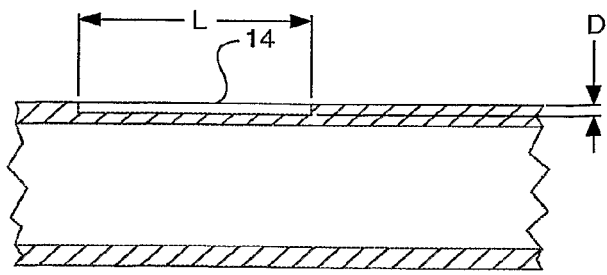
FIG. 3 is a partial sectional side view of the implant shown in FIG. 1.
Figure 4:
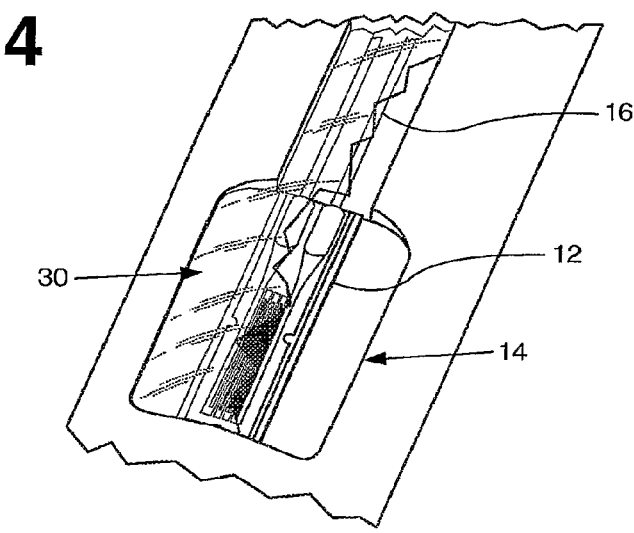
FIG. 4 is a detailed perspective view of the implant shown in FIG. 1.

A "smart implant" is an implant that is able to sense its environment, apply intelligence to determine whether action is required, and act on the sensed information to change something in a controlled, beneficial manner. One attractive application of smart implant technology is to measure loads on an orthopaedic implant. For example, an intramedullary nail is subjected to three types of loading: bending, torsional, and compression. These loads may be measured indirectly by measuring sensor output of a series of strain gauges mounted to the orthopaedic implant. In the case of an intramedullary nail, diametrically apposed strain gauges mounted on the outer surfaces of the nail are subjected to tensile and compressive forces, respectively. Typically, the strain measured from the sensors is higher when the implant is loaded in bending than in compression.

A fundamental parameter of the strain gauge is its sensitivity to strain, expressed quantitatively as the gauge factor (G). Gauge factor is defined as the ratio of fractional change in electrical resistance to the fractional change in length (strain), $$G = \frac{\Delta R}{R\varepsilon}, \tag{1}$$

where R=nominal resistance, ΔR=resulting change in resistance and ε=strain. This change in resistance arises from two important factors: (a) the change in the resistivity of the material, and (b) the change in the physical dimensions of the resistor as the material is deformed. For a foil strain gauge, G is found to be 2.1. Voltage recordings are converted to strain using the following equation:—

$$\varepsilon = \frac{-4V_r}{GF(1+2V_r)} x \left(1 + \frac{R_L}{R_g}\right) \tag{2}$$

where $R_L$ is the lead resistance, $R_g$ is the nominal gauge resistance, which is specified by the gauge manufacturer, GF is the Gauge Factor, which is also specified by the gauge manufacturer, and $V_r$ is the voltage ratio defined by the following equation:—

$$V_r = \left(\frac{V_{CH}(\text{strained}) - V_{CH}(\text{unstrained})}{V_{EX}}\right) \tag{3}$$

where $V_{CH}$ and $V_{EX}$ are the measured signal's voltage and excitation voltage respectively.

Strain is related to stress using Hooke's Law which can be rearranged to calculate the compression and bending loads experienced by the implant (F), $$F = E \cdot \varepsilon \cdot A, \tag{4}$$

where E is the stiffness of the implant in gigapascals (GPa), ε=strain measured from the output of the instrumented implant, and A is the cross-sectional area of the implant in square meters (m$^2$). The corresponding load on the bone is deduced by subtracting the implant load from the total downward force exerted by the limb measured using either a force plate or a balance.

Incorporation of sensors and other electronic components within an implantable medical device, such as an intramedullary nail, alters its primary function from a passive load-supporting device to a smart "intelligent" system with the ability to record and monitor patient activity and compliance.

Telemetric Intramedullary Nail

Referring to the accompanying drawings in which like reference numbers indicate like elements, FIG. 1 illustrates a telemetric intramedullary (IM) nail 10. The telemetric IM nail 10 includes at least one sensor 12. One particular sensor configuration is illustrated in FIG. 1. In this embodiment, sensors 12 are located in a proximal region 20, a central or mid-shaft region 22, and a distal region 24 of the IM nail 10. In the embodiment depicted in FIG. 1, the telemetric IM nail 10 includes three sensors 12a, 12b, 12c with a sensor corresponding to each region. However, those of ordinary skill in the art would understand that a greater or lesser number of sensors may be used and that sensors may be applied in other configurations. The telemetric nail 10 continuously measures a set of strain values generated from the sensors 12. As explained in greater detail below, the telemetric IM nail 10 transmits the measurements from the nail to a reader device for calculation of the forces components without disturbing fracture healing.

The telemetric IM nail 10 may include features to allow fixation of the nail to bone. For example, the telemetric IM nail 10 may include proximal apertures 26 and/or distal apertures 28. In the embodiment depicted in FIG. 1, the telemetric IM nail 10 includes two proximal holes 26, a distal hole 28, and a distal slot 28, but those of ordinary skill in the art would understand that a greater or lesser number of apertures may be provided.

Figure 5:
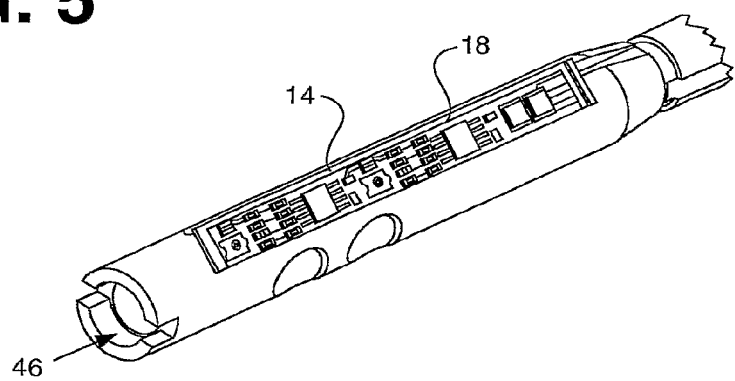
FIG. 5 is a perspective view of a telemetric orthopaedic implant in a second embodiment.

As best seen in FIG. 5, the telemetric IM nail 10 also includes one or more electronic components 18, such as a printed circuit board. The electronic components 18 form an instrumentation circuit with the sensors 12. The electronic components 18 may include associated signal conditioning circuitry, one or more microprocessors, one or more memory devices, a power supply, and communications components. The electronic components 18 allow in situ measurement of changes in the local environment. The combination of the sensor 12 and the electronic components 18 provide a powerful tool for indirect measurement of the changing load over time due to fracture consolidation using the algorithm described above. In turn, these indirect measurements may be used to provide information to clinicians on the environment for use in clinical decision making.

In order to maintain the integrity of the telemetric IM nail 10, the implant design must protect the components, provide an accurate and stable connection between the sensor and its environment, and maintain the functionality of the implant itself. Incorporating sensors within the structure of internal implants raises the "packaging problem" of maintaining the insulation of electronics, as biological tissues are an extremely hostile environment. Furthermore, the risk of damage to the electronic components 18 from common sterilization methods cannot be underestimated. Design considerations for instrumenting the IM nail 10 requires minimization of any damage to the mechanical and physical properties of the nail and allow for large scale commercialization and manufacture. Certain designs may be confirmed by measuring the bending stiffness and fatigue behavior of the IM nail 10 before and after instrumentation.

As best seen in FIGS. 2-5, the IM nail 10 includes at least one recess 14. As examples, the recess 14 may be rectangular, square, circular, elliptical, or some combination thereof. The recess 14 may be made using various manufacturing techniques including, but not limited to machining, milling, grinding, forging, casting, stamping, and injection molding. The recess 14 has a depth D, which ranges from about 0.1 mm to about 9.0 mm. The length L of the recess may be in the range from about 1 mm to about 100 mm. In the embodiment depicted in FIG. 3, the recess 14 is about 0.5 mm thick and about 5 mm long. The recess 14 receives the sensor 12 and conductor wires 16. The recess 14 protects the sensor 12 and conductor wires 16 from abrasive damage during the surgical insertion process. The recess 14 is located on either an anterior surface or a posterior surface enabling the sensors 12 to experience tensile and compression forces respectively. The sensor 12 may be fixed in the recess 14 using a range of high stiffness adhesives including epoxy resins, polyurethanes, UV curable adhesives, and medical grade cyanoacrylates. These types of fixation methods do not adversely affect the performance of the sensor 12.

Additionally, the telemetric IM nail 10 may include a recess 14 in the proximal region 20 to receive the electronic components 18. The recess 14 is dimensioned to accept the electronic components 18. For example, the electronic components may be about 56 mm long, about 6.2 mm wide, and about 0.25 mm thick, and the recess 14 is sized accordingly. The recess 14 may be of the same size as the electronic components 18 or slightly larger.

Alternatively, installation of the strain gauges 12 and other electronic components may be carried out using a more evasive method, such as electro-discharge milling a longitudinal section in the implant, installing the components in the IM nail 10, and laser welding the tube segments. However, there are several disadvantages to using this approach. Localized heat of welding tends to cause distortion and warping of the base metals or stresses around the weld area, which could affect the corrosion resistance of the implant. Moreover, laser beam welding has a tremendous temperature differential between the molten metal and the base metal immediately adjacent to the weld. Heating and cooling rates are much higher in laser beam welding than in arc welding, and the heat-affected zones are much smaller. Rapid cooling rates can create problems such as cracking in high carbon steels.

There are a number of ways to encapsulate the sensors 12 and other electronic components. Some components may require more durable methods of encapsulation than others. For example, if a battery or other potentially hazardous device is included in the electronics system a titanium case may be required. Alternatively, if the components are biologically benign, then a simple potting material, such as polyurethane or a silicone, may prove to be sufficient. Those skilled in the art would understand that various materials may be used for the potting material. What is significant is that the potting material acts as a cover to separate the electronic components from the surrounding environment. Soldering and welding techniques may also be used to help permanently seal the sensors 12 and other electronic components inside the instrumented nail 10. Substituting the standard foil gauge with platinum strain gauges may also enhance durability and resistance to sterilization and attack by biological fluids.

Figure 6:
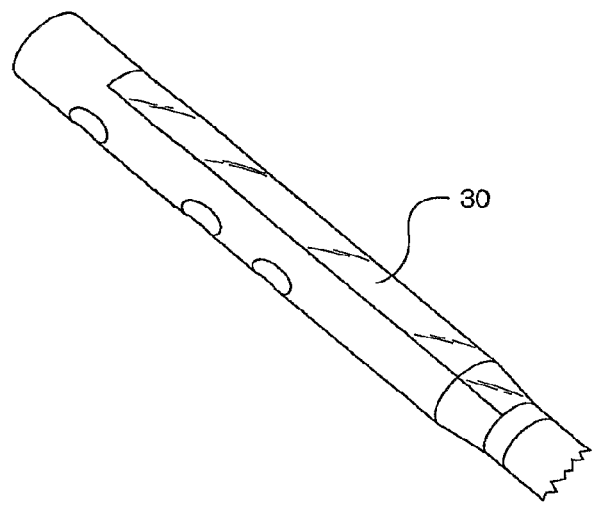
FIG. 6 is a perspective view of the telemetric orthopaedic implant shown in FIG. 5.

In one particular embodiment in FIG. 6, the sensors 12 and the electronic components 18 are covered with a biocompatible potting material 30, such as polyurethane or silicone, in order to provide a hermetic seal. Because the sensors 12 and the electronic components 18 are sealed hermetically from the patient tissues and fluids, long term function of the telemetric IM nail 10 is achievable. At the same time, leakage of non-biocompatible or toxic materials is eliminated. The potting material 30 is an electrically insulative, moisture resistant material, supplied in either a liquid or putty-like form and is used as a protective coating on sensitive areas of electrical and electronic equipment. The potting material 30 may be optically opaque or colorless. The strain gauges 12 and conductor wires 16 are covered in potting material 30 with suitable mechanical characteristics required to survive the implantation process and restore the mechanical envelope.

Figure 7:
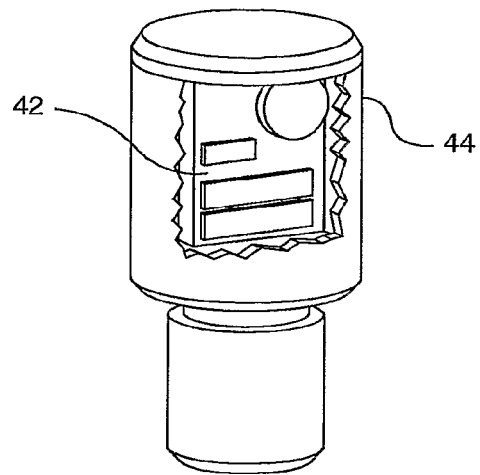
FIG. 7 is a perspective view of an insert.
Figure 8:
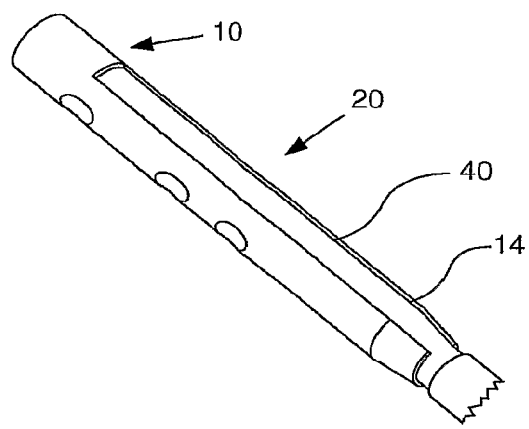
FIG. 8 is a perspective view of a telemetric orthopaedic implant in a third embodiment.
Figure 9:
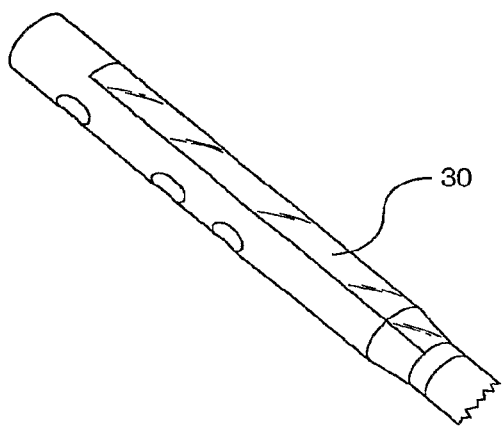
FIG. 9 is a perspective view of the telemetric orthopaedic implant shown in FIG. 8.

An alternative arrangement of the electronic components 18 in the telemetric instrumented nail 10 is shown in FIGS. 7, 8, and 9. In this particular design, passive electronic components 40 are located in the recess 14 of the proximal region 20 and active electronic components 42, such as a power supply, microprocessor, data storage device, and external communication device, are contained in a separate nail head insert 44. As best seen in FIG. 9, the passive electronic components 40 may be covered with the potting material 30 to hermetically seal the electronic components 40. In this configuration, the telemetric IM nail 10 is implanted in the usual manner, and, once the nail has been implanted into the bone, the nail head insert 44 is attached to the telemetric IM nail 10. For example, the nail head insert 44 may be threaded into a hole 46 (best seen in FIG. 5). This particular design avoids any sensitive electronics being damaged by the implantation process. Connections between the passive and active electronic components 40, 42 are made using either an inductively coupled link or physical connections via slip rings.

The telemetric IM nail 10 may be constructed from a biocompatible material using standard manufacturing techniques. For example, the nail may be forged out of metal, hand or machine laid composite, or machined from stock. Alternatively, the telemetric IM nail 10 may be cast, injection molded, or compacted through hot isostatic processing (HIP). The HIP manufacturing process is particularly suited for producing nails with preformed recesses designed to receive sensors and electronic components.

In yet another alternative embodiment, the telemetric IM nail 10 may be constructed using a biodegradable composite whose degradation rate is controlled by sensed strain data. Such a device is more compliant than a conventional metal implant because the mechanical modulus of the implant changes according to the degree of healing of the adjacent bone. Increased load bearing capacity on the healing bone triggers the release of an active agent that accelerates the degradation rate of the nail in order to reduce its load sharing ability. On the other hand, slow healers require the release of active agents that inhibit the degradation rate of the implant material. The release of the active agent may be controlled using a micro-electromechanical structures (MEMS) reservoir system that releases a chemical manipulation on demand that either accelerates or decelerates the rate of degradation of the nail. The instrumented components may be manufactured using restorable materials, such as degradable, porous silicon wafers. Otherwise, non-degradable electronic components may remain in the patient, which may be acceptable in some cases.

Figure 10:
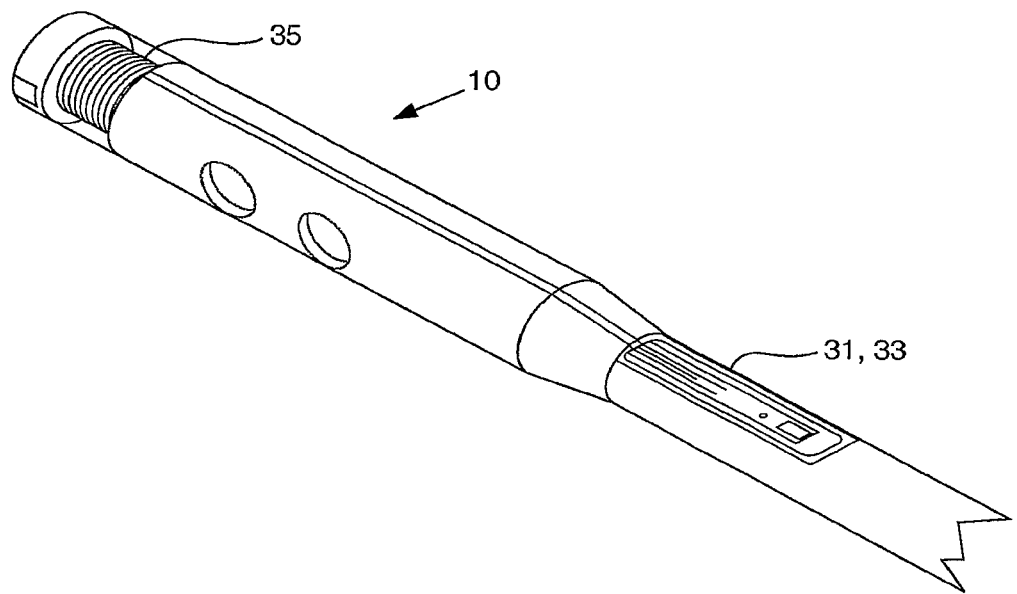
FIG. 10 is a perspective view of a telemetric orthopaedic implant in a fourth embodiment.
Figure 11:
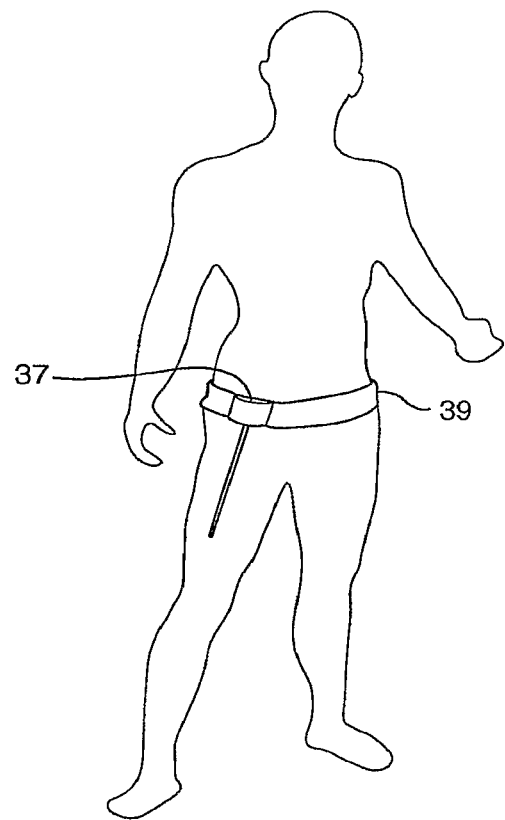
FIG. 11 is a perspective view of an external reader as mounted on a belt.

FIGS. 10 and 11 illustrate one particular embodiment of the telemetric IM nail 10. The telemetric IM nail 10 includes a single foil strain gauge 31, a printed circuit board 33, and a driver coil 35. In some embodiments, the printed circuit board 33 includes a microprocessor (not shown) and an oscillator (not shown). At least some of these components may be placed within a machined cavity located on the telemetric IM nail 10 and covered with a biocompatible potting material. In the depicted embodiment, the telemetric IM nail 10 is a femoral antegrade nail and the strain gauge is located on the anterior "tensile loaded" surface of the nail. The telemetric IM nail 10 may include a low power telemetry system that is only activated when the telemetric IM nail 10 is within an interrogation zone of an external reader or interrogator 37. The transmission of power across an air gap is achieved using magnetic fields generated by inductive couple power transfer. The air gap is in the range of about 30 mm to about 110 mm, with a particularly suitable range from about 60 mm to about 80 mm. The strain gauge produces a measurable effect in the reader coil from which strain can be determined. When the telemetric IM nail 10 is not being read, it is in "sleep" mode.

As best seen in FIG. 11, the interrogator 37 is a belt 39 worn by the subject around the waist during data acquisition. The belt 39 may be worn at the subject's residence or at a clinic or other healthcare facility. The data may be transmitted by wire or wirelessly to a computing device, such as a personal computer, laptop, personal data assistant, or the like.

As an example of use, the telemetric IM nail 10 and the belt may be used to capture strain data. By analyzing the data, a user can determine the healing status or progression of the subject. The data may include, as an example only, the maximum strain recorded over a period of time, such as several months. The entire healing period may be six months or more depending upon the healing progression of the subject. In the case of the strain gauge, the load component of the healing bone can be determined by subtracting the implant load from the total load measured in the operated limb. The strain rate measurements may be used to estimate the degree of healing. Moreover, the strain rate measurements may provide insight into the stiffness of the healing bone for various activity levels specific to the subject and type of injury. The inductive couple power transfer enables the healing status of the implant to be monitored for the entire lifetime of the subject. Thus, the user may look many years later for changes in the implant as a result of old-age, trauma, or disease. While the depicted embodiments relate to intramedullary nails, those of ordinary skill in the art would understand that the invention is also well suited for joint replacement applications.

FE Modeling to Determine Optimum Position of Sensors

Figure 12:
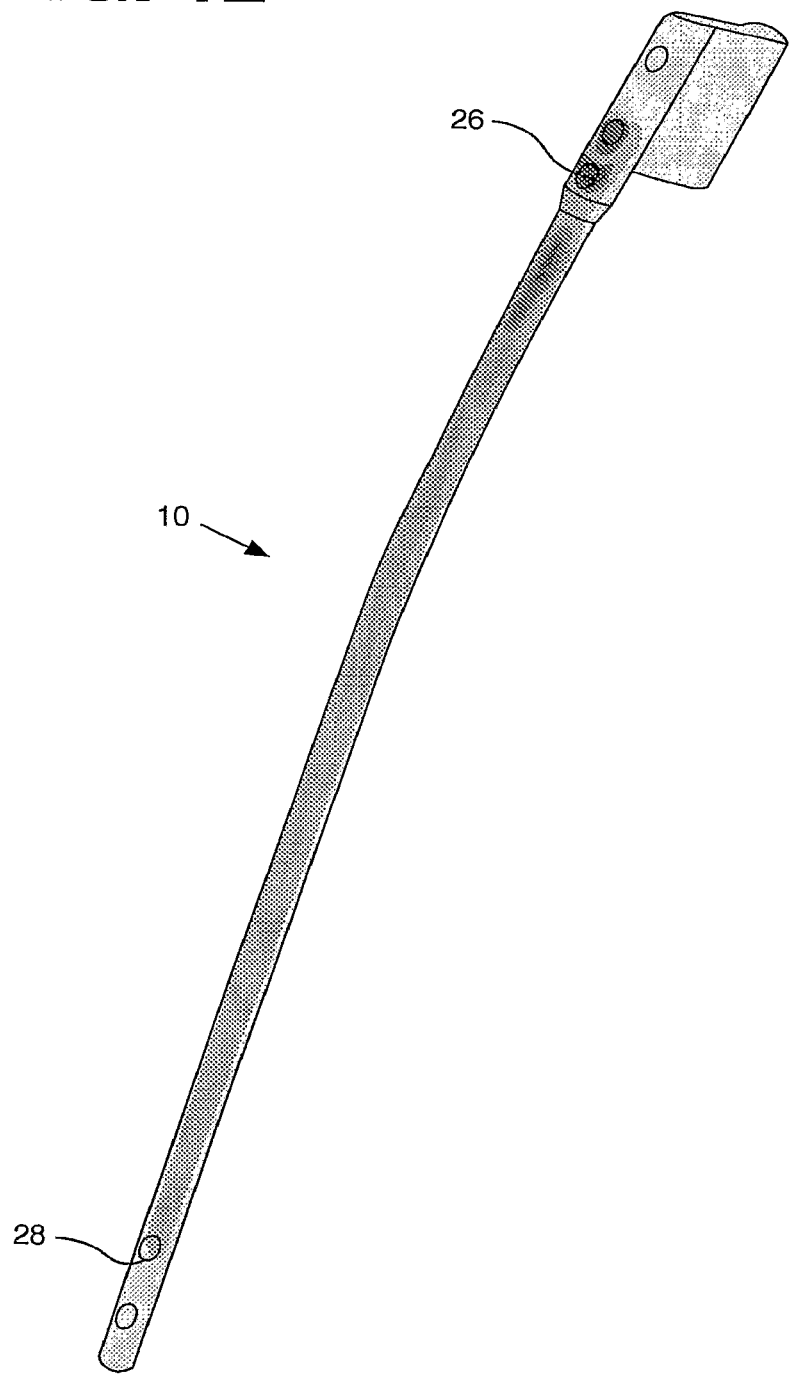
FIG. 12 is a perspective view of a telemetric orthopaedic implant illustrating the results of finite element analysis.

Referring now to FIG. 12, the sensors 12 may be devices capable of measuring mechanical strain, such as foil or semiconductor strain gauges. Alternatively, the sensors 12 may be load cells used to directly measure mechanical load. The embodiment depicted in FIG. 1 utilizes foil strain gauges to measure strain. The optimum location of the sensors 12 for the purpose of measuring strain may be determined through finite element (FE) analysis. The sensors 12 may be located, for example, but not limited to, in the working region of the implant 10. The working region is defined as the region between two fixation apertures 26, 28. The fixation apertures 26, 28 are adapted to receive fasteners, such as screws, to attach the implant 10 to bone. As can be seen in FIG. 10, the darker, shaded areas represent stress concentrations. The stress distribution results from the way in which the nail 10 is loaded through the patient's hip joint and results in high bending stresses on the outer surface of the nail 10, aligned with the proximal apertures 26. Typically, a 50% reduction in stress is observed between sensors placed inside the implant as opposed to an external mounting.

Sensor

The telemetric IM nail 10 includes the sensor 12. The sensor 12 senses at least one item, event, condition, etc. The sensor 12 may be any number of types including, but not limited to, a foil strain gauge, a semi-conductor strain gauge, a vibrating beam sensor, a force sensor, a piezoelectric element, a fiber Bragg grating, a gyrocompass, or a giant magneto-impedance (GMI) sensor. Further, the sensor 12 may indicate any kind of condition including, but not limited to, strain, pH, temperature, pressure, displacement, flow, acceleration, direction, acoustic emissions, voltage, pulse, biomarker indications, such as a specific protein indications, chemical presence, such as by an oxygen detector, by an oxygen potential detector, or by a carbon dioxide detector, a metabolic activity, or biologic indications to indicate the presence of white blood cells, red blood cell, platelets, osteoblasts, osteoclasts, growth factors, or collagens. Finally, the sensor 12 may be an image capturing device.

Some orthopaedic applications may require more than one sensor to measure more than one item, event, or condition. Thus, some implants require multi-channel capabilities. For example, the telemetric IM nail 10 may include six or more strain gauges. The sensor 12 may be an array of sensors or a series of discrete sensors. The telemetric IM nail 10 also may be designed with multi-axial strain gauges in a rosette configuration to allow for the measurement of loads in x, y and/or z planes. The configuration of the sensors 12 also may be tailored to meet the requirements of the patients fracture. The sensor 12 is designed in such way that it does not compromise the performance of the implant. For example, the sensor 12 must be unobtrusive, biocompatible, and in no way affect the established biomechanical performance of the implant. It has been shown that nails with a tight fit between implant and the adjacent bone may be deformed significantly during insertion. As a result, the resolution of the selected sensor is better than 8 bit (0.05%). The output of the sensor may be investigated by applying an axial load to the instrumented nail.

Figure 13:
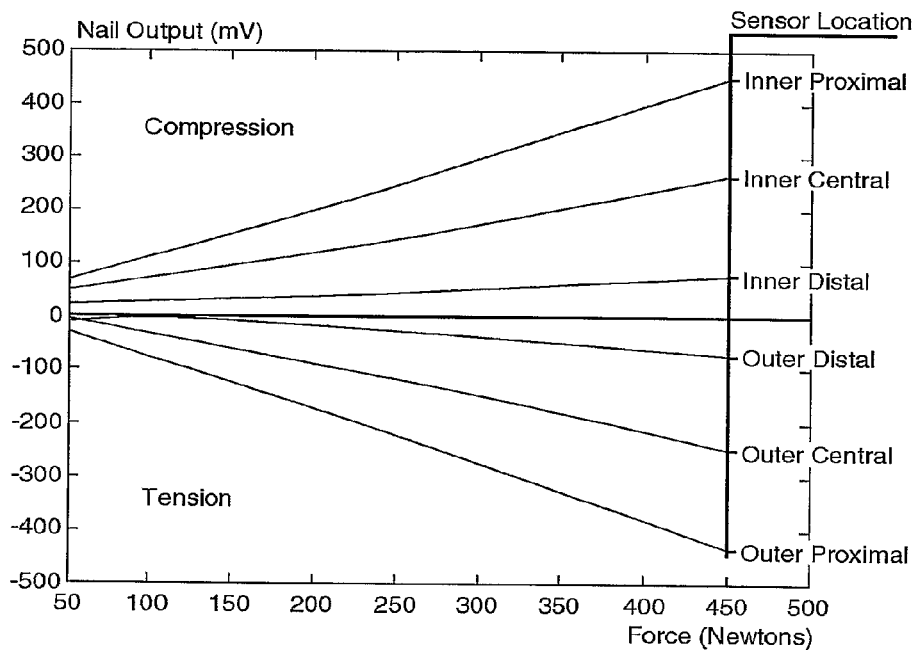
FIG. 13 is a graph illustrating data output vs. force.

The loading configuration is designed to match the loading pattern typically observed in a human femur, i.e. an offset vertical load transmitted through the nail via the proximal fastener. Strain vs. load plots for three instrumented IM nails with two strain sensors 12 located on the inner (compression) and outer (tensile) surfaces at either the mid-shaft region (nail 1), distal region (nail 2), or proximal region (nail 3) respectively are shown in FIG. 13. In all cases, the responses from the sensor pairs are fairly linear when the load on the nail is ramped up to 500 N. In addition, there is little or no hysteresis observed when the load is applied and removed from the nail.

As noted above, the sensor 12 may be an accelerometer, obtaining nearly continuous changes in acceleration over time at a sampling rate from about 0.5 Hz to about 2000 Hz. The system also may be designed with multi-axial accelerometers in varying configurations to enable changes in acceleration measurement in x, y and z planes. The accelerometer embedded into the IM is designed in such way that it does not compromise the performance of the implant, i.e. unobtrusive, biocompatible, and in no way affect the established biomechanical performance.

The sensors may be any combination of devices capable of measuring raw acceleration or change in relative acceleration of the implant, patient extremity, any portion of the patient's body, cast, brace, splint, or boot. In the current invention the sensor could be MEMS (micro-electromechanical system) or non-MEMS based accelerometer in a cantilever beam configuration or other relevant configuration (spring-mass-damper), gravimeter, vibrating beam, and/or gyroscope. The sensor could be analog or digital with any numbers of axes including a maximum swing of ±50 g. The sensitivity of the sensor is sufficient to capture the acceleration data such that when amplified the data is recognizable and discernable (e.g. 0.0001-100 mV/g). The sensor bandwidth is suitable to ensure proper data generation and capture (e.g. 0.01-20000 Hz). Further, the operating temperature of the sensor allows for implantation as well as ambient conditions if the sensor is being worn. An acceptable operating temperature range is −50-150 degrees F.

Communication

The electronic components 18 are in communication with a data receiver 50. The electronic components 18 receive data from the sensor 12 and transmit the data to the data receiver 50. The electronic components 18 transmit the data by wire or through a wireless connection. The transmission may use available technologies, such as ZIGBEE™, BLUETOOTH™, Matrix technology developed by The Technology Partnership Plc. (TTP), or other Radio Frequency (RF) technology. ZigBee is a published specification set of high level communication protocols designed for wireless personal area networks (WPANs). The ZIGBEE trademark is owned by ZigBee Alliance Corp., 2400 Camino Ramon, Suite 375, San Ramon, Calif., U.S.A. 94583. Bluetooth is a technical industry standard that facilitates short range communication between wireless devices. The BLUETOOTH trademark is owned by Bluetooth Sig, Inc., 500 108th Avenue NE, Suite 250, Bellevue Wash., U.S.A. 98004. RF is a wireless communication technology using electromagnetic waves to transmit and receive data using a signal above approximately 0.1 MHz in frequency. Due to size and power consumption constraints, the telemetric IM nail 10 may utilize the Medical Implantable Communications Service (MICS) in order to meet certain international standards for communication.

Instrumentation System

Figure 14:
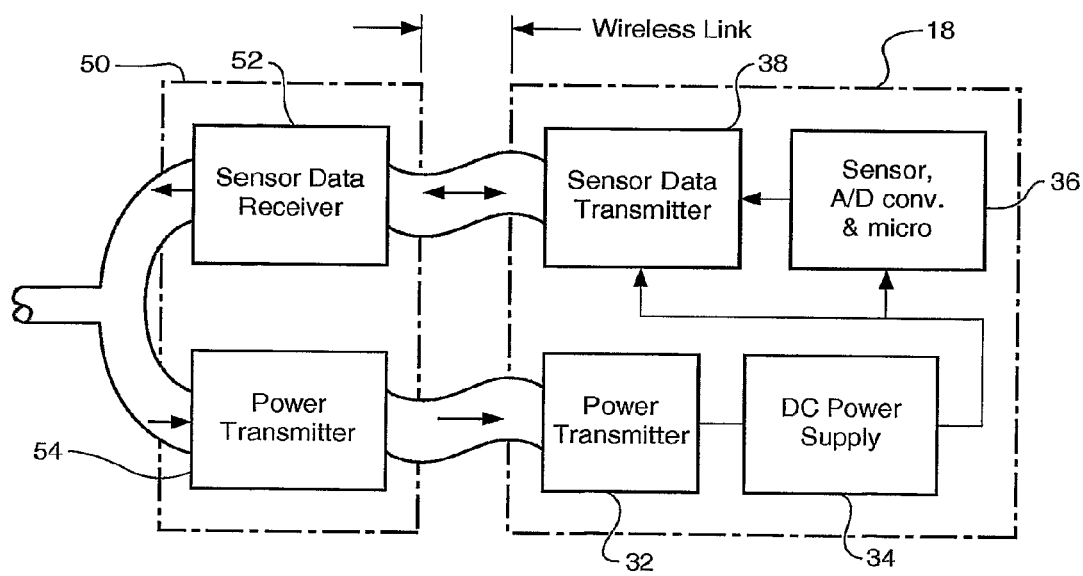
FIG. 14 is a schematic illustrating an electronic component and a data receiver.

FIG. 14 illustrates the electronic components 18, such as a printed circuit board, and the data receiver 50. The electronic component 18 includes a power transmitter 32, a DC power supply 34, a combination analog/digital converter and microprocessor 36, and a sensor data transmitter 38. The data receiver 50 includes a sensor data receiver 52 and a power transmitter 54. Although illustrated as separate components, those of ordinary skill in the art would understand that the transmitter and the receiver may be combined in a single unit, sometimes referred to as a transceiver. In the embodiment depicted in FIG. 14, power consumption and data transmission are contactless. The electronic component 18 may include any of the following: (1) any number of foil strain gauges; (2) matching number of low noise, low power instrumentation amplifiers; (3) matching number of Wheatstone bridge resistor networks; (4) matching number of strain gauge zero-adjustments; and (5) onboard power supply with noise filtering.

One particular arrangement of the system architecture is illustrated in FIG. 14. In this particular example, power consumption and data transmission are contactless.

The circuitry is designed to fit within the nail and provide either a wired or wireless interface with the onboard sensors, and allow low-noise measurements.

Power Management

The telemetric IM nail 10 may incorporate one or more power management strategies. Power management strategies may include implanted power sources or inductive power sources. Implanted power sources may be something simple, such as a battery, or something more complex, such as energy scavenging devices. Energy scavenging devices may include motion powered piezoelectric or electromagnetic generators and associated charge storage devices. Inductive power sources include inductive coupling systems and Radio Frequency (RF) electromagnetic fields.

Finally, the telemetric IM nail 10 may incorporate a storage device (not shown). The storage device may be charged by an inductive/RF coupling or by an internal energy scavenging device. The storage device must have sufficient capacity to store enough energy at least to perform a single shot measurement and to subsequently process and communicate the result.

Figure 15:
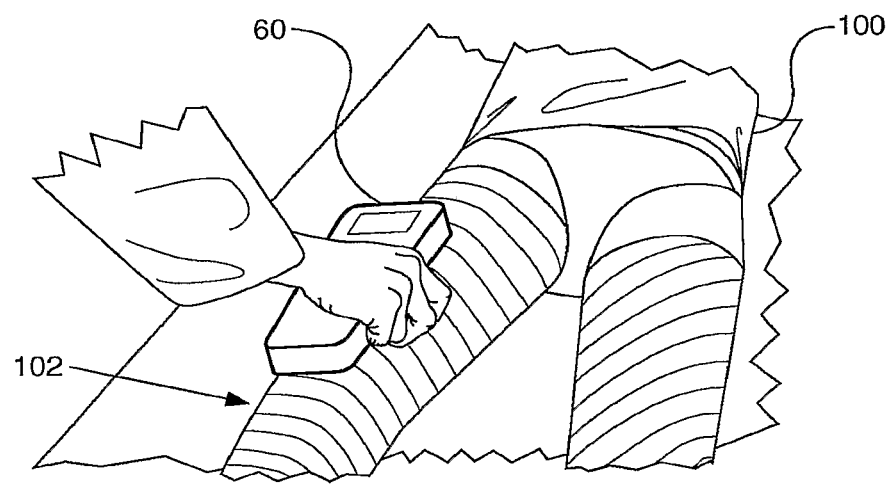
FIG. 15 illustrates use of a handheld device.
Figure 16:
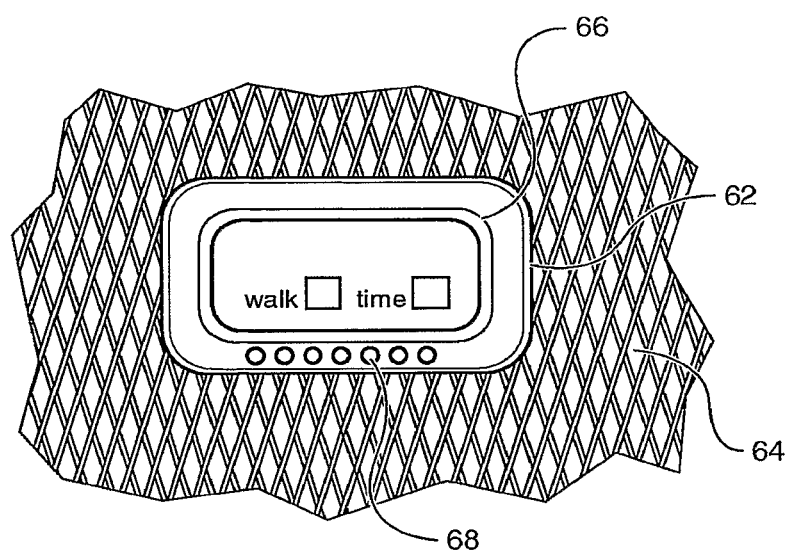
FIG. 16 illustrates a control unit.

FIG. 15 illustrates a handheld device 60 being placed on a leg 102 of a patient 100. The handheld device 60 generates RF waves that excite the electronic component 18. The excited electronic component 18 retrieves stored sensor readings and sends them to the handheld device 60 via a carrier wave. The handheld device 60 may be equipped with a processor (not shown) for direct analysis of the sensor readings or the handheld device 60 may be connected to a computer for analysis of the sensor readings.

Communication

The demands on an implantable telemetry system are severe and robust methods must be utilized to capture data from the orthopaedic implant. Prior attempts in the art have not provided a signal in the range needed for an instrumented intramedullary nail. Thus, the telemetric IM nail 10 has a wired interface in its most simplified version. In other words, the electronic components 18 are connected to an external control unit 62 via a wire (not shown). The control unit 62 may be placed on the patient 100 as a wearable device, such as an arm band, wrist band, thigh band, or anklet bracelet. Alternatively, the control unit 62 may be connected to a cast 64, such as by placing the control unit inside the cast or attaching the control unit to the exterior of the cast.

The control unit 62 may include a display 66 and/or a speaker 68. The display 66 may be used to display sensor readings, provide warning lights, a count down timer allowing the patient to anticipate an important event, such as cast removal, or an entertainment device, such as an electronic game, to occupy time. The speaker 68 may be used to provide sounds, such as pre-recorded instruction, warning sounds, or game sounds.

The patient actively wears the control unit 62 which constantly monitors the patient's activity. In the case of a major event, such as a traumatic incident or loss of essential body function, the control unit 62 senses this change and sends out an alert which could be audible and/or visual. Alternatively or in addition to the alert, the control unit 62 may send information to another device which could prompt the wearer for information to confirm the patient's status. The control unit 62 also could be used to notify emergency assistance groups of impending danger and other pertinent information, such as location of the patient. In this last example, the control unit 62 may include a global positioning system (GPS) module to locate the control unit and patient.

The control unit 62 may be housed in virtually any type of material, such as plastic, rubber, metal, glass, ceramic, wood, stone, long fiber composites, short fiber composites, non-fiber composites, etc. The display 66 may be a liquid crystal display, a light emitting diode display, a plasma display, a digital light processing, a liquid crystal on silicon display, cathode ray tube, etc.

In other embodiments, however, the telemetric IM nail 10 has a wireless communications facility to allow the patient to move around freely. This embodiment is partially depicted in FIG. 14.

In some embodiments, the sensor is a separate entity from the control unit. This sensor is worn or otherwise attached to the outside of the patient's body or integrated in some fashion into the implant. In any case, the control unit could be placed on the body as a wearable device (arm band, wrist band, thigh band, anklet) or placed inside or attached to a plaster cast. Alternatively, the control unit may be an integral part of the implant.

Figure 17:
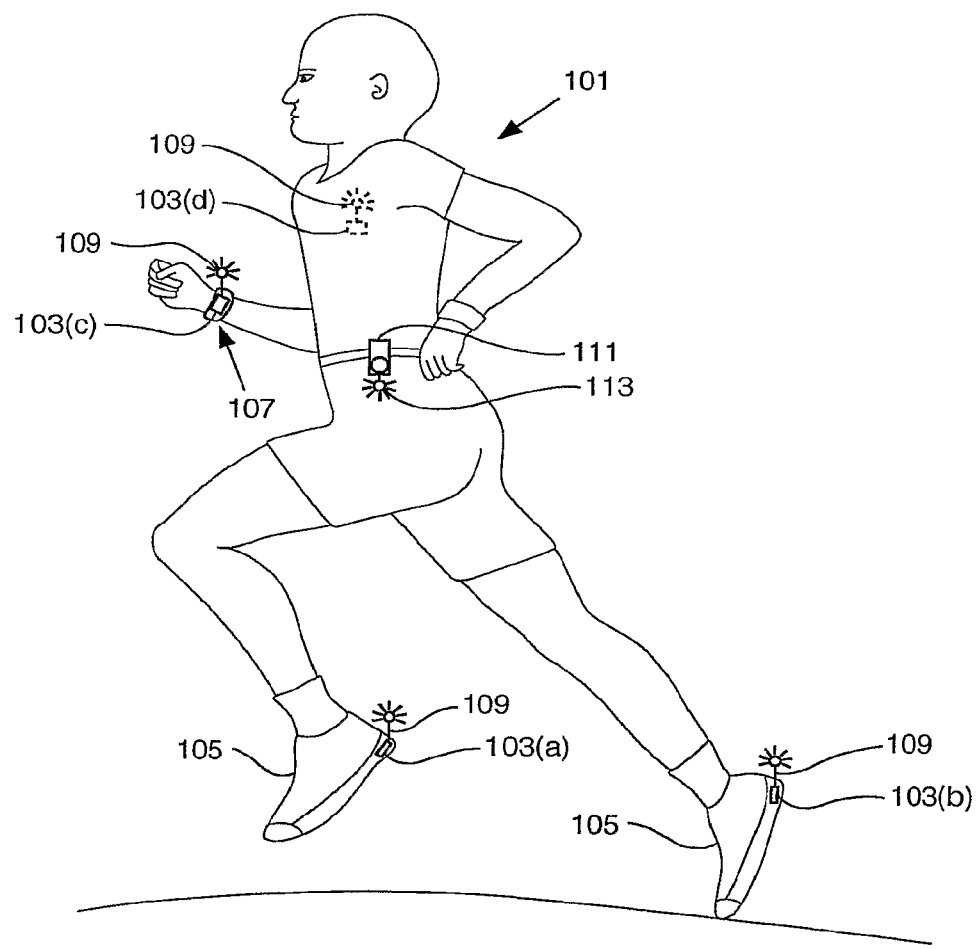
FIG. 17 is a schematic illustrating a wearable device.

FIG. 17 illustrates a system having a separate sensor and control unit. As shown in FIG. 17, a person 101 may have one or more sensing devices 103(*a*), 103(*b*), 103(*c*), and 103(*d*) included on their person, their clothing, their footwear, or their equipment. These sensing devices may sense data, such as physical or physiological data associated with the person. As some more specific examples, in the environment illustrated in FIG. 17, sensors 103(*a*) and/or 103(*b*) may sense step count (e.g., for pedometer type speed and/or distance measuring), GPS data, step impact force data, jump height data, or the like; sensor 103(*c*) may sense pulse rate, body temperature, blood pressure, hydration levels, or the like; and sensor 103(*d*) may sense heart rate, EKG data, and the like. Those having ordinary skill in the art would understand any number of sensors may be provided. Additional examples of potential types of data that may be collected include, but are not limited to: user speed data; user distance data; altitude data; route data; contact surface impact force data; ambient temperature data; ambient humidity data; barometric pressure data; sole member compression data; body temperature data; hydration level data; air intake rate or volume data; air expel rate or volume data; EEG data; blood gas content data; and the like.

The various sensors, e.g., 103(*a*) through 103(*d*), also may be portable and carried by the person 101 in any desired manner without departing from the invention. For example, if desired, one or more sensors may be mounted in or on an article of footwear 104 (e.g., like sensors 103(*a*) and 103(*b*) in this example) or provided in or on an article of athletic apparel (e.g., like arm band 106 in this example, which includes sensor 103(*c*), in a shirt, shorts, pants, socks, headband, etc.). As still additional examples, as illustrated in FIG. 17, a sensing device 103(*d*) may be mounted directly on the athlete's 101 body, e.g., by adhesives, bands, hooks, other mechanical connectors, or the like.

The sensing systems and/or devices 103(*a*) through 103(*d*), as well as any data transfer systems associated therewith (e.g., such as wireless transmission or transceiver devices 109 shown in FIG. 17 and described more below (e.g., radio transceivers)), may be mounted on articles of footwear, clothing, athletic equipment, or the like in any desired manner, e.g., via clips, clamps, adhesives, sewing, in pockets, via hook-and-loop fasteners, or other fasteners or mechanical structures, etc. Alternatively, if desired, the sensing systems or devices 103(*a*) through 103(*d*) may be integrally formed with and/or included as part of an article of footwear or an article of clothing without departing from the invention. If desired, one or more sensing devices and its/their associated data transfer system(s) 109 may be included as part of a single structure, e.g., mounted in a common housing and/or on a common board, connected to one another, etc., without departing from this invention. Further, if desired, the housing (if any) may be equipped with operation lights (e.g., LEDs, etc.) or other indicators, e.g., to indicate power status (e.g., on/off), power source status (e.g., charging v. battery operation), data reception and/or processing status (e.g., standby v. receiving v. transmitting v. processing, etc.), charge or recharging level status, etc.

Physical or physiological data associated with the subject may be collected by the various sensing devices (e.g., devices 103(*a*) through 103(*d*)) and transmitted to a display device 111 for display (and optionally storage, further processing, etc.). Any type of display device 111 may be used without departing from the invention, including, for example, conventional or "off the shelf" display devices 111. More specific examples of suitable display devices 111 include: electronic devices with a display screen, such as an LED, LCD, or plasma display screen; watches; portable audio devices, such as radios, tape players, CD players, MP3 players, and the like; alphanumeric display devices such as beepers, pagers, and the like; portable video or audio/video display devices, such as portable televisions, DVD players, and the like; portable communication devices, such as cellular telephones, radios, and the like; portable computing systems, such as PDAs, handtop or palm top computing systems, and the like. In the illustrated example, the display device 110 includes a cellular telephone that the user has clipped to his belt so as to be readily carried and used during ambulation. In some embodiments, the display device 111 is replaced with an audio signaling device. In other embodiment, the display device 111 includes an audio signaling device.

Figure 18:
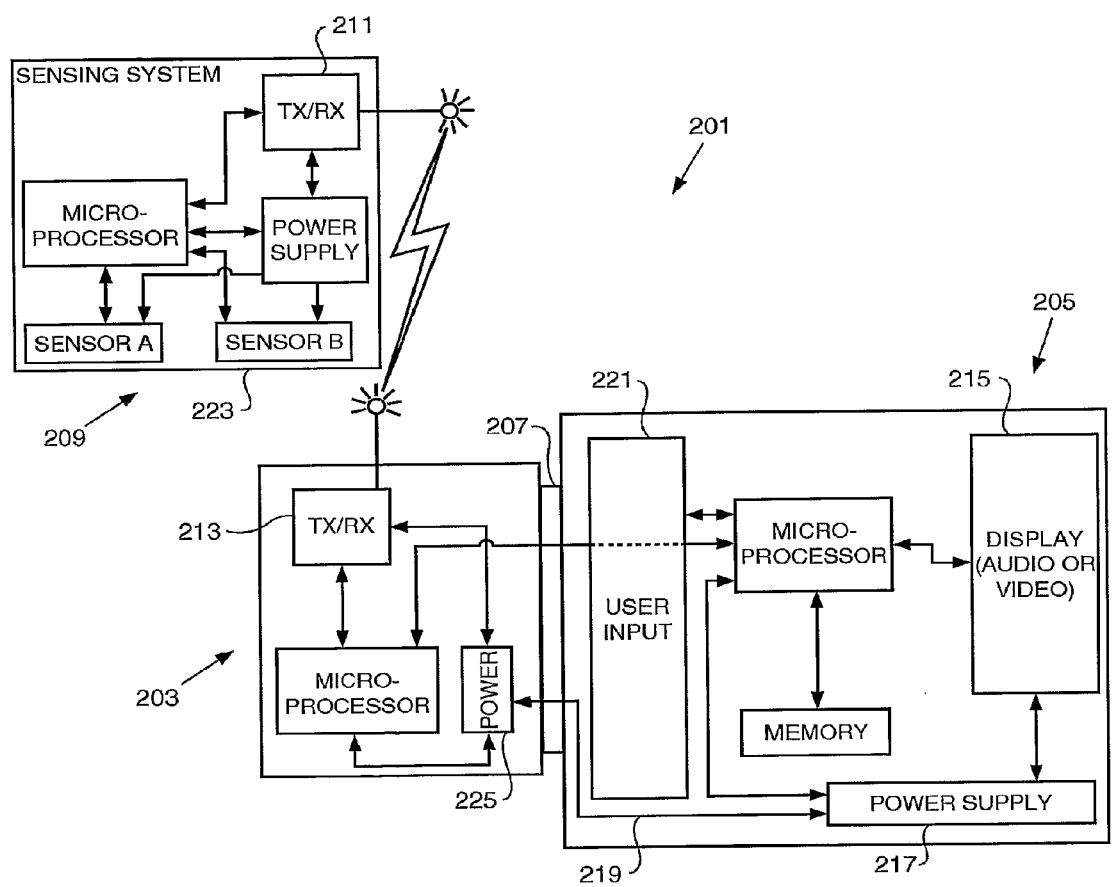
FIG. 18 is a schematic illustrating a wireless device in communication with a wearable device.

FIG. 18 illustrates a schematic diagram of a wireless monitoring system 201. In this system 201, an electronic interface device 203 is physically plugged into a portable electronic display device 205 via a mechanical connection system 207 that holds the two devices together, e.g., in a secure but releasable manner (e.g., via friction fit, detents or retaining elements, etc.). Optionally, if desired, other independent securing elements may be provided to at least partially help hold the interface device 203 with the portable electronic display device 205 (e.g., hooks, straps, snaps, clips, clamps, clasps, retaining elements, etc.). Alternatively, the electronic interface component and the portable electronic display device may form a single component.

This example system 201 further includes a sensing system 209 for measuring and transmitting data. More specifically, in this example structure, accelerometer data is sensed by sensors A and B, and data from these sensors is sent to the sensing system's processing system, e.g., a microprocessor, which optionally may cause the data to be stored (e.g., in a storage system or memory (not shown in FIG. 18), further processed, etc. A separate power supply may be provided to operate the various components of the sensing system 209, such as the sensors, the microprocessor, the data transfer system 211, memory, and/or any other necessary or desired components. If desired, the microprocessor on board the sensing system 209, if any, may process the sensor data, change its form or format, or otherwise manipulate the data prior to sending it on to other parts of the system 201.

At an appropriate or desired time (e.g., when a data request is received, periodically, automatically, upon user demand, etc.), the sensing system 209 may send at least some portion of its data (e.g., raw data directly from one or more of the sensors, data derived at least in part from the raw data, etc.) to the electronic interface device 203, e.g., for eventual display to a user on display device 205. This may be accomplished, for example, as shown in FIG. 18, via a wireless data transmission system (e.g., from wireless data transfer or transmission element 211 in the sensing system 209 to wireless data receiving element 213 in the electronic interface device 203) or in any other desired manner without departing from this invention. Any desired wireless protocol, broadcast protocol, or other data transmission protocol may be used without departing from this invention.

Once received at the electronic interface device 203, the data may be further processed, if necessary or desired, and then supplied to the processing system (e.g., microprocessor) of the display device 205. This may be accomplished at any desired time or timing (e.g., when a data request is received, automatically, periodically, on user demand, etc.) without departing from this invention. From there, the data may be further processed, if necessary or desired, and then sent to the display screen 215 in a form suitable for presentation to and viewing by a user (e.g., in audio, video, and/or alphanumeric form, etc.).

In this illustrated example system 201, power for the electronic interface device 203 is supplied via the power supply 217 used for operating the display device 205 (e.g., which may be a rechargeable battery of a personal data assistant or other portable electronic device), as shown by the connection 219 to the power supply 217 via the connection system 207. The "power" element 225 in interface device 203 in this example may be used simply to distribute power from an external power source (e.g., the power supply 217 of display device 205 in this example) to various components of the interface device 203. Alternatively, the power element 225 may be omitted, e.g., if internal wiring of the interface device 203 allows power transfer from power supply 217 to all required components of the interface device 203. Additionally, in this example system 201, user input may be furnished to control the electronic interface device 402 via input systems 420 provided in the portable display device 205. For example, if desired, a user could enter a specific mode of operation via inputs provided on the display device 205 in which various features, functions, or characteristics of the electronic interface device 203 may be controlled. Additionally or alternatively, if desired, the electronic interface device 203 may include its own input system and/or its own power supply.

Of course, many different arrangements of various elements or components, including some or all of the elements or components shown in FIG. 18, may be used without departing from this invention. Moreover, additional components or elements may be included in such systems, or one or more of the illustrated systems or components may be eliminated without departing from the invention. Additionally, if desired, a single electronic interface device 203 and display device 205 may be simultaneously operatively connected so as to receive data input from multiple independent sensing systems, e.g., of the type shown at reference number 209 (see, for example, the arrangement of FIG. 17). Many variations in the overall structures, components, and architectures of various systems are possible without departing from this invention.

One potential advantage of systems and methods according to at least some examples of this invention lies in the fact that the components and infrastructure of an existing portable electronic display device (e.g., a cellular telephone, MP3 player, PDA, or the like) may be leveraged and used in combination with an electronic interface device that connects thereto and electronically communicates therewith in order to allow this existing electronic device to additionally display and provide data to a user without requiring the user to obtain and carry another electronic display device. As noted above, leveraging the input system and/or power supply of the existing electronic device used for its display can further reduce the size, weight, cost, and complexity of the interface device, thereby providing additional advantages.

Figure 19:
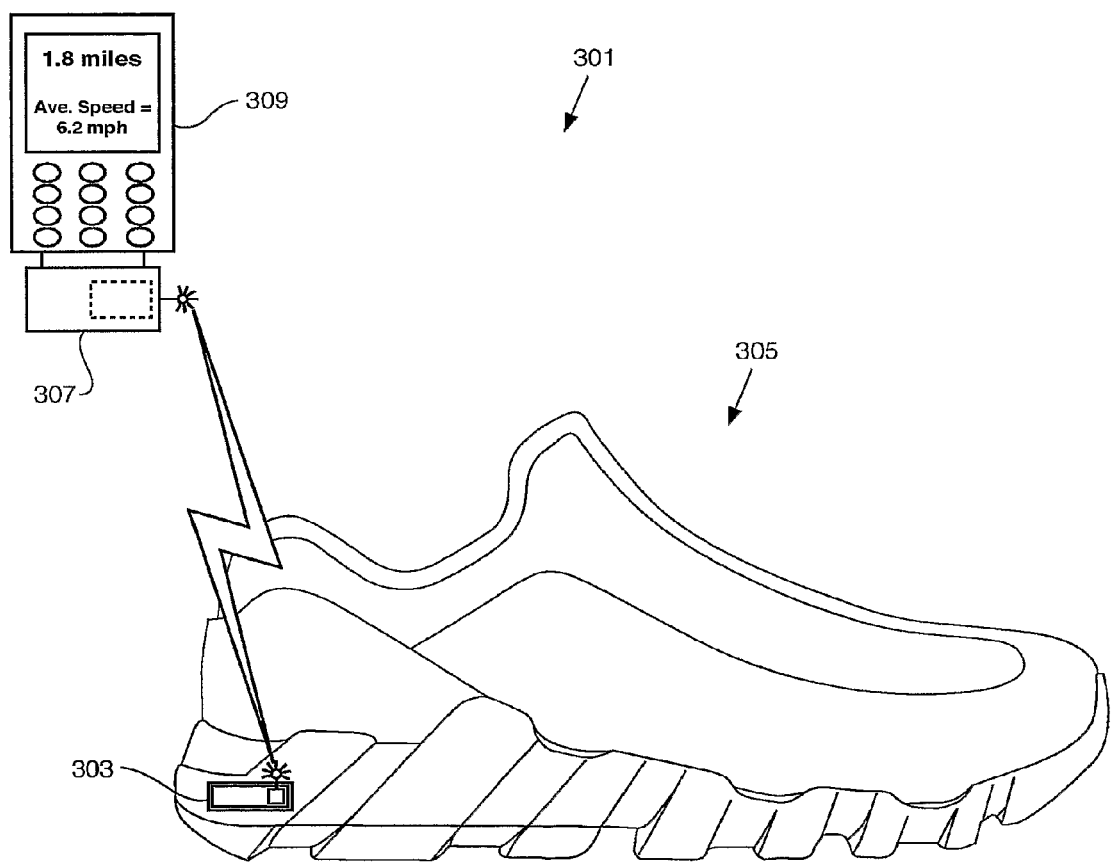
FIG. 19 is a side view of a control unit and wearable device mounted on footwear.

FIG. 19 illustrates an example system 301 in which a sensing module 303 is mounted in an article of athletic footwear 305. The sensing module 303 may include, for example, one or more data sensors, a data transfer system, processing capabilities, a power supply, and/or the like. Any desired manner of mounting the sensing module 303 in or on the article of footwear 305 may be provided without departing from the invention, such as via a slot or chamber, via a mounting pocket or element, via straps, adhesives, mechanical connectors, hook-and-loop fasteners, retaining elements, via user removable connections, etc. Alternatively, if desired, the sensing module 303 may be integrally formed as part of the article of footwear 305, e.g., during footwear manufacture, and/or permanently fixed thereto.

As further shown in FIG. 19, the sensing module 303 may be in wireless (or other) communication with an interface device 307, which in turn is physically connected to a display device 309, such as a cellular telephone as illustrated in FIG. 19. This display device 309 may be attached to the user's body, clothing, or equipment, e.g., so as to be easily carried, moved, and/or viewed. As more specific examples, if desired, the sensing devices aboard sensing module 303 may provide step count data, and the electronic interface device 307 may process this data, optionally along with timing data, so as to provide pedometer type speed and/or distance data for display on display device 309. Of course, any type of data may be provided by sensing modules 303 and any desired type of information may be displayed on display device 309 without departing from this invention.

Figure 20:
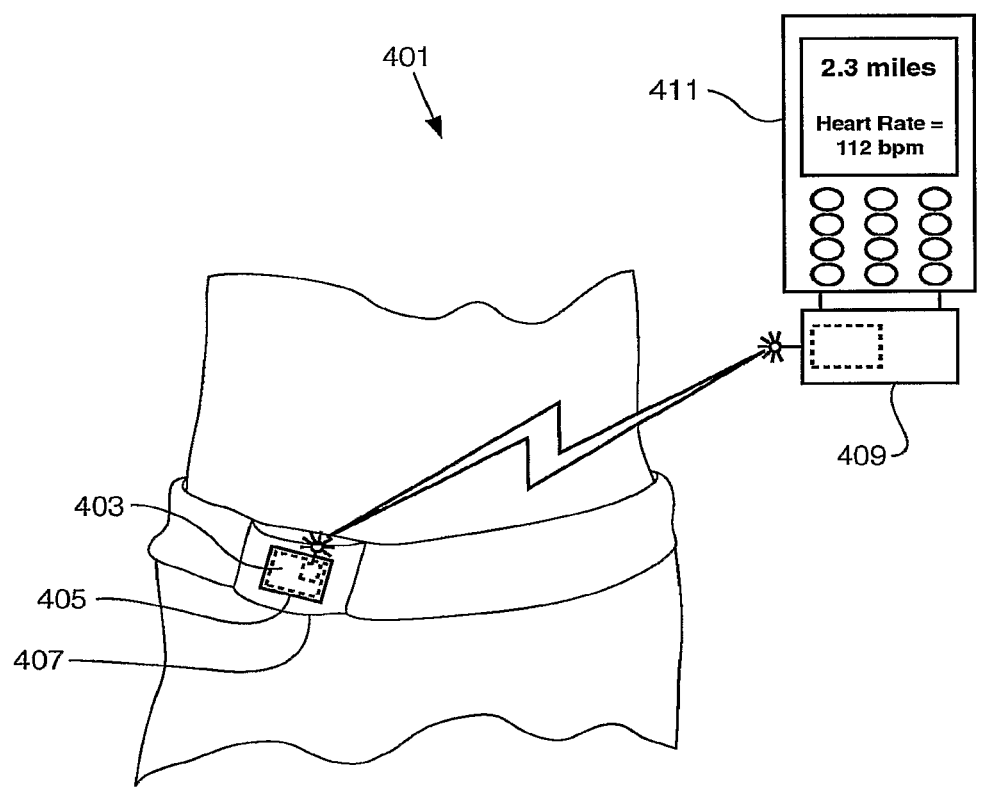
FIG. 20 is a front view of a control unit and wearable device mounted on a belt.

FIG. 20 illustrates another arrangement and/or environment of use of systems 401. In this example, the sensing device 403, including one or more individual sensing elements for measuring data, is mounted in or on an article of clothing, such as in a pocket or other attachment element 405 provided in a belt or band 407. The belt or band 407 or other article of apparel may be attached to the user's body (e.g., arm, waist, chest, leg, head, etc.) and may be arranged so that the sensing elements on board sensing device 403 measure the desired data (e.g., physical data, such as step count, acceleration, speed, distances, impact force, etc., or physiological data, such as heart rate, pulse rate, air intake/exhale volumes or rates, body temperature, blood pressure, EKG data, EEG data, etc.). The measured data may be transmitted to the electronic interface device 409, optionally after initial processing, which in turn may further process the incoming data and transfer it on to display device 411 for display to the user.

Figure 21:
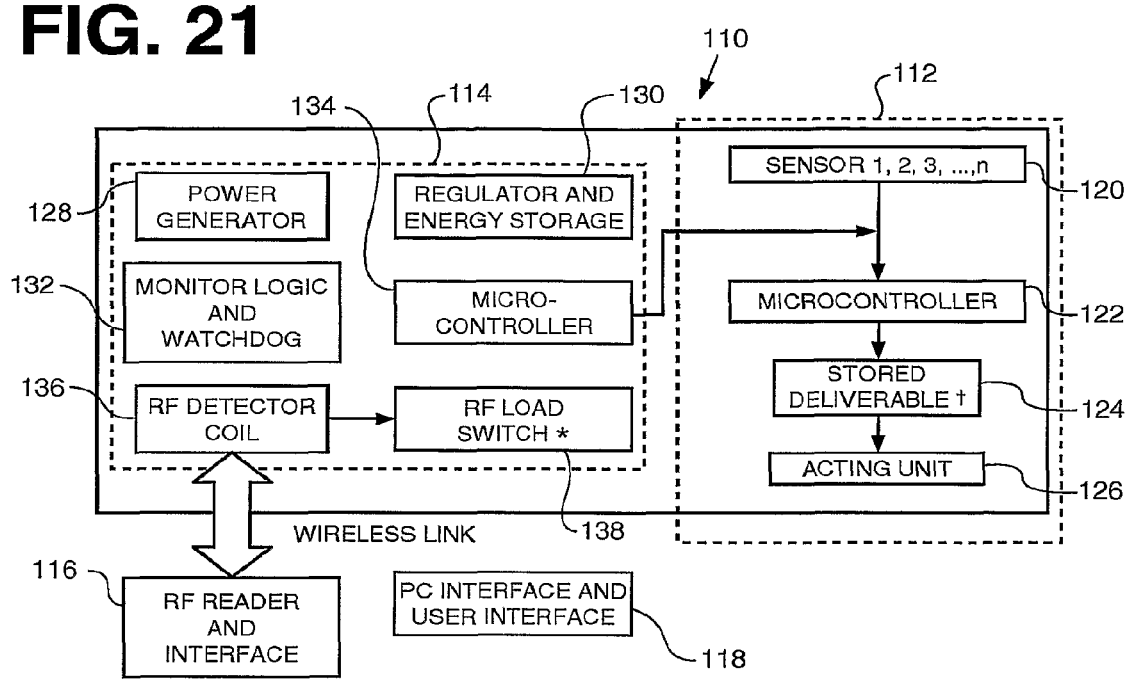
FIG. 21 is a schematic illustrating a telemetric orthopaedic implant system.

Not only does the telemetric IM nail 10 include a sensor, but also the telemetric IM nail may include an acting unit to perform certain functions based on sensor readings or external commands. FIG. 21 illustrates a telemetric implant system 110. The telemetric implant system 110 includes a telemetric orthopaedic implant 112, a control unit 114, a reader 116, and a computing device 118. The reader 116 wirelessly communicates with the control unit 114 to transmit and receive data. The reader 116 is connected to the computing device 118 either by wires or wirelessly. The computing device 118 may be any number of known devices, such as a personal digital assistant, a desktop computer, a laptop computer, a notepad PC, a biometric monitoring device, a handheld computer, or a server. The computing device 118 is used to analyze the data received from the orthopaedic implant 112. The computing device 118 may be used to store data and/or to program the telemetric orthopaedic implant 112. The reader 116 and the computing device 118 may be incorporated into a single device.

The orthopaedic implant 112 includes one or more sensors 120, a microcontroller 122, one or more stored deliverables 124, and one or more acting units 126. The sensor 120 outputs an induced signal to a preamplifier (not shown), then to an amplifier (not shown), and then to a filter (not shown). The signal travels then to the microcontroller 122 which processes the sensor signal via an algorithm and decides if the information is to be stored or sent to the acting unit 126. The algorithm used to decide how to act can be preprogrammed from the manufacturer or by surgeon preference. The acting unit 126 may communicate with the microcontroller 122 either by wire or wirelessly. Upon receiving the signal from the control unit 114 or the microcontroller 122, the acting unit 126 deploys a stored deliverable 124, which includes, but is not limited to, biological manipulations, an antibiotic, an anti-inflammatory agent, a pain medication, an osteogenic factor, radio-markers, angiogenic factors, vasodilator, and/or growth factors.

The acting unit 126 may be a MEMS device, such as a pump that delivers a specific volume of medicament or other stored deliverable 124. The orthopaedic implant 112 may include several of these pumps that all contain the same stored deliverable 124 as to offer redundancy in case one or more of the pumps fail. The pump contains a reservoir or reservoirs of stored deliverable 124 to be delivered. The stored deliverable 124 is delivered using any type of microfluidic mechanism, such as a rotary pump, a piston pump, a shape memory material pump, etc.

The control unit 114 includes a power generator 128, an energy storage device 130, a logic circuit 132, a microcontroller 134, an RF detector coil 136, and an RF load switch 138.

User Interface

In some embodiments, the computing device 118 includes a graphical user interface (GUI). The GUI allows a healthcare provider and/or patient to display information based on the collected data either locally or remotely, for example telemedicine, from the telemetric orthopaedic implant 112. The GUI may include an audio device for producing sound to relay information to the user. The GUI identifies the system to communicate with, prompts the user for security clearance, verifies the security clearance, and downloads the data from the telemetric orthopaedic implant 112 or the reader 116. The data is then further processed into various forms from simple discrete healing progress status numbers or verbiage to complex information such as a graphical reproduction of the patient gait cycle curve, patient activity, patient compliance, patient data, patient medical records, healthcare provider information, implant manufacture information, surgical techniques, x-radiograph information, computed tomography imaging information, magnetic resonance imaging information.

Further, the patient could be alerted by the GUI as a result of sensed information. The logic circuit 132 may be used to monitor data received from the telemetric orthopaedic implant 112 and send a signal if a certain variable exceeds a preconfigured limit. The alert could let the user know when a clinic visit is necessary for doctor intervention, the device has been overloaded, or how to manage a situation that has occurred without surgeon intervention.

The telemetric implant system 110 has many uses. For example, a patient may undergo a surgical intervention to repair a sustained injury or joint reconstruction, during which time the patient receives a telemetric orthopaedic implant to aid in the repair of the injury. The implant may utilize an electromechanical system designed to monitor various aspects of the patient's recovery with one or more sensors, decide if an action needs to take place, and hence act as programmed.

Early Monitoring of Bone Healing

While immobilization and surgery may facilitate bone healing, the healing of a fracture still requires adequate physiological healing which can be achieved through continuously monitoring changes in the in situ load distribution between the implant and the surrounding bone using sensors and a biotelemetry system. The mass and architecture of bone are known to be influenced by mechanical loading applied to them. In the absence of appropriate loading due to stress shielding caused by poor management of internal orthopaedic fixation systems, bone mass is reduced resulting in compromised healing of the fracture. The primary function of a telemetric orthopaedic implant is to carry the load immediately after surgical placement. For example, the telemetric orthopaedic nail carries the load immediately after surgical placement in the intramedullary canal. With progression of fracture healing, the load sharing between the implant and the bone changes. This can be tracked using strain gauges optimally positioned within the orthopaedic implant according to the location of the fracture. The sensors are used to monitor the progress of union in the case of fracture by continuously monitoring the load component of the healing bone in all spatial components, which is unobtainable from X-rays. Periodic follow-up provides a graph that shows the gradual decrease of relative motion of the fragments until union occurs.

Each fracture patient generates his or her own unique healing curve; however, the general shape of the healing curve indicates whether the fracture progress to either a union condition or a non-union condition. The healing curve generated from a patient is dependent upon a number of factors including the type and location of the fracture, health status (underlying disease), age, activity, rehabilitation, and time to reach weight bearing.

Figure 22A:
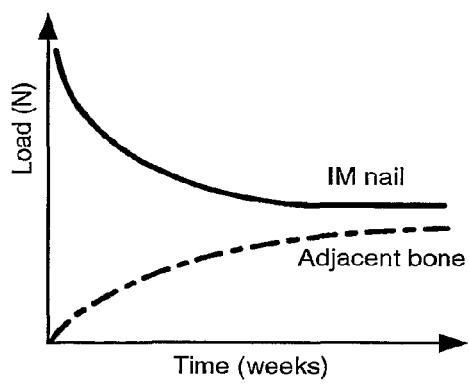
FIG. 22A is a graph illustrating a fracture healing curve.
Figure 22B:
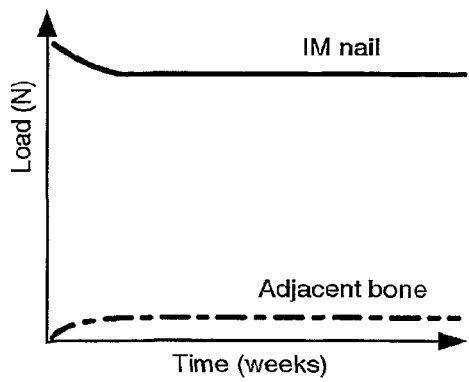
FIG. 22B is a graph illustrating a non-union fracture healing curve.

Hypothetical load vs. healing time curves showing the loading distribution between an instrumented IM nail and the surrounding bone are schematically illustrated in FIG. 22A and FIG. 22B. In FIG. 22A, the fracture is progressing to a union condition, and in FIG. 22B, the fracture maintains a non-union condition. Non-union or pseudarthrosis usually means that there is motion between the two bones that should be healed or fused together. Although fracture healing results in a reduction in implant load, the remaining load of the nail can be significant and are expected to increase with patient activity. It has been suggested that loading of the bone may increase up to 50 percent after implant removal. The load measured in the adjacent bone is determined by subtracting the implant load from the load exerted through the limb, which is determined using either a force plate or balance. The clinician also can measure the load acting through the contralateral limb in order to provide a reference measurement for a fully functional limb.

Figure 23:
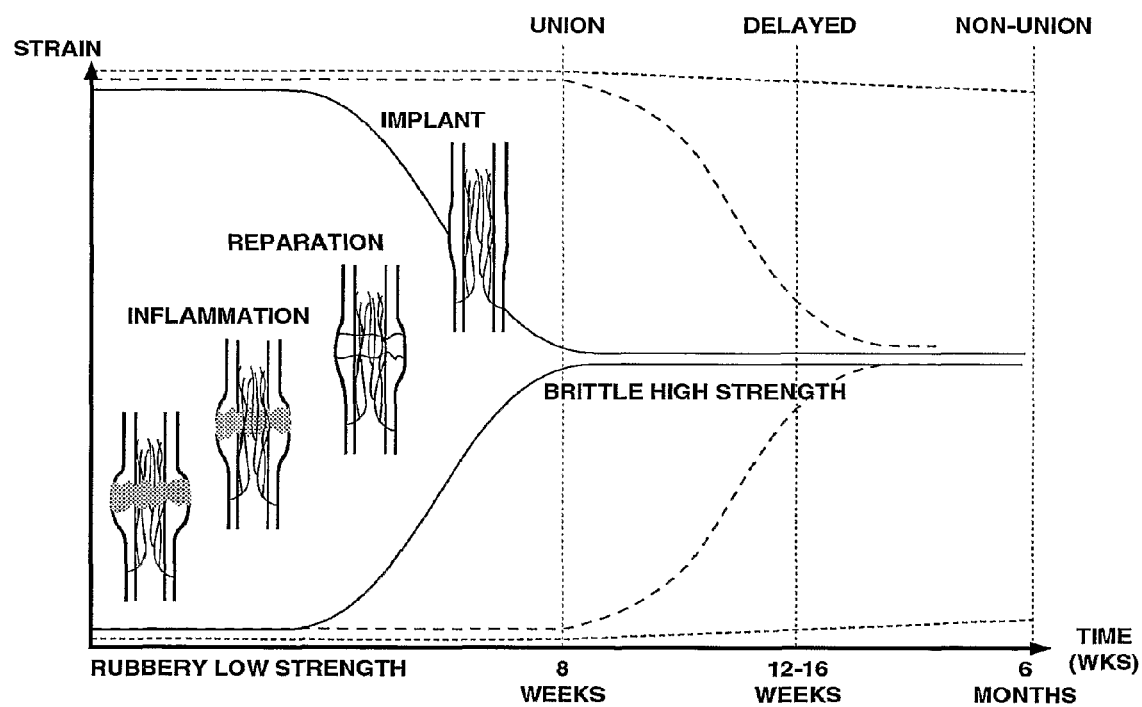
FIG. 23 is a is a graph illustrating fracture healing curves.

FIG. 23 illustrates an amount of time that a high implant strain condition may exist. The union condition is the general desired state for achievement of a healed fracture. Delayed fracture healing is generally defined as bony union within a period outside the normal expected time for fracture healing, such as three to six months. Non-union or pseudarthrosis is defined as no substantial detectable bony fusion within a period of six months or longer.

The healing curve may be used in several different ways. First, in the case of an active telemetric orthopaedic implant, the implant or control unit continuously records data. In the case of an intramedullary nail as an example, the strain on the implant is recorded as the patient ambulates. The surgeon or other healthcare provider may download the data from the implant or control unit in a clinical setting. The data is processed and a healing curve is generated from the data. If the surgeon observes that the strain on the implant is decreasing with time, similar to the graph of FIG. 22A, this implies that the surrounding hard tissue is accepting some of the load and, thus, the fracture is healing. However, if the strain on the implant is unchanged with time and at the approximate level as when the patient was discharged from the hospital or other health care facility, similar to the graph of FIG. 22B, then this implies that the surrounding hard tissue is not bearing the load and, therefore, the fracture is not healing.

Second, the telemetric orthopaedic implant may be a passive device that does not record data continuously but only when it is exposed to an energy source. In this embodiment, the hospital, healthcare facility, subject's residence or other location provides an energy source which energizes the telemetric orthopaedic implant and allows it to record data. In this example, the telemetric orthopaedic implant is energized, a load is placed on the affected bone with the implant at to a set level, and sensor readings are captured. For example, the implant may be an intramedullary nail and the sensors may measure strain on the nail as the load is applied. The sensed data is downloaded and processed. In this example, the sensed data must be compared to previous measurements. For example, measurements may be taken at predetermined time periods, such as daily or weekly. If the load applied to the bone is unchanged and the strain has decreased compared to previous measurements over time, then it is implied that the hard tissue is sharing some of the load and, thus, the fracture is healing. However, if the strain on the implant remains unchanged compared to previous measurements over time, this implies that the surrounding hard tissues is not bearing any of the load and, therefore, the fracture is not healing.

Telemetric orthopaedic implants of the kind described herein utilize an algorithm that gives an early indication as to whether the fracture will heal or not based on the rate of change in the initial load measurements. The information provided by the sensors also may be used to design a new class of orthopaedic implants that are more compliant with the surrounding bone in terms of strength and stiffness.

Figure 24:
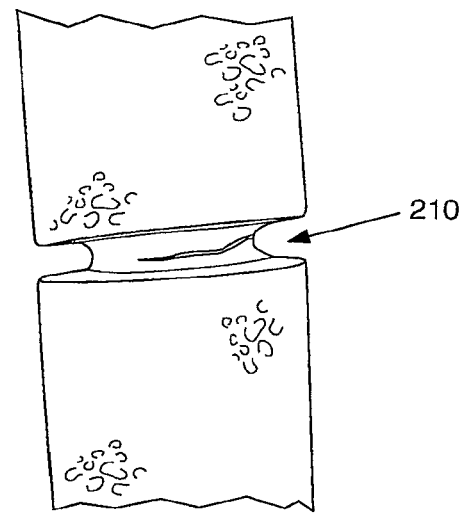
FIG. 24 illustrates an artificial fracture gap.
Figure 25:
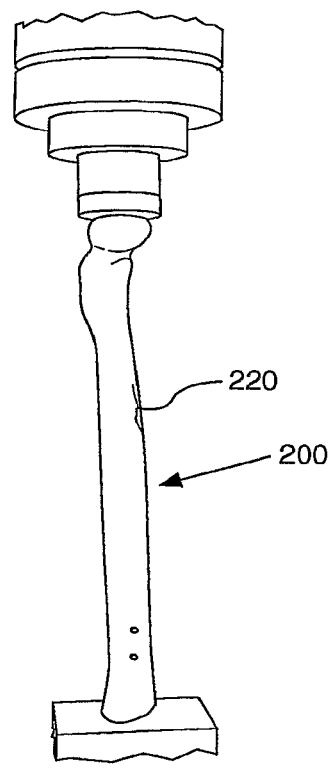
FIG. 25 illustrates an in vitro biomechanical test setup.

The functionality of a telemetric orthopaedic implant may be demonstrated in vitro using a plastic fracture model. In this test shown in FIGS. 24 and 25, a telemetric intramedullary nail 220 is implanted in an intact femur model 200 and gradually, a circumferential fracture gap 210 is introduced while observing changes in the strain as a function of load. Thus, reversing the fracture conditions typically observed in vivo. The strain gauges are applied to the medial and lateral sides of the nail 220, positioned on the shaft of the nail to correspond with the fracture gap placement. Interpretation of the data obtained from this study represents the ability to measure bone healing in vivo. The nail construct is loaded at a stepwise displacement from about 0 lbf to about 300 lbf in predetermined increments and the strain is measured at each load increment. The first series of strain measurements are made with the bone model completely intact. The next series of strain measurements are made with 75% of the fracture gap 210 in place. Subsequently, the third, fourth, and fifth series of strain measurements are made with 50%, 25%, and 0% of the fracture gap 210 in place, respectively. A final series of strain measurements is made with the fracture gap segments re-inserted to their original position. The fracture gap 210 is approximately 5 mm thick, positioned on the shaft of the bone model such that it is at half of the working distance of the nail 200, which means it is half of the distance between the locking fasteners.

Figure 26:
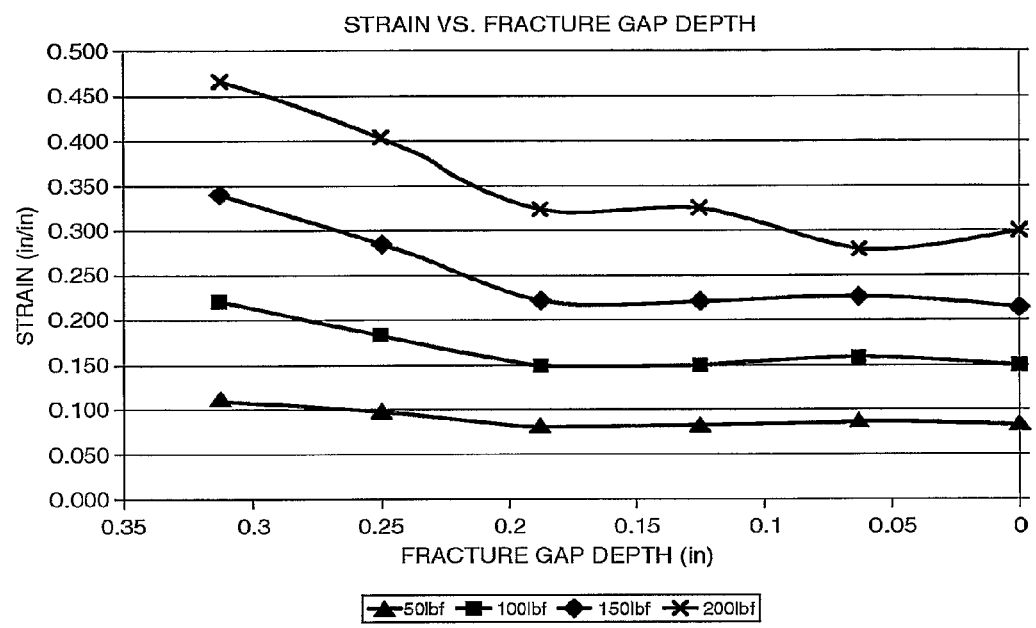
FIG. 26 is a graph illustrating strain vs. fracture gap depth as a function of load.
Figure 27:
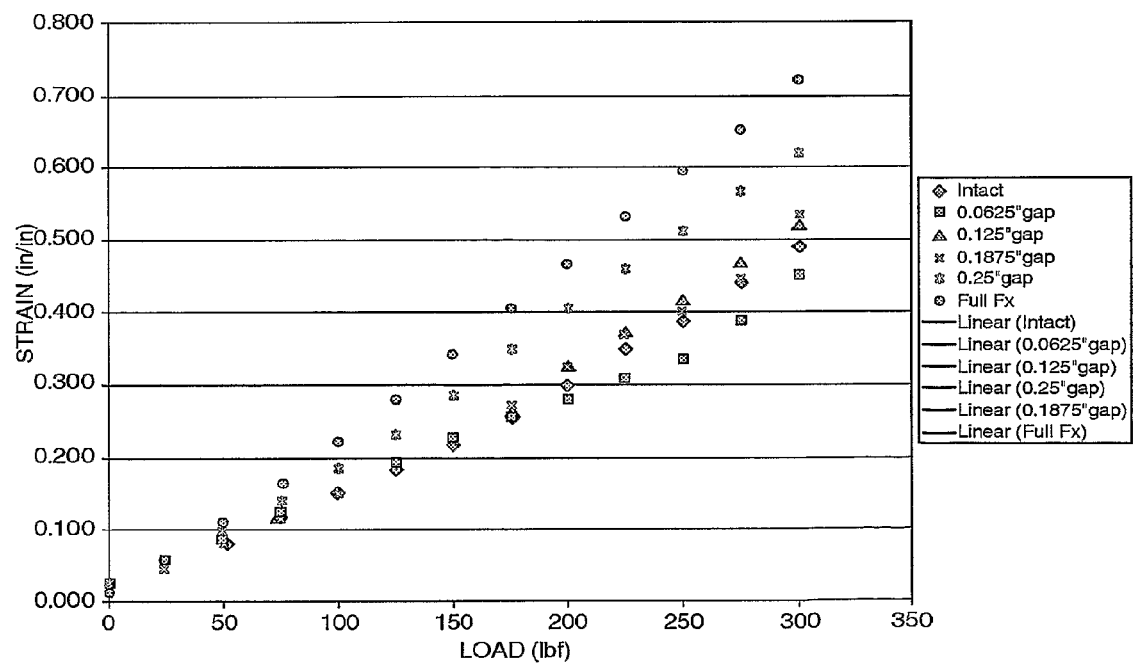
FIG. 27 is a graph illustrating strain vs. load as function of gap volume.

FIG. 26 illustrates reverse simulated bone healing using an artificially induced circumferential gap. FIG. 27 illustrates load vs. strain curves obtained from the plastic fracture model with 100% (fully intact), 75%, 50%, 25%, and 0% (fully fractured) of the fracture gap in place.

Gait Analysis

Figure 28:
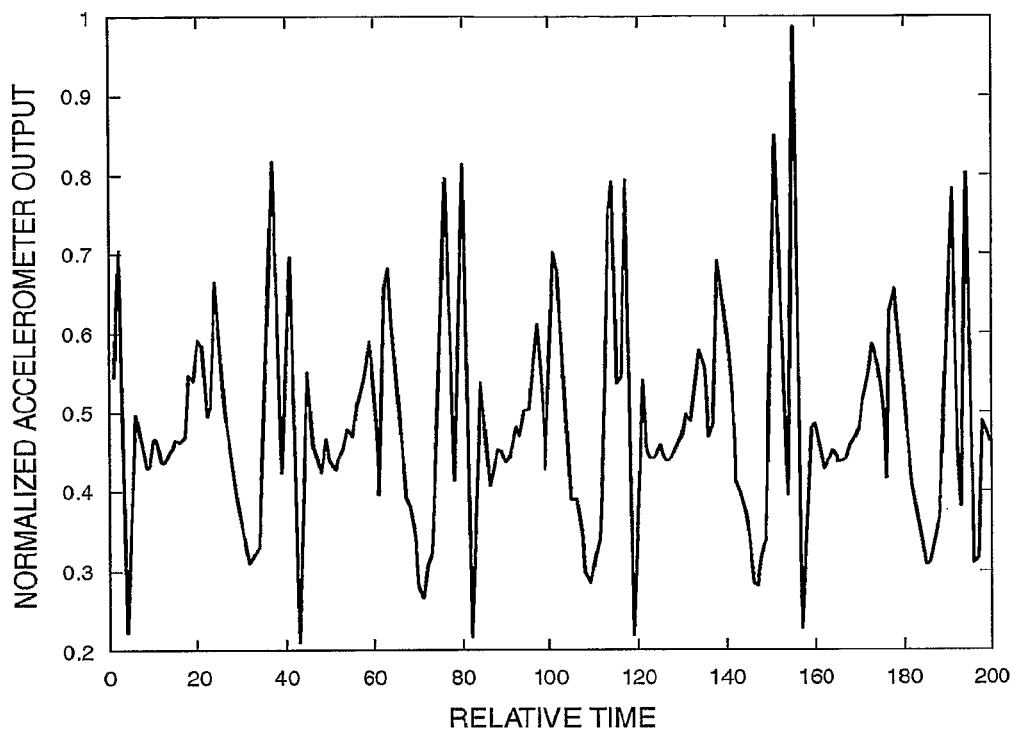
FIG. 28 is a graph illustrating accelerometer output vs. time.
Figure 29:
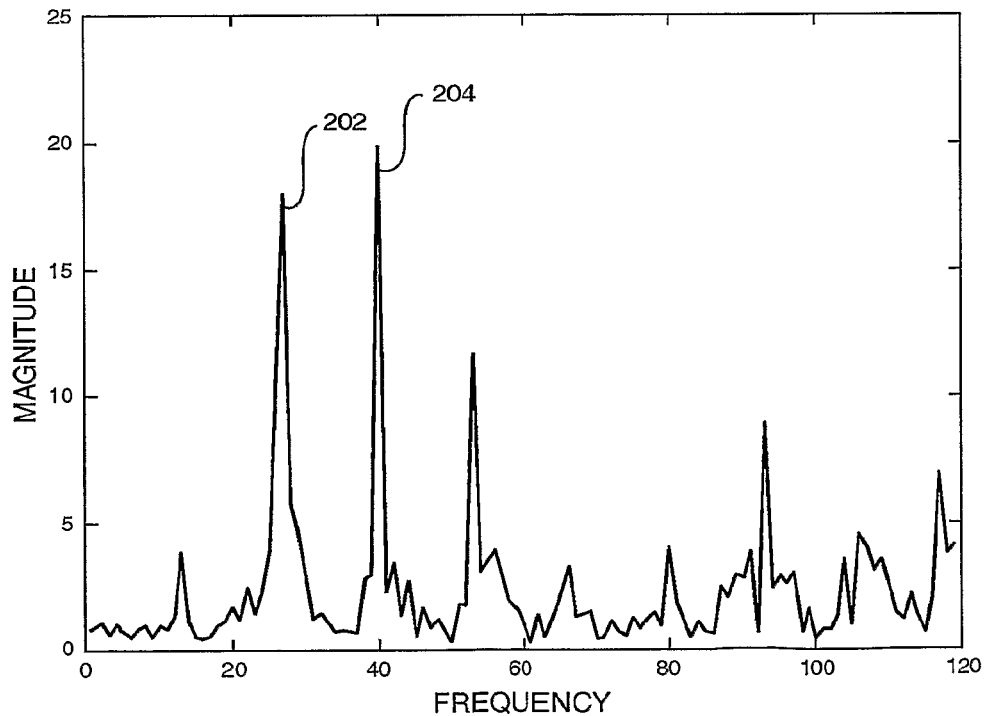
FIG. 29 is a graph illustrating magnitude vs. frequency.
Figure 30:
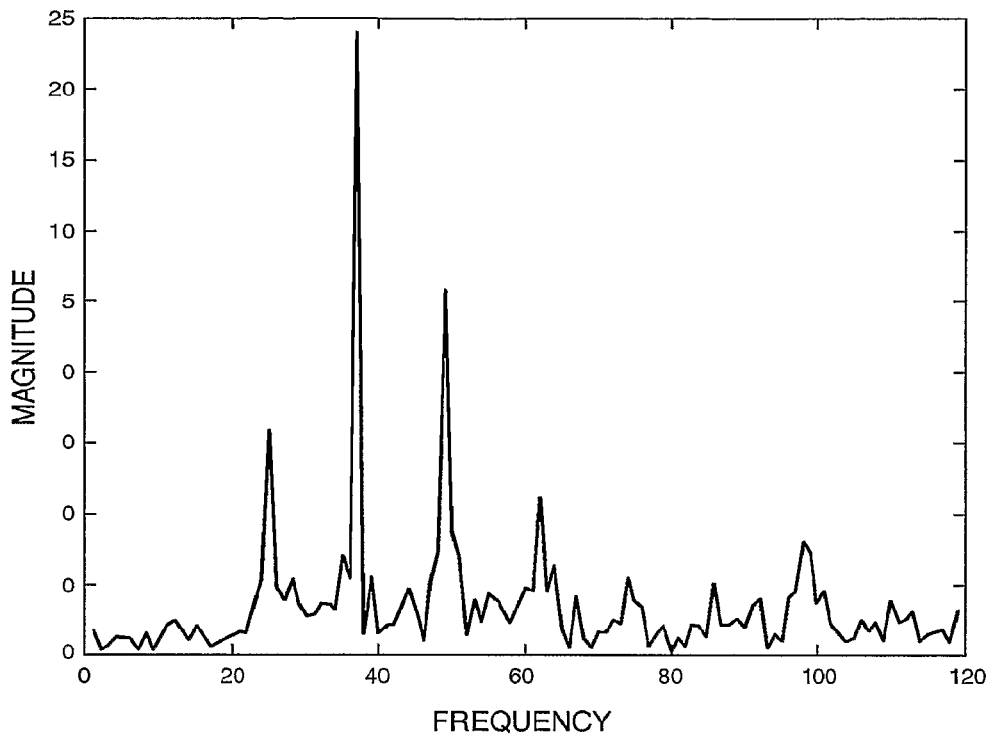
FIG. 30 is a graph illustrating magnitude vs. frequency.
Figure 31:
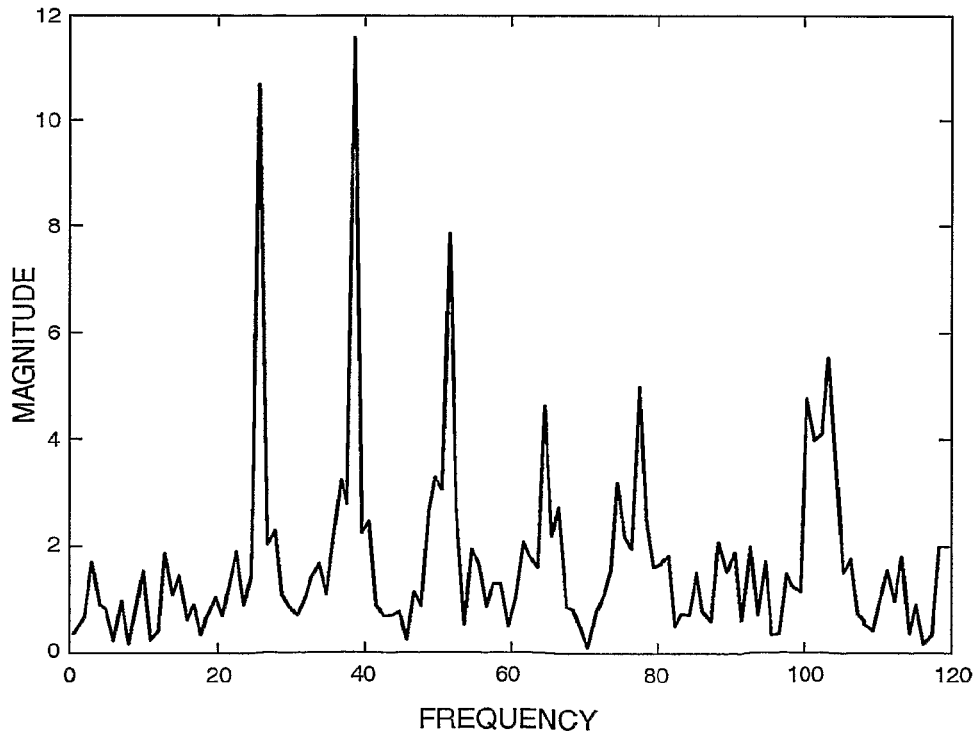
FIG. 31 is a graph illustrating magnitude vs. frequency.
Figure 32:
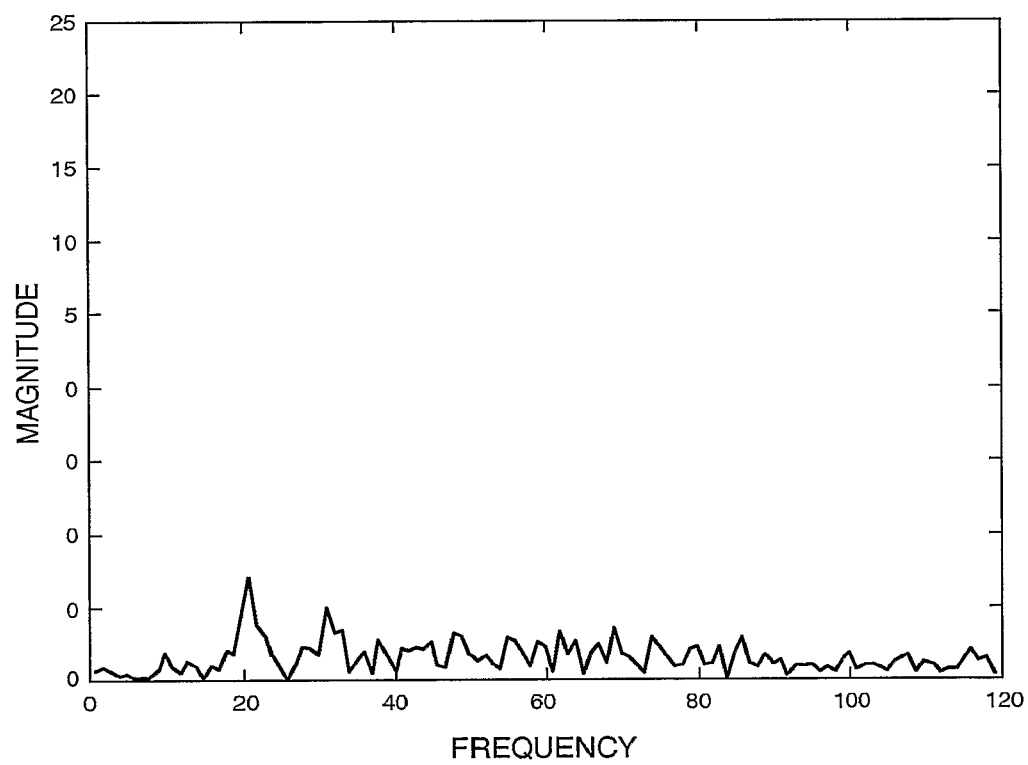
FIG. 32 is a graph illustrating magnitude vs. frequency.

The invention also includes a gait analysis tool in which gait data is gathered, processed, and stored until an external device accesses the data and presents it to a reviewer, such as a patient, surgeon, healthcare provider, or physical therapist. The telemetric orthopaedic implant may include an accelerometer, which can output acceleration changes over time at a sampling rate ranging from about 1 Hz to about 20000 Hz. Reference FIG. 28 for an example of graphically represented data output resulting from wearing an accelerometer and the wearer undergoing normal unassisted gait. The sensor output data can then be manipulated as desired for analysis. One such method is to convert the data from the time domain to the frequency domain and look for biometric markers or patterns. FIGS. 29-31 show data similar to that in FIG. 28 transformed into the frequency domain. In these figures, distinct peaks are seen at various frequencies which define the wearer's gait signature seen as the differences in FIGS. 29-31. The patient's gait changes gradually with time and aging or abruptly as is the case when a patient sustains a severe traumatic injury to any of the bone in their lower extremity. The frequency domain gait signature for an artificially induced antalgic gait pattern is seen in FIG. 32.

The gait analysis tool allows for basic information to be gathered and processed yielding conclusive valuable data with respect to a subject's gait cycle. This data can be used to diagnose the patient's healing status in at least their lower extremities, which when injured impede the normal gait cycle. Historically, surgeons have had to rely on radiographs or other imaging techniques to determine the stage of the patient's bone healing cascade. These tools are helpful but allow for error in diagnosis. There are several areas for this opportunity including but not limited to image quality, parallax, and misdiagnosis. Further, even though these diagnosis tools exist, the surgeon relies on patient testimonial more heavily than the images. The gait analysis tool removes the supposition from the diagnosis by providing the surgeon objective unbiased data collected from the patient throughout the healing process. The gait analysis tool allows the surgeon to understand earlier in the healing process if intervention is needed to augment treatment using a biologic, such as an injectable cement or demineralized bone matrix, to speed healing or if a revision surgery may be necessary. Because the telemetric orthopaedic implant described herein has a memory function, patient data may be stored thus allowing for the easy transmission of the data. This data could include personal data, patient history information, as well as patient activity. If the activity is captured, the surgeon could discern if the patient has been accurately performing postoperative rehabilitation regimens. This allows the surgeon to accurately predict and prescribe further regimens, which currently is not feasible with existing employed technology.

As noted above, the gait analysis tool utilizes an accelerometer sensor to record the changes in acceleration of an implant or any part of the patient while the patient is walking or otherwise ambulating. In one instance, the sensor 12 measures acceleration of the implant 10 over time. Alternatively, the patient wears an accelerometer device after being treated for a bone fracture or after reconstructive surgery. As examples, the patient may have an accelerometer attached to his or her thigh after being treated for a femoral fracture with an intramedullary nail or after a total hip replacement. As the patient returns to normal life and ambulates with crutches, then a walker, then a walking cast, etc., the changes in acceleration are recorded within the device. The data is then used to analyze the patient's gait normalcy and give an indirect method of determining the patient health, in this case fracture healing.

The direct output of the device provides acceleration data with corresponding time of data capture. This data is represented graphically as acceleration versus time. An example is given in FIG. 28. This graph is analyzed and compared to a library of data to determine the level of patient healing; however, a much more robust and reliable method may exist in frequency domain analysis. The acceleration versus time graph is considered a time domain data set in that the independent variable is time and the dependent variable is acceleration. In other words, acceleration is a function of time. There are popular techniques exploited to solve common problems by transforming time domain data into the frequency domain. Two common methods are the Laplace Transform and the Fourier Transform. Within these techniques there are sub-categories and one of particular interest is the Fast Fourier Transform or NH. Within this sub-category, FFT, several specific algorithms are available including, but not limited to, Cooley-Tukey FFT algorithm, Prime-factor FFT algorithm, Bruun's FFT algorithm, Rader's FFT algorithm, and Bluestein's FFT algorithm. For the work described herein, any of the FFT algorithms, other Fourier Transform algorithms, and any Laplace Transform algorithm is suitable. An example of a frequency domain graph corresponding to the time domain graph in FIG. 28 is seen in FIG. 29.

The frequency domain plot yields information that is useful in determining the degree of normalcy of the gait cycle of a patient. Referring to FIG. 29, a first peak 202 indicates a stride point, and a second peak 204 indicates a step point. The peaks 202, 204 indicate the gait cycle. While all of the peaks have value and can represent different portions of the gait cycle, the most important peaks are the step and stride. When analyzing a normal gait cycle, these peaks are pronounced and as the gait cycle digresses into abnormality these peaks decrease. FIGS. 29-32 illustrate four graphs of a diminishing gait cycle going from normal to highly abnormal. These are the frequency domain graphs transformed from the time domain data taken from a subject who was wearing an accelerometer on the thigh. The subject was allowed to walk as normal in FIG. 28 but then was subjected to artificially induced abnormal gait by progressively increasing pain on the sole of the foot of the instrumented leg in FIGS. 30-32. In all of the FIGS. 29-32, frequency remains on the abscissa and the amplitude remain in the ordinate.

Figure 33:
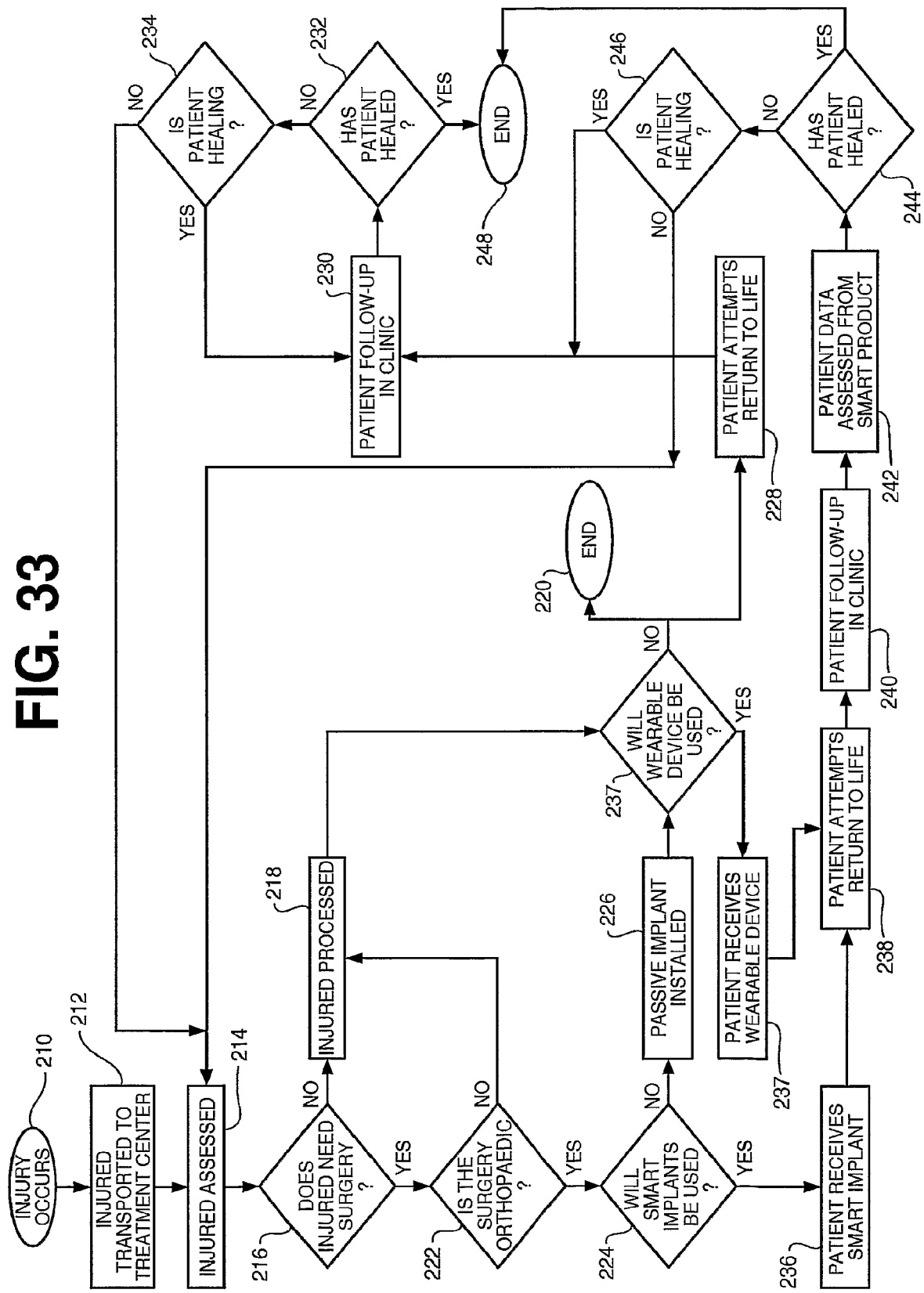
FIG. 33 is a flowchart illustrating implementation of a smart implant.

Once the accelerometer data is captured, it is processed, then analyzed. To this end, FIG. 33 illustrates a flowchart of the scenario for the events leading to accelerometer data capture and through data processing. The patient is injured in step 210. Once the patient has been injured, he or she is transported to a treatment center (e.g. hospital, or emergency room) in step 212. The injury is assessed in step 214. Once evaluated, the decision is made to operate or not operate in step 216. If surgery is not needed, the patient is processed in step 218. At step 227, a decision is made whether the patient will receive a wearable device that includes an accelerometer. If not, the process ends at step 220. The patient attempts to return to normal life in step 228. Optionally, the patient may receive a follow-up in a clinic or other healthcare facility in step 230. Thereafter, the patient returns to the clinic or other treatment facility for decisions 232, 234. In decisions 232, 234, it is assessed whether the patient has healed and whether the patient is in fact healing. When the patient is healed, the process ends in step 248. Otherwise, the patient returns to the clinic after a period of time at step 230. This follows the typical process of bringing the patient back to the clinic at preset intervals based on type of injury, occurrence of patient characteristics, and patient assessment utilizing current assessment tools. As noted above, this process is inadequate as the patient care is usually conservative in that the care giver typically reviews the patient's testimonial, reviews the x-rays, and manually manipulates the injured bone through the soft tissues. Many times this evaluation provides little to no feedback as to the degree of healing (or lack thereof) that the patient has gone through. Therefore, the care giver conservatively brings the patient back to the clinic for future evaluation although the patient may have in fact healed. The result is a huge cost thrust on to the health care system, government, and tax payer.

If the patient does need surgery, there is another decision whether the patient requires orthopaedic surgery in step 222. If the patient does not need orthopaedic surgery, the patient is processed in step 218. If the surgery is orthopaedic in nature, a decision is made in step 224 whether the patient will receive a smart implant. If the patient does not receive a smart implant, the patient receives a passive implant in step 226, and a decision is made in step 227 whether the patient will receive a wearable device that includes an accelerometer. If the patient does not receive a wearable device, the patient attempts to return to life in step 228 and possibly receives follow-up in a clinic or other treatment facility in step 230. Otherwise, the patient receives a wearable device in step 237 and proceeds to step 238.

If decision 224 leads to the implantation of a smart implant, however, the patient receives a smart implant in step 236. The patient attempts to return to normal life in step 238. The patient receives follow-up in a clinic or other treatment facility in step 240. In operation 242, data is retrieved from the smart implant or the wearable device and is assessed. In decision 244, the data is used to determine whether the patient has healed. If the patient has not healed, there is a decision in step 246 to see whether the patient is healing. If the patient is not healing, the patient returns to step 214 for injury assessment. If the patient is healing, the patient returns to step 240 for further follow-up. This cycle continues until it is decided in step 244 that the patient has healed, wherein the patient proceeds to step 248 where the process ends. Because the assessment is based upon objective evidence obtained with the smart implant or wearable device, the patient healing status determination is much more reliable.

Figure 34:
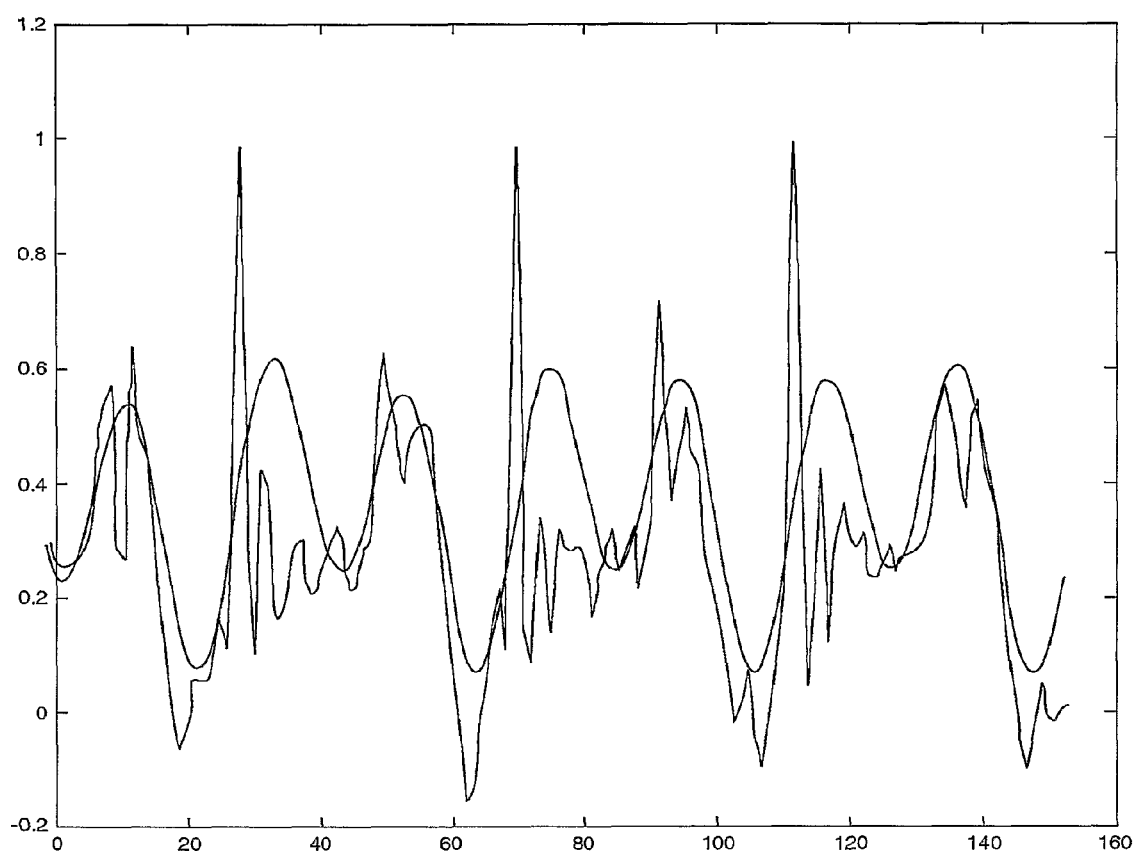
FIG. 34 is a graph illustrating a simplified gait plot imposed over raw data.

Once the device is within wireless range or is otherwise tethered to a device suitable to read the data, such as a computer, the data is retrieved from the device. This data is global raw accelerometer output (acceleration) versus time. All of this raw data is transformed from the time domain into the frequency domain in a manner described earlier. Within the frequency domain the data is analyzed to determine if the characteristic gait pattern exists in the form of peaks, Fstride and Fstep. If these harmonic peaks are not found, the data is read again and the process repeats. If the peaks are present, the data is processed (a simple summation of the harmonic functions, in this case sinusoidal) including other characteristics of the gait cycle, such as harmonic function amplitude, Astride and Astep. The mathematical representation of the overall gait cycle is then generated as shown in the equation below:

$$f(t) = \sum_{i=1}^{n} a_i \sin\alpha_i 2\pi f_i t + C$$

where n≥2 and is the number of harmonics found in the data, $a_i$=the ith harmonic amplitude (for example a1=astride and a2=astep), $f_i$=the ith harmonic frequency, $\alpha_i$=the ith harmonic constant, and C=a constant. FIG. 34 illustrates an example simplified gait plot superimposed over raw data.

From the two curves, a cross-correlation is computed to determine the fitment of the regression curve. This is done on the global raw data set or performed on discrete sections of the raw data. Once the cross-correlation is performed it is determined whether the fitment is acceptable (correlation coefficient above an adaptive threshold) or not. If the fitment is not acceptable, the process is repeated. If the cross-correlation is performed on the global raw data set there might be a tendency to overlook and even omit pertinent discrete data sets. It is therefore recommended, but not required, that discrete data sets over a prescribed time frame be analyzed for fitment. If the discrete data set proves to not meet the fitment criteria the data set is labeled as a non-gait cycle and stored for reference. Conversely, if the discrete data set proves to not meet the fitment criteria the data set is labeled as a gait cycle and further processed. This discrete data set is stored, again undergoes a transform into the frequency domain, and is further analyzed to determine healing status of the patient.

Once the level of patient healing is discovered, the healthcare provider can decide the treatment regime for the patient. If the patient is healed, the healthcare provider could opt to dismiss the patient forever or follow-up in several months. If the patient has not healed but is healing, a follow-up appointment may be made based on that particular patient's recovery rate. If the patient has not healed and is not showing signs of healing, the healthcare provider could opt to intervene surgically or otherwise to promote patient healing.

Figure 35:
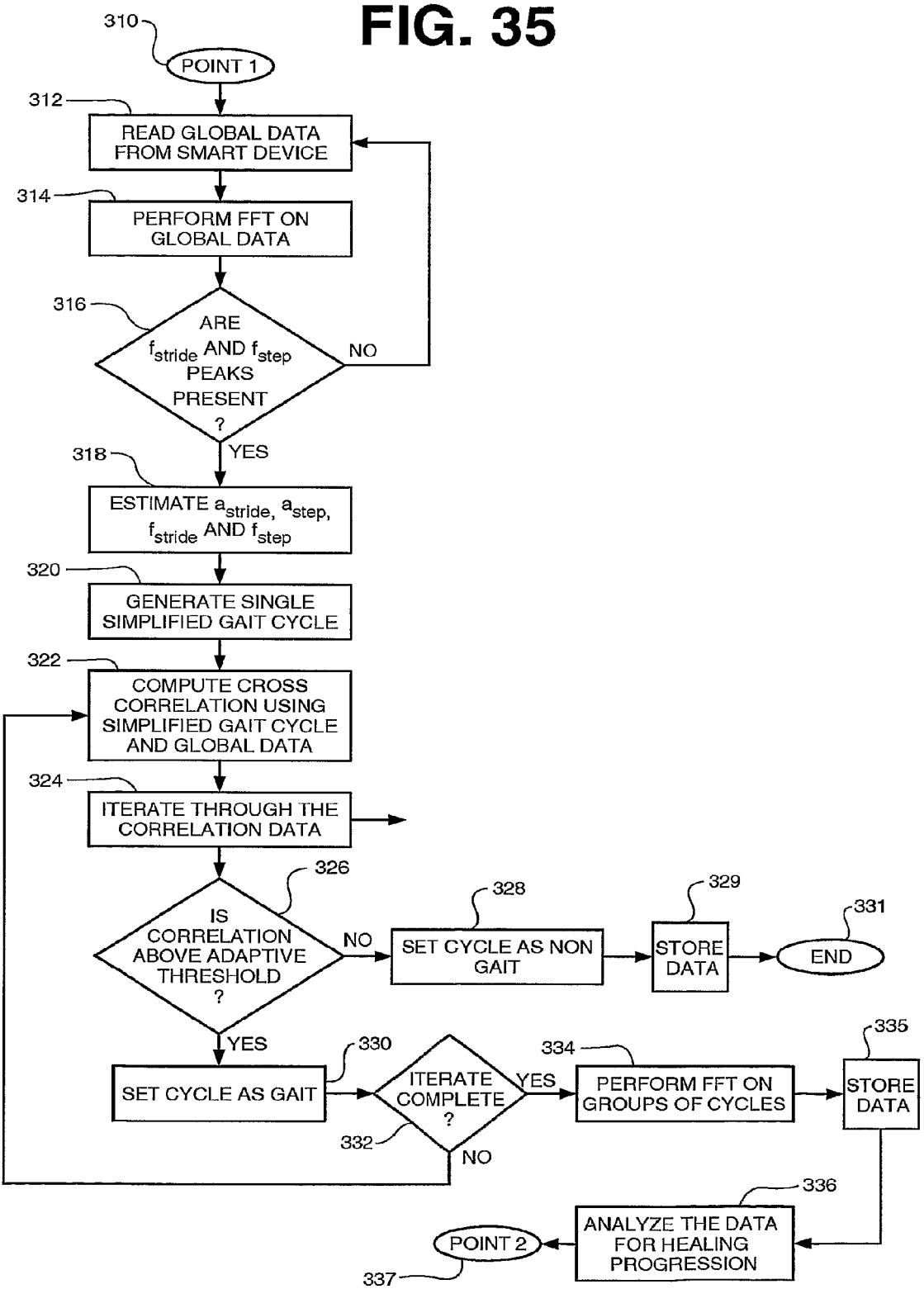
FIG. 35 is flowchart illustrating data processing.

FIG. 35 illustrates steps to implement gait analysis. A person, such as a doctor or healthcare provider, begins at step 310. In step 312, the person reads the data from the patient. For example, the patient may have an active telemetric orthopaedic that continuously measures data as the patient ambulates. In the case of an intramedullary nail as an example, the acceleration of the implant is recorded as the patient ambulates. The surgeon or other healthcare provider may download the data from the implant or control unit in a clinical setting. After the data is downloaded, it is processed in step 314 to convert the data from the time domain to the frequency domain. This allows the doctor, healthcare provider, or software to look for biometric markers or patterns.

Because data is continuously monitored, extraneous data is also downloaded in step 312. For example, data may be recorded when the patient is sitting. In optional step 316, a decision is used to look for peak stride and peak step data within the global download. By utilizing the decision 316, it is ensured that gait information is present in the global data. If gait information is not present, the doctor or healthcare provider returns to step 312 at another time to retrieve global data.

In step 318 to 332, the gait information is extracted and placed into groups for analysis. In this way, it is ensured that the doctor or healthcare provider is looking at how the gait changes from one group to the next. For example, the first group of gait information may be from a first time period and the second group of gait information may be from a second time period.

In step 318, stride amplitude, step amplitude, stride frequency, and step frequency is estimated. In step 320, a simplified single gait cycle group is generated. The global data is broken down and correlated to the simplified single gait cycle group in step 322. The data is processed iteratively in step 324. In step 326, a decision is made whether the correlation is above an adaptive threshold. If so, the correlated cycle is identified as a gait group in step 330. If not, the cycle is determined to be non-gait data in step 328, the data is stored in step 329, and the process ends at step 331. The data is processed iteratively until all the data is analyzed as being gait data or non-gait data in step 332. Once the gait cycles are identified, the gait cycles group are processed in step 334, the data is stored in step 335, the data is analyzed for healing in step 336, and the process completes in step 337.

Alternatively, gait data may be collected and analyzed at the hospital or healthcare facility. In other words, the patient ambulates and data is recorded in the presence of a doctor or healthcare provider. However, this type of data collection does not allow for analysis over long periods of time. Moreover, this type of data collection does not allow for measurement of patient compliance because a patient is more likely to be non-compliant when outside of the hospital or healthcare facility and compliant when in the presence of the doctor or healthcare provider. However, gait data taken at discrete periods of time still provides an indication whether or not a fracture is progressing to a union condition.

Although typically the data is processed outside of the smart device, in some embodiments the data is processed within the smart device and the device outputs the patient healing status. This may be desirable due to data storage constraints. Another output option is a recommendation as to the future of the patient. The device output may be, as examples, "patient should return to the clinic for follow-up in two weeks" or "patient has healed and it is safe to dismiss the patient."

There are several methods of using the data, raw or processed, to help determine the level of healing the patient has undergone. One method is to measure the area under the previously discussed peaks of interest of the area under the global raw data set curve, discrete data set curves, and or the simplified gait curve. These are all indicators of the amount of energy required for those curves to exist. While relative, comparing the total energy to an empirical threshold offers information as to the state of the patient's healing. Further, the statistical measure quadratic mean or root mean square (RMS) also may be used to determine the level of patient healing. In using this tool, a single FIGURE metric of gait normalcy is derived to enable simple comparisons with past and future data obtained from the same patient. This, in turn, enables trend information to be compiled which highlights the patient's progress as a function of time and also enables comparisons with typical trends. Patient healing is inferred from this comparison with typical trend data, in terms of both rate and profile. As an example, the surgeon is provided a "healing number" from 1 to 100, 100 being totally healed. For instance, a patient enters the clinic for evaluation, the surgeon speaks with the patient, reviews the relevant images (for example, CT scans), and reads the smart device. The output to the surgeon is the number 70 indicating to the surgeon that the patient is 70% healed. The surgeon compares that number to the number obtained from the previous visit to the clinic (in this case the number was 50%) to ensure the patient is progressing toward healing. Had the number associated with that patient plateau with respect to time below some relevant threshold, the surgeon then assesses the situation to decide the course of action relating to that patient. This may include surgical intervention, drug therapy, and/or not intervening in any manner.

Figure 36:
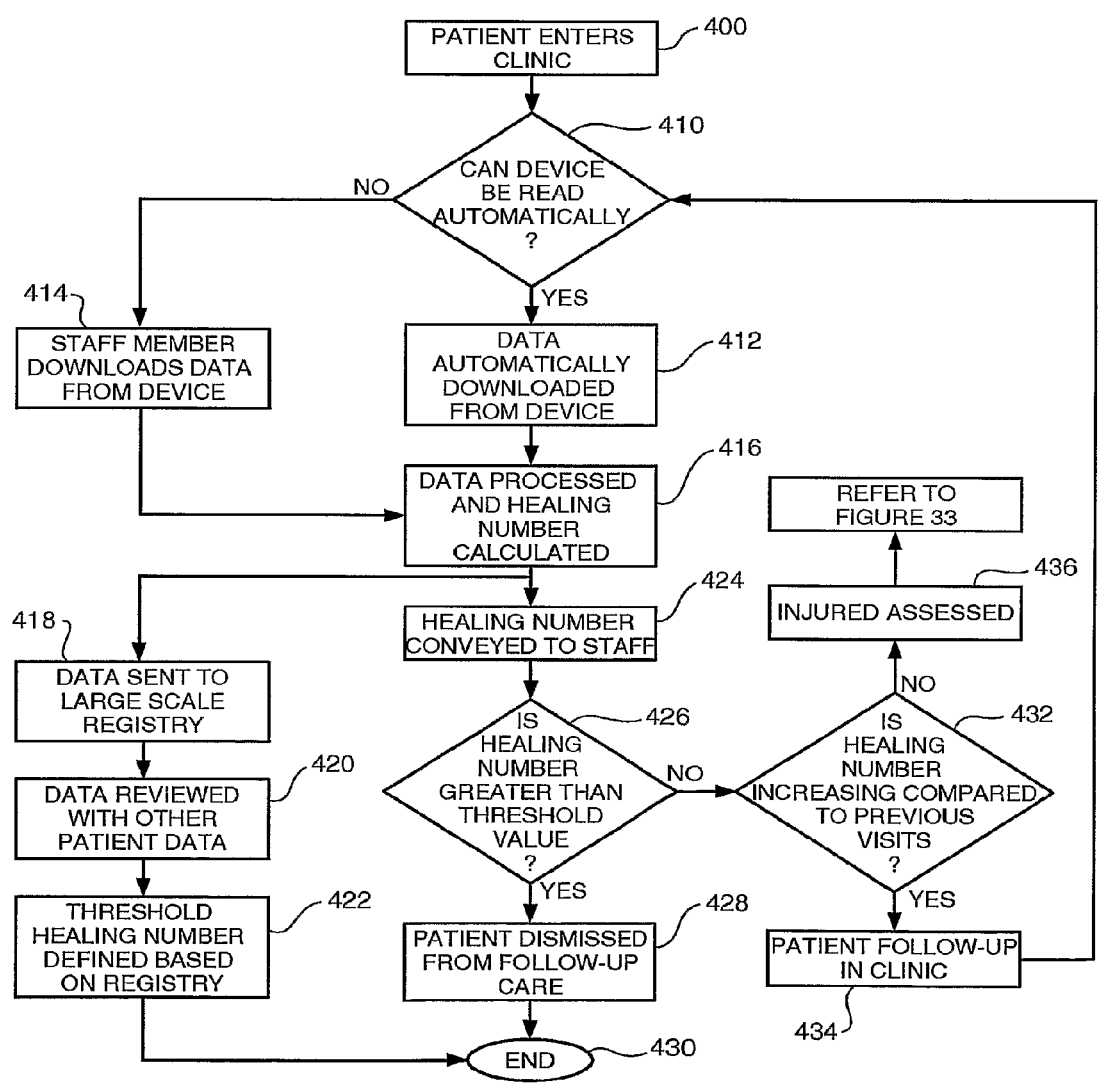
FIG. 36 is a flowchart illustrating the healing number registry.

FIG. 36 illustrates the healing number registry concept. The patient enters the clinic in step 400. In step 410, a decision is made whether the data can be read automatically from the smart implant or wearable sensor. If so, the data is automatically retrieved in operation 412. If not, a user, such as a health care facility staff member, downloads the data in step 414. The data number is processed and the healing number is calculated in step 416. Steps 418, 420 and 422 are optional steps. In step 418, the data is sent to a large scale registry. The registry is initially created using clinical studies, but it is desirable to update the registry with additional values as recorded to more accurately estimate a threshold value. The data is reviewed and compared with other patient data in step 420. A threshold healing number is defined based on the registry in step 422. Initially, the threshold healing number is defined through the use of clinical data. Concurrently with step 418, the healing number is conveyed to a user, such as a health care facility staff member, in step 424. A decision whether the healing number is greater than a threshold value is made in step 426. If the healing number is greater, then the patient is dismissed from follow-up care in step 428, and the process ends in step 430. If the healing number is less than or equal to the threshold, then a decision is made in step 432 whether compared to the previous visit if the healing number is increasing. If so, then the patient is scheduled for follow-up in step 434 and the process returns to step 410. If not, then the injury must be reassessed in step 436. FIG. 33 illustrates the process flow for injury assessment.

The threshold value is empirically driven from a database of patients as time progresses. The patients have the data read from their device, the healing number is calculated, and the healing number then given to the healthcare provider as well as a database. Currently, osteoporosis designation is driven in a similar manner. Osteoporosis is a clinical designation of advanced osteopenia in which the skeletal system is at a reduced state of bone mineral density (BMD). The bone microarchitecture has been altered in a negative manner, and there is an unhealthy level of a variety of non-collagenous proteins. The World Health Organization (WHO) has set the specification for the osteoporosis designation as a person's bone mineral density being 2.5 standard deviations under the peak bone mass of a set standard. The current set standard is the peak bone mass of a 20 year old person. The determination of the bone mineral density of a person is by using dual energy x-ray absorptiometry (DXA or DEXA). Further, a person can be designated with osteoporosis if the suffer a fragility fracture which indicates brittle bone and hence advanced osteopenia.

In other embodiments, the invention is adapted to fit within the total joint arthroplasty (TJA) realm of orthopaedics. One of the most significant differences in a TJA surgery versus traumatic orthopaedic surgery is the planning of the surgery. In TJA surgery, surgical planning with regard to the patient could be years in advance whereas time preparing for a trauma surgery might be as little as a few minutes. Another difference is found in the clinical follow-up of the patient. For TJA, the clinician is looking to ensure the bone is not subsiding from the implant and the implant is not loosening.

An accelerometer may be worn or implanted into a patient receiving a TJA to help further analyze the patient's status in the clinic follow-up. Instead of a healing number, the data analysis output is a "fixation number." A large issue within the realm of large scale TJA is implant loosening whether it aseptic or sepsis related. The fixation number provides the clinical staff input as to whether or not the implant is loosening in hopes of correcting the problem in its early stages or eliminating the problem altogether.

Figure 37:
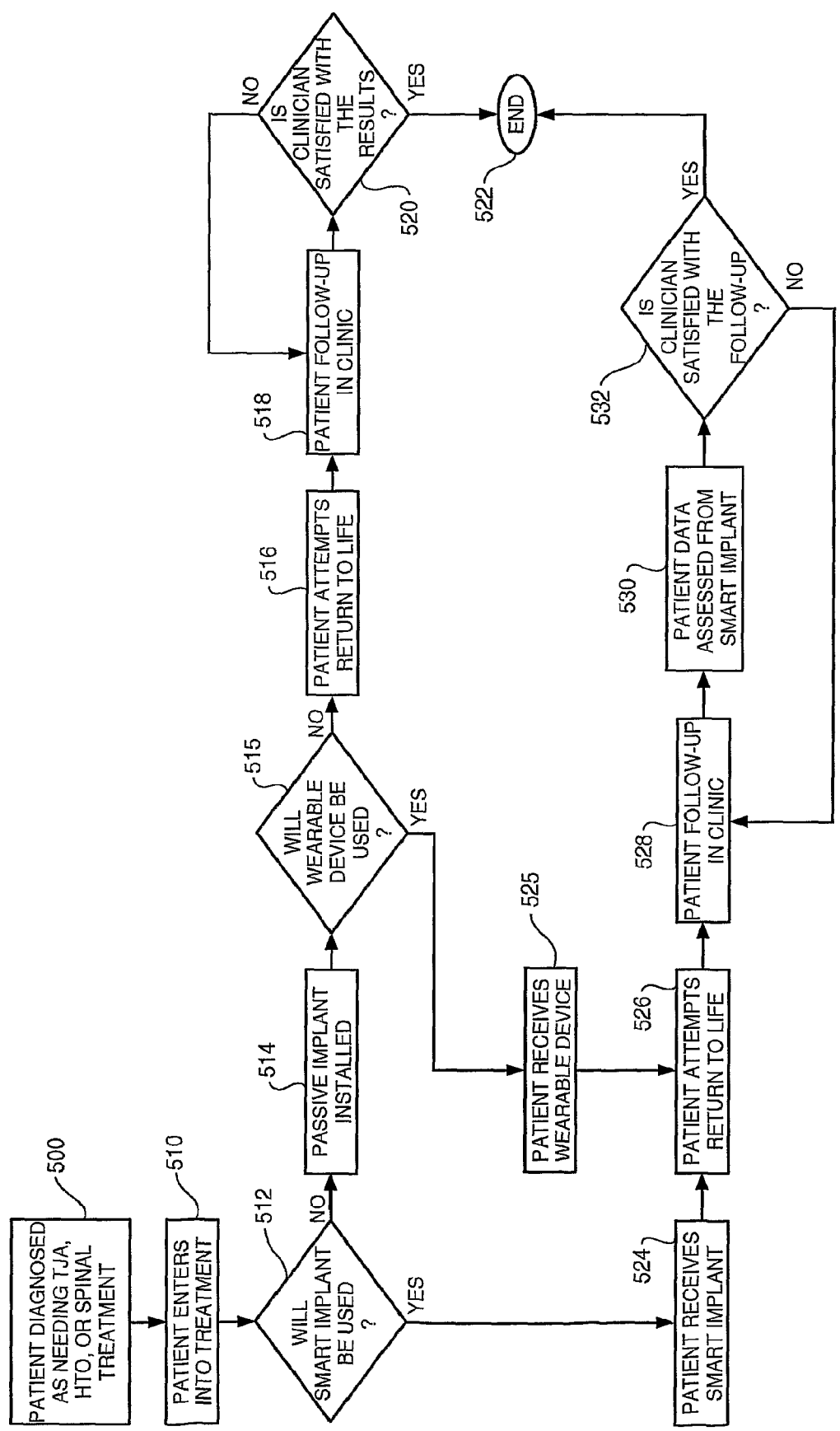
FIG. 37 is a flowchart illustrating adaptation of the system to total joint arthroplasty.

FIG. 37 illustrates the process of retrieving data in total joint arthroplasty. In step 500, the patient is diagnosed with needing total joint arthroplasty. The patient enters into surgery in step 510. In step 512, a decision is made whether a smart implant or a passive implant is installed in the patient. The patient receives a smart implant in step 514, and the patient attempts to return to normal life in step 516. The patient attends a follow-up appointment at a clinic or healthcare facility in step 518. In step 520, a decision is made whether the clinician is satisfied with the follow-up. If not, the patient returns to step 518. If so, the process ends in step 522. Alternatively, the patient receives a smart implant in step 524. The patient attempts to return to normal life in step 526. The patient attends a follow-up in a clinic or healthcare facility in step 528. In step 530, patient data is retrieved and assessed from the smart implant. In step 532, a decision is made whether the clinician is satisfied with the follow-up. If not, the patient returns to step 528. If so, the process ends at step 522.

Another application of the concept is small bone healing status monitoring. All other things remaining equal to that of the clinical follow-up for a lower extremity long bone fracture, within the clinic a predefined simple task is performed by the patient while data is being generated. The data is then processed and compared to a small bone healing number (SBHN). Further, the task may be performed on a scheduled basis outside of the clinic and during the clinic follow-up the data analyzed. For example, a patient having a broken humerus receives a smart nail inserted in an antegrade fashion. The patient is told to perform bicep building exercises daily in a predefined fashion in that the arm is supported in a certain manner and the amount of weight used for the exercise does not change with respect to time. The data is then processed after being downloaded at the clinic where the SBHN is presented to the clinical staff.

Figure 38:
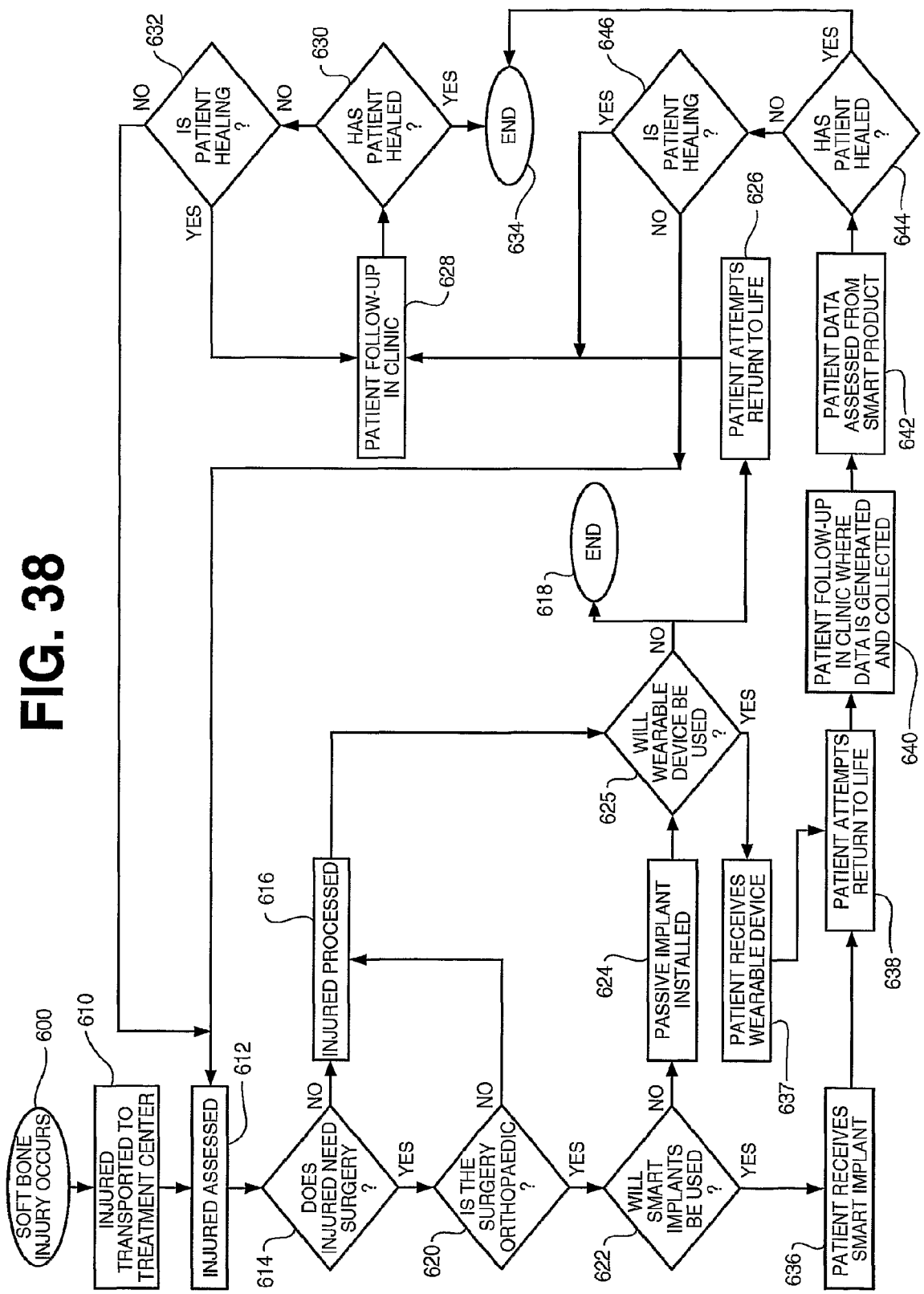
FIG. 38 is a flowchart illustrating the small bone injury smart device application.

FIG. 38 illustrates a flowchart the process for obtaining and assessing patient data in a small bone application. The patient receives a small bone injury in step 600. The patient is transported to a treatment center in step 610. The injury is assessed in step 612. A decision is made in step 614 whether the injured needs surgery. If not, the injury is processed in step 616, and a decision is made at step 625 whether the patient will be provided with a wearable device that includes an accelerometer. If the patient is not fitted with a wearable device, the process ends at step 618. The patient attempts to return to normal life in step 626. Optionally, the patient attends a follow-up appointment at step 628. In step 630, a decision is made whether the patient has healed. If not, the injury is assessed to inquire whether the patient is in fact healing in step 632. If not, the patient returns to step 612. If the injury is healing, the patient returns to step 628. When the patient has healed, the process ends at step 634.

If the patient does need surgery at step 614, another decision is made in step 620 whether the surgery is orthopaedic in nature. If not, the patient proceeds to step 616. If the patient does require orthopaedic surgery, a decision is made in step 622 whether the patient will receive a smart implant. If not, the patient receives a passive implant in step 624. The patient then proceeds to step 625, where a decision is made whether the patient will receive a wearable device that includes an accelerometer. If not, the patient proceeds to step 626 and possibly step 628. Otherwise, the patient receives a wearable device in step 637 and attempts to return to normal life in step 638.

Alternatively, the patient receives a smart implant at step 636 and attempts to return to normal life at step 638. The patient attends a follow-up appointment at a clinic or healthcare facility in step 640. In step 642, data from the smart implant or wearable device is retrieved and assessed. In step 644, a decision is made whether the injury has healed. If not, a decision is made whether the injury is in fact healing in step 646. If so, the patient attends a follow-up appointment in step 640. If the injury is not healing, the patient returns to step 612 for further evaluation. If the patient has healed, however, then the process ends at step 634.

Other problems are implant loosening and de-stabilization which impose risk to the patient and are of great cost to the healthcare system. There are many sources of both implant loosening (aseptic loosening, bone subsidence, etc.) and implant de-stabilization (bone subsidence, poor fixation purchase, etc.). Another source is inadequate operative stabilization. Therefore, if intra-operative stability is determinable, the risk and cost associated with loosening and de-stabilization could be reduced.

Figure 39:
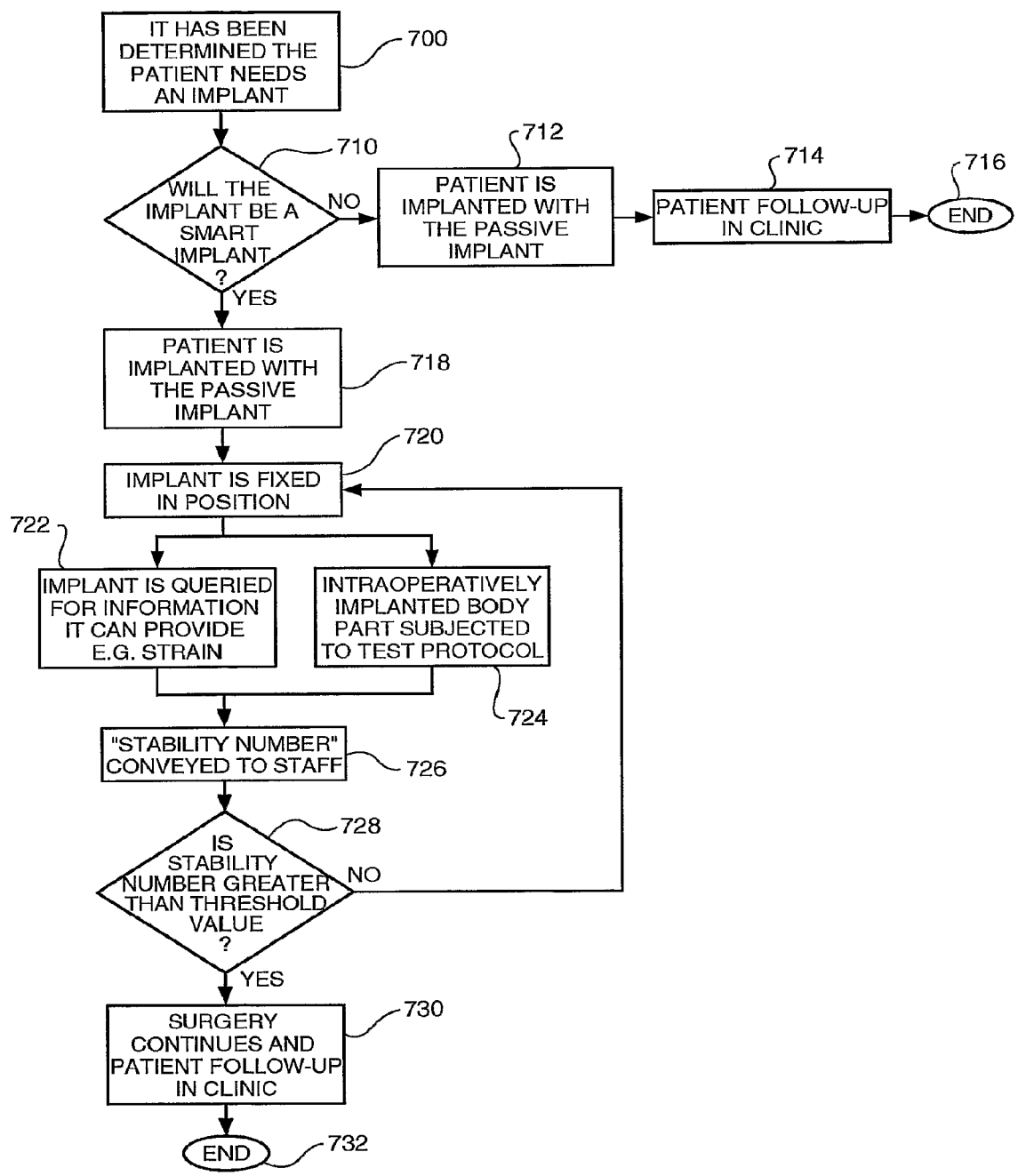
FIG. 39 is a flowchart illustrating intraoperative implant stability determination.

FIG. 39 illustrates a flowchart for determining intraoperative implant stability. In step 700, it is determined that the patient needs an implant to help facilitate healing. A decision is made in step 710 whether the patient will receive a smart implant. If not, the patient receives a passive implant in step 712. The patient attends one or more follow-up appointments in step 714, and the process ends in step 716. Alternatively, the patient receives a smart implant, such as one containing a strain sensing element, an accelerometer, a gyroscope, or a MEMs device, in step 718. The implant is fixed within, on, or near the injured body part (e.g., bone cement or transfixion elements, such as screws) in step 720. The implant is then queried (wired or wirelessly) while the body part undergoes a testing protocol, such as repeated flexion and extension of the knee, after the implant has been secured in place in steps 722 and 724. The raw data or processed data from the query is given to the surgical staff in the form of a stability number in step 726. In step 728, the staff member then decides if the implant is secure. If the stability is not satisfactory, the staff can return to step 720 to improve the fixation of the implant and repeat the query and analysis until the stability is satisfactory. If the stability is satisfactory, the remaining steps of the surgery take place and the patient follow up with the clinical staff in the future. The process ends at step 732.

In some embodiments, a patient receives a wireless instrumented joint reconstruction product. The electromechanical system within the implant is used to monitor patient recovery using one or more sensors, and make a decision as to whether any intervention is required in the patient's rehabilitation. The telemetrized joint replacement continuously measures a complete set of accelerometer values generated in the implant and transmits them from the patient to a laboratory computer system without disturbing the primary function of the implant. Alternatively, a wired system is utilized in the form of a wearable device external to the patient. Again, the electromechanical system is used to monitor various aspects of the patient's recovery.

The technology associated with the instrumentation procedure also could be adapted to monitor soft tissue repair (e.g., skin muscle, tendons, ligaments, cartilage, etc.) and the repair and monitoring of internal organs (kidney's, liver, stomach, lungs, heart, etc)

The sensed data is processed as described herein to provide the clinician with the following information to better help the patient.

(a) Measure the maximum strain in the implant during the entire fracture healing period (from 8 weeks to 3 months depending on whether union or non-union fracture healing occurs)

(b) Monitor the healing status of the implant for the entire lifetime of the patient to look for any changes in bone physiology, which may occur through disease or trauma, that may influence the performance of the implant.

(c) Estimate the load component in the healing bone by subtracting the implant load from the total load measured in the operated limb.

(d) Measure the stiffness (strain rate) required for various activity levels in patients of different weights.

(e) Estimate the degree of healing from the early time points to enable the Surgeon to act promptly in the event that non-union or delayed union is detected.

(f) The ability to actively modify the stiffness of a partially resorbable implant to encourage the bone to carry more load if the algorithm detects that the bone is not healing properly.

Figure 40:
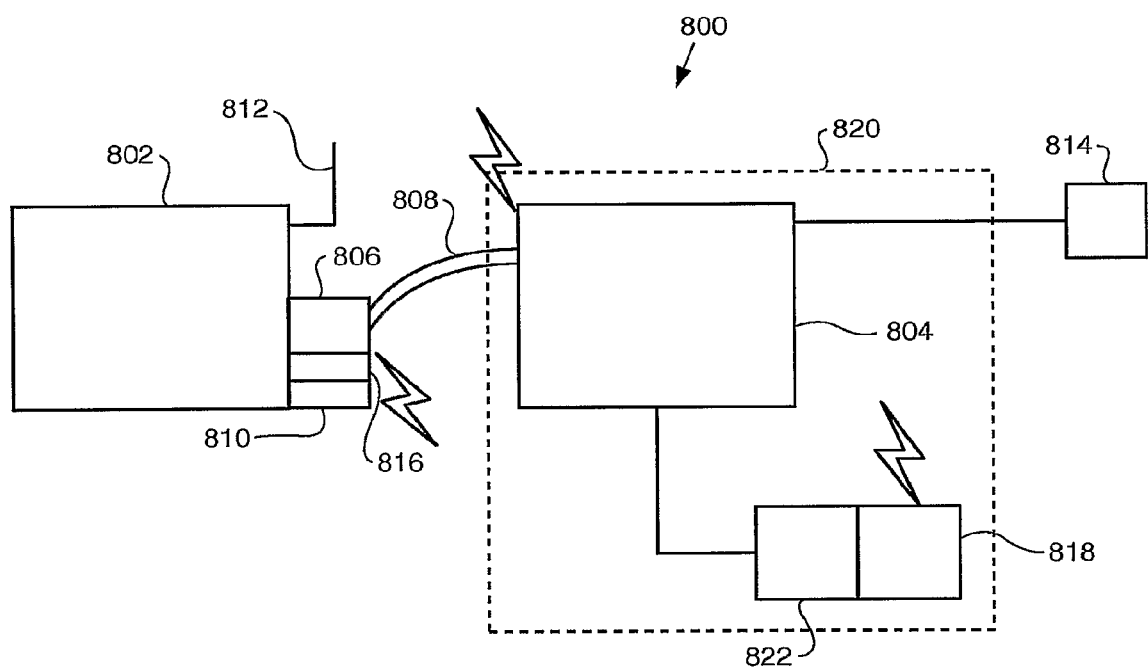
FIG. 40 is a schematic illustrating a system for processing accelerometer data.

FIG. 40 illustrates a system 800 for processing accelerometer data. The system 800 includes an accelerometer 806, a first processor 810, a power supply 816, and a second processor 804. The accelerometer 806 is used to measure a physiological acceleration parameter of a subject 802. As examples, the accelerometer and the first processor may be located within a medical implant implanted within the subject or located within a wearable device operatively connected to the subject. The first processor 810 is operatively connected to the accelerometer 806, and the first processor 810 is configured to receive the acceleration parameter from the accelerometer 806 and configured to output machine readable acceleration data. In some embodiments, the accelerometer 806 and the first processor 810 comprise a single unit. The machine readable acceleration data includes, among other things, time domain accelerometer data. The power supply 816 is electrically connected to the first processor 810. The second processor 804 is configured to receive the machine readable acceleration data and transform the time domain accelerometer data into frequency domain accelerometer data. The second processor 816 receives the machine readable acceleration data from the first processor either by wire or wirelessly. Thereafter, the frequency domain accelerometer data can be used to decide whether the subject is progressing in healing status or if in fact the subject has healed.

In some embodiments, the system 800 includes an antenna 812. The antenna 812 may be electrically connected to the first processor or to the accelerometer. The antenna 812 may be used to transmit the acceleration data. Additionally, the antenna may form an inductive coupling element used to power the first processor and the accelerometer. The antenna and the first processor may form a single component. Alternatively, the antenna and the power supply may form one component.

In some embodiments, the first processor and the second processor are incorporated into a single unit. In the depicted embodiment, however, the first processor and the second processor are separate components. In FIG. 40, the second processor 804 is part of a remote processing system 820. The remote processing system 820 may include a reader 818. The reader 818 may be used to receive the machine readable data from the first processor 810. The remote processing system 820 may include a display unit and/or a sound generating unit. After the frequency domain data is analyzed, the display unit or the sound generating unit may be used to inform a user of the subject's healing status or whether the subject has progressed in healing.

The first processor or the second processor may form part of a computer assisted surgery system. Alternatively, the first processor or the second processor may be electrically connected to the computer assisted surgery system for the communication of data.

Numerous possibilities are available for powering the system 800 or portions thereof. As examples, the power supply may be a capacitor, an inductive coupling, a battery, a mechanically driven power generation unit, a piezoelectric device, or an energy scavenging device. In some embodiments, the first processor and the accelerometer are powered by one or more of a capacitor, an inductive coupling, a battery, a mechanically driven power generation unit, a piezoelectric device, or an energy scavenging device. In yet other embodiments, the machine readable acceleration data, the time domain acceleration data, the frequency domain acceleration data, or combinations thereof are communicated under power from one or more of a capacitor, an inductive coupling, a battery, a mechanically driven power generation unit, a piezoelectric device, and an energy scavenging device.

CONCLUSION

Although the depicted embodiments concentrate on the function of an instrumented intramedullary nail designed specifically for bone healing, alternative embodiments include incorporation of the sensor and other electronic components within other implantable trauma products, such as a plate, a bone screw, a cannulated screw, a pin, a rod, a staple and a cable. Further, the instrumentation described herein is extendable to joint replacement implants, such a total knee replacements (TKR) and total hip replacements (THR), dental implants, and craniomaxillofacial implants.

A patient receives a wireless instrumented joint reconstruction product. The electromechanical system within the implant may be used to monitor patient recovery using one or more sensors, and make a decision as to whether any intervention is required in the patient's rehabilitation. The telemetric joint replacement continuously measures a complete set of strain values generated in the implant and transmits them from the patient to a laboratory computer system without disturbing the primary function of the implant. Alternatively, a wired system may be utilized in the form of a wearable device external to the patient. Again, the electromechanical system could be designed to monitor various aspects of the patient's recovery.

The wireless technology may be introduced into dental implants to enable early detection of implant overloading. Overloading occurs when prolonged excessive occlusal forces applied to the implant exceeded the ability of the bone-implant interface to withstand and adapt to these forces, leading to fibrous replacement at the implant interface, termed "osseodisintegration," and ultimately to implant failure. Again, a communication link may be used to selectively access the strain data in the memory from an external source.

The technology associated with the instrumentation procedure also may be adapted to monitor soft tissue repair (e.g. skin muscle, tendons, ligaments, cartilage etc.) and the repair and monitoring of internal organs (kidney's, liver, stomach, lungs, heart, etc.).

The invention includes a system for processing accelerometer data. The system includes an accelerometer, a first processor, a power supply, and a second processor. The accelerometer measures a physiological acceleration parameter. The accelerometer data may be processed and analyzed to determine whether the subject is progressing towards a healed state or if in fact the subject has healed.

The invention includes a first embodiment of a method for determining the healing progression status of a subject. The method includes the steps of: (a) collecting accelerometer data through use of an accelerometer operatively connected to the subject; (b) retrieving the collected accelerometer data, the accelerometer data having a time domain component; (c) transforming the time domain accelerometer data into frequency domain accelerometer data; and (d) analyzing the frequency domain accelerometer data for healing progression of the subject. Optional steps may include wirelessly conveying accelerometer data to a remote processing system and communicating the analysis of the data to a user. In general, the accelerometer data is taken while the subject is undergoing a predefined task. For example, the predefined task may be ambulation. The predefined task may be performed preoperatively, intraoperatively, or postoperatively. For the intraoperative step, the subject may be assisted by a surgeon or other medical professional to perform the predefined task.

The invention includes a second embodiment for determining the healing progression status of a subject. The method includes the steps of: (a) attaching an accelerometer to a subject; (b) collecting accelerometer data through use of the accelerometer; and (c) analyzing the accelerometer data to determine if the subject has progressed in healing status. The step of attaching an accelerometer to a subject includes installing a smart implant in the subject. As examples, the smart implant may be a bone plate, a bone screw, a bone peg, a bone staple, an intramedullary nail, an intramedullary nail cap, an intramedullary nail/plate, an interference screw, a hip replacement stem, a hip replacement femoral neck, a hip replacement femoral head, a hip replacement acetabular liner, a hip replacement acetabular shell, a knee replacement tibial tray, a knee replacement tibial tray liner, a knee replacement femoral component, a knee replacement tibial tray shaft extension, a knee replacement patellar implants, a knee replacement wedges, a trochlear groove implant, a femoral canal restrictor, a shoulder replacement humeral stems, a shoulder replacement glenoid component, a shoulder replacement humeral head, an elbow replacement humeral component, an elbow replacement radial component, an elbow replacement ulnar component, an ankle replacement tibial component, or an ankle replacement talar component.

Alternatively, the step of attaching an accelerometer to a subject may include attaching a wearable device to the subject. As examples, the wearable device may be worn on a thigh, a distal femur, a proximal tibia, a distal tibia, an arm, a waist, a head, a wrist, a chest, embedded within a shoe, on a shoe, on a cast, or on a brace The advantage of the invention over the prior art concerns the incorporation of the components within the fixation device in a manner that protects the components, provides an accurate and stable connection between the sensor and its environment, maintains the functionality of the implant itself, and is suitable for large scale manufacture. The device allows for information to be gathered and processed yielding useful clinical data with respect to a patient's bone healing cascade.

The instrumented device removes the guessing from the conventional diagnostic techniques, such as x-ray, CT and MRI imaging, by providing the patient objective quantitative data collected from them through the healing process. Currently, there is no device which quantifies the skeletal loads encountered during fracture healing, as well as during different patient and physiotherapy activities. Furthermore, the load distribution between the implant and the adjacent bone during fracture healing is also unknown. Such data help to optimize postoperative protocols for improved fracture healing. The device described herein addresses this by having on board sensors and a memory facility enabling patient data to be stored thus allowing for early transmission of data. This data includes patient history and patient activity. The device also enables early intervention by the surgeon, if required, such as administration of drugs, injection of orthobiologics, cements or demineralized bone matrix to help promote/accelerate bone healing or a revision surgery.

The device described herein is an instrumented intramedullary (IM) nail or wearable device with the capacity to provide an accurate measurement of the changes in acceleration of the nail or body part of the patient. In the instrumented nail scenario, the device consists of sensors and associated electronic components located in machined cavities on the outer surface of the nail. The hermetically sealed housing described in the present invention has been described previously. Incorporation of sensors and other electronic components within an implantable medical device such as an intramedullary nail alters its primary function from a passive (load-supporting device) to a smart "intelligent" system with the ability to record and monitor patient activity and compliance. Similarly, the wearable device consists of sensors and associated electronic components and is worn preferably on the injured limb, for example the thigh corresponding to a tibia fracture on the same side of the patient's body.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A system for processing accelerometer data, the system comprising:
   a. an accelerometer for measuring a physiological acceleration parameter;
   b. a first processor operatively connected to the accelerometer, the first processor configured to receive the acceleration parameter from the accelerometer and configured to output machine readable acceleration data, the machine readable acceleration data comprising time domain accelerometer data;
   c. a power supply electrically connected to the first processor; and
   d. a second processor configured to:
      receive the machine readable acceleration data,
      transform the time domain accelerometer data into frequency domain accelerometer data, the frequency domain accelerometer data comprising data about one or more gait cycles,
      analyze a bone healing progression based on the frequency domain accelerometer data, and
      output a healing number that indicates a percentage of bone healing in the area surrounding the implant,
   wherein, to analyze the bone healing progression based on the frequency domain accelerometer data, the second processor is configured to analyze the frequency domain accelerometer to determine a level of bone healing of a subject in an area surrounding the intramedullary nail based on the data about the one or more gait cycles;
wherein the accelerometer and the first processor are located within the intramedullary nail or an intramedullary nail cap.

2. The system according to claim 1, wherein the accelerometer and the first processor are located within a medical implant.

3. The system according to claim 1, wherein the accelerometer and the first processor are located within a wearable device.

4. The system according to claim 1, wherein an antenna is operatively connected to the first processor and the antenna is configured to transmit the machine readable acceleration data.

5. The system according to claim 1, wherein the accelerometer, the first processor, and the second processor are located within the intramedullary nail or the intramedullary nail cap.

6. The system according to claim 1, wherein the accelerometer and the first processor comprise one unit.

7. The system according to claim 4, wherein the antenna and the power supply comprise one unit.

8. The system according to claim 1, further comprising a reader for retrieving accelerometer data.

9. The system according to claim 1, wherein at least one of the first processor and the second processor is part of a computer assisted surgery system.

10. The system according to claim 4, wherein the antenna used to transmit the accelerometer data is also an inductive coupling element used to power the first processor and the accelerometer.

11. The system according to claim 1, wherein the power supply includes at least one of a capacitor, an inductive coupling, a battery, a mechanically driven power generation unit, a piezoelectric device, and an energy scavenging device.

12. The system according to claim 1, wherein the first processor and accelerometer are powered by at least one of a capacitor, an inductive coupling, a battery, a mechanically driven power generation unit, a piezoelectric device, and an energy scavenging device.

13. The system according to claim 1, wherein at least one of the machine readable acceleration data, the time domain accelerometer data, and the frequency domain accelerometer data is communicated under power from at least one of a capacitor, an inductive coupling, a battery, a mechanically driven power generation unit, a piezoelectric device, and an energy scavenging device.

14. The system according to claim 1, wherein the second processor is part of a remote processing system.

15. The system according to claim 14, wherein the remote processing system includes at least one of a display unit and a sound generating unit.

16. A method of determining the healing progression status of a subject having an intramedullary implant, the method comprising:
executing instructions stored on one or more machine-readable memory devices with one or more processors, wherein at least one of the one or more processors is operatively connected to an accelerometer that is operatively connected to the subject, wherein executing the instructions causes the one or more processors to perform the steps of:
a) collecting accelerometer data from the accelerometer;
b) retrieving the collected accelerometer data, the accelerometer data having a time domain component;
c) transforming the time domain accelerometer data into frequency domain accelerometer data, the frequency domain accelerometer data comprising data about one or more gait cycles;
d) analyzing the frequency domain accelerometer data for bone healing progression of the subject in an area surrounding the intramedullary implant, wherein analyzing the frequency domain accelerometer data comprises determining a level of bone healing of the subject in the area surrounding the intramedullary implant based on the data about the one or more gait cycles; and
e) outputting a healing number that indicates a percentage of bone healing in the area surrounding the intramedullary implant.

17. A system for processing accelerometer data, the system comprising:
a) an accelerometer for measuring a physiological acceleration parameter;
b) a first processor operatively connected to the accelerometer, the first processor configured to receive the acceleration parameter from the accelerometer and configured to output machine readable acceleration data, the machine readable acceleration data comprising time domain accelerometer data;
c) a power supply electrically connected to the first processor; and
d) a second processor configured to:
receive the machine readable acceleration data,
transform the time domain accelerometer data into frequency domain accelerometer data, and
analyze a bone healing progression of a patient in an area surrounding an implant based on the frequency domain accelerometer data,
wherein, to analyze the bone healing progression based on the frequency domain accelerometer data, the second processor is configured to:
extract, from the time domain acceleration data, multiple discrete data sets;
identify, based on the frequency domain accelerometer data corresponding to the multiple discrete data sets, a subset of the multiple discrete data sets that each comprise data about one or more gait cycles; and
determine a level of bone healing of the patient in the area surrounding the implant based on the subset of the multiple discrete data sets that each comprise data about one or more gait cycles;
wherein, to determine the level of healing based on the data about the one or more gait cycles, the second processor is configured to:
measure an area under particular regions of curves representing the frequency domain accelerometer data corresponding to the subset of discrete data sets; and
determine the level of bone healing of the patient in the area surrounding the implant based on the measured area.

18. The method according to claim 16, wherein analyzing the frequency domain accelerometer data for bone healing progression of the subject in an area surrounding the intramedullary implant comprises:
comparing the level of bone healing to a previous level of bone healing.

19. The method according to claim 18, wherein:
the collected accelerometer data is collected over a first time period; and
the previous level of bone healing is based on accelerometer data for a time period that occurs before the first time period.

20. The method according to claim 16, wherein analyzing the frequency domain accelerometer data for bone healing progression of the subject in an area surrounding the intramedullary implant comprises:
generating a bone healing metric based on the frequency domain accelerometer data; and
comparing the bone healing metric to a threshold level derived from healing data for multiple patients.

21. The system according to claim 17, wherein the frequency domain accelerometer data indicates activity of a patient; and
wherein, to analyze the healing progression based on the frequency domain accelerometer data, the second processor is configured to analyze the healing progression of the patient based on the activity of the patient indicated by the frequency domain accelerometer data.

22. The system according to claim 1, wherein, to analyze the healing progression based on the frequency domain accelerometer data, the second processor is configured to identify a portion of the frequency domain accelerometer data corresponding to the one or more gait cycles.

23. The system according to claim 1, wherein to analyze the healing progression based on the frequency domain accelerometer data, the second processor is configured to:
identify data corresponding to a step point and a stride point; and
analyze the healing progression based on the data corresponding to the step point and the stride point.

24. The system according to claim 1, wherein, to analyze the healing progression based on the frequency domain accelerometer data, the second processor is configured to identify a gait characteristic using the frequency domain accelerometer data.

25. The system according to claim 24, wherein the gait characteristic is one of a stride amplitude, a step amplitude, a stride frequency, and a step frequency.

26. The system according to claim 1, wherein, to analyze the healing progression based on the frequency domain accelerometer data, the second processor is configured to determine the normalcy of an activity of the subject based on the frequency domain accelerometer data.

27. The system according to claim 1, wherein, to determine the level of healing based on the data about the one or more gait cycles, the second processor is configured to generate a gait normalcy metric based on an amplitude or an area of the frequency domain accelerometer data corresponding to the one or more gait cycles.

* * * * *